(12) United States Patent
Wang et al.

(10) Patent No.: US 11,003,791 B2
(45) Date of Patent: May 11, 2021

(54) SYSTEM FOR DECENTRALIZED OWNERSHIP AND SECURE SHARING OF PERSONALIZED HEALTH DATA

(71) Applicant: Novo Vivo Inc., Palo Alto, CA (US)

(72) Inventors: Shuang Wang, Zhenjiang (CN); Xiaofeng Wang, Zhenjiang (CN); Haixu Tang, Zhenjiang (CN); Wenhao Wang, Zhenjiang (CN); Ali Farahanchi, Zhenjiang (CN); Hao Zheng, Zhenjiang (CN)

(73) Assignee: Hangzhou Nuowei Information Technology Co., Ltd., Hangzhou (CN)

( * ) Notice: Subject to any disclaimer, the term of this patent is extended or adjusted under 35 U.S.C. 154(b) by 0 days.

(21) Appl. No.: 16/402,162

(22) Filed: May 2, 2019

(65) Prior Publication Data

US 2020/0327250 A1      Oct. 15, 2020

Related U.S. Application Data

(63) Continuation of application No. PCT/CN2019/082539, filed on Apr. 12, 2019.

(51) Int. Cl.
*G06F 21/62* (2013.01)
*G06F 21/60* (2013.01)
(Continued)

(52) U.S. Cl.
CPC ........ *G06F 21/6245* (2013.01); *G06F 21/602* (2013.01); *G06N 20/00* (2019.01);
(Continued)

(58) Field of Classification Search
CPC . G06F 21/6245; G06F 21/602; H04L 9/0637; H04L 2209/38; G16H 10/60;
(Continued)

(56) References Cited

U.S. PATENT DOCUMENTS

| 8,589,437 B1 | 11/2013 | Khomenko et al. |
| 2009/0112871 A1 | 4/2009 | Hawthorne et al. |

(Continued)

FOREIGN PATENT DOCUMENTS

| CN | 105812126 A | 7/2016 |
| CN | 108074629 A | 5/2018 |

(Continued)

OTHER PUBLICATIONS

Chen, et al., Princess: Privacy-protecting Rare disease International Network Collaboration via Encryption through Software guard extensionS. Bioinformatics, 33(6), 2017, 871-878 doi: 10.1093/bioinformatics/btw758.

(Continued)

*Primary Examiner* — Malcom Cribbs
(74) *Attorney, Agent, or Firm* — Dragon Sun Law Firm, PC; Jinggao Li, Esq.

(57) ABSTRACT

The system disclosed implements a secure method for facilitating secure exchange of health information among various stakeholders, including data owners or contributors, data requestors or miners, and medical providers, including hospitals, clinics, and research laboratories. Additional aspects of the system provide means for conducting secure research on health data collected from data contributors. Health information is exchanged using a decentralized system that incentivizes data contributors to provide health data to data miners. The data miners, which may be pharmaceutical companies, medical laboratories, or hospitals, use various methods in order to perform research on aggregated contributor data, while maintaining contributor privacy.

20 Claims, 32 Drawing Sheets

(51) Int. Cl.
*H04L 9/06* (2006.01)
*G16H 50/70* (2018.01)
*G06N 20/00* (2019.01)
*G16B 40/00* (2019.01)
*G16B 50/40* (2019.01)
*G16H 10/60* (2018.01)

(52) U.S. Cl.
CPC ............ *G16B 40/00* (2019.02); *G16B 50/40* (2019.02); *G16H 10/60* (2018.01); *G16H 50/70* (2018.01); *H04L 9/0637* (2013.01); *H04L 2209/38* (2013.01)

(58) Field of Classification Search
CPC ........ G16H 50/70; G06N 20/00; G16B 40/00; G16B 50/40
See application file for complete search history.

(56) References Cited

U.S. PATENT DOCUMENTS

| | | | |
|---|---|---|---|
| 2014/0350954 A1* | 11/2014 | Ellis | G16H 50/20 705/2 |
| 2015/0332283 A1 | 11/2015 | Witchey | |
| 2017/0039330 A1* | 2/2017 | Tanner, Jr. | G06F 19/328 |
| 2017/0039930 A1 | 2/2017 | Li | |
| 2017/0359374 A1 | 12/2017 | Smith et al. | |
| 2018/0060496 A1* | 3/2018 | Bulleit | H04L 9/3239 |
| 2018/0089374 A1* | 3/2018 | Gibson | G16H 30/20 |
| 2018/0167200 A1* | 6/2018 | High | A61B 5/1171 |
| 2019/0012466 A1* | 1/2019 | Ricotta | H04L 63/0457 |
| 2019/0027237 A1* | 1/2019 | McFarlane | H04L 9/3247 |
| 2019/0065681 A1* | 2/2019 | Gmeiner | G16H 40/20 |
| 2019/0124146 A1* | 4/2019 | Austin | H04L 9/0643 |
| 2019/0156923 A1* | 5/2019 | Kain | G06F 16/2379 |
| 2019/0173854 A1* | 6/2019 | Beck | H04L 9/3247 |
| 2019/0237169 A1* | 8/2019 | Culver | H04L 9/3247 |
| 2019/0244697 A1* | 8/2019 | Farrell | G16H 40/20 |
| 2019/0303867 A1* | 10/2019 | Nair | H04L 63/12 |
| 2019/0354693 A1* | 11/2019 | Yoon | G06F 21/6245 |
| 2020/0117818 A1* | 4/2020 | Latka | G06F 12/1466 |

FOREIGN PATENT DOCUMENTS

| | | |
|---|---|---|
| CN | 108881160 A | 11/2018 |
| WO | WO-2017176093 A1 | 10/2017 |
| WO | WO-2018160737 A1 | 9/2018 |

OTHER PUBLICATIONS

Chen, et al., Racing in Hyperspace: Closing Hyper-Threading Side Channels on SGX with Contrived Data Races. IEEE; May 20-24, 2018: 1-17.

Chenghong, et al., Scotch: Secure Counting Of encrypTed genomiC data using a Hybrid approach. AMIA Annu Symp Proc. 2017; 2017: 1744-1753.

Jiang, et al., WebGLORE: a Web service for Grid LOgistic Regression. Bioinformatics Applications Note, vol. 29 No. 24, 2013; pp. 3238-3240.

Lee, et al., Privacy-Preserving Patient Similarity Learning in a Federated Environment: Development and Analysis. JMIR Med Inform 2018; vol. 6 iss.2 e20: 1-21.

Li, et al., VERTIcal Grid Oigistic regression (VERTIGO), J Am Med Inform Assoc 2016; 23:570-579.

Wang, et al., Leaky Cauldron on the Dark Land: Understanding Memory Side-Channel Hazards in SGX. Cornell University, Oct. 30-Nov. 3, 2017; 2421-2434.

Wang, et al., Mechanisms to protect the privacy of families when using the transmission disequilibrium test in genome-wide association studies. Bioinformatics, 33(23), 2017, 3716-3725.

PCT/CN2019/082539 International Search Report and Written Opinion dated Jan. 2, 2020.

* cited by examiner

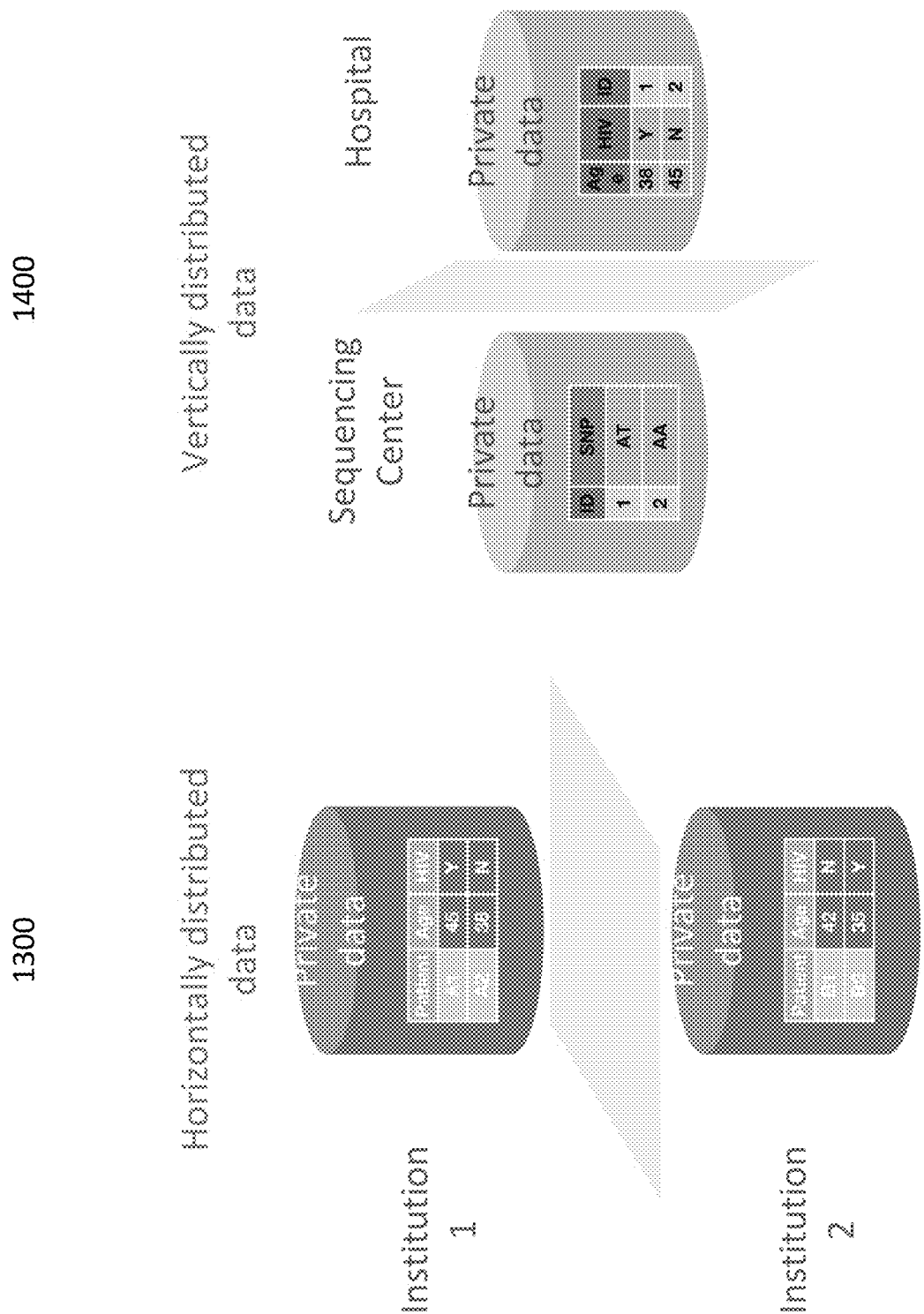

| # of total records | Federated Logistic Regression with vertically distributed data | | | | Horizontally distributed data (Prime) |
|---|---|---|---|---|---|
| | Iterative Hessian on CPU | Fixed Hessian on CPU | Iterative Hessian on GPU | Fixed Hessian on GPU | |
| 2,000 | 2.84 s | 7.03 s | 1.69 s | 7.01 s | 0.72 s |
| 4,000 | 12.51 s | 8.68 s | 6.55 s | 8.22 s | 1.71 s |
| 8,000 | 66.38 s | 15.3 s | 28.57 s | 11.05 s | 4.1 s |
| 20,000 | 815.6 s | 101.7 s | - | - | 26.5 s |

FIG. 21

Table 1. Run time performance for conducting different analysis tasks using secureVC and BCFtools.

| Key commands | SecureVC | BCFtools | Overhead |
|---|---|---|---|
| call | 141.482s | 119.738s | 15.36% |
| concat | 62.24s | 56.39s | 10.37% |
| mpileup | 324.14s | 283.15s | 12.64% |

All results were obtained through averaging over 5 trials.

2950

2900

TABLE IV. BENCHMARKING BASIC OPERATIONS UNDER DIFFERENT $n$'S AND THE DEFAULT $q$'S PROVIDING 128-BIT SECURITY (UNIT: MICRO-SECOND). THE TIME IS MEASURED WITH TASKS RUNNING ON A SINGLE CORE. THE DASH SYMBOL INDICATES THAT A SOFTWARE-BASED BOOTSTRAPPING CANNOT BE PERFORMED FOR THE GIVEN PARAMETERS.

| $n$ | 4096 | 8192 | 16384 | 32768 |
|---|---|---|---|---|
| encryption | 4208 | 9725 | 25211 | 70950 |
| decryption | 510 | 1897 | 7422 | 28142 |
| addition | 14 | 58 | 242 | 923 |
| multiplication | 5221 | 19974 | 83991 | 357404 |
| square | 3505 | 13533 | 57933 | 251999 |
| relinearization | 711 | 3956 | 25042 | 160077 |
| software-only bootstrapping | – | – | $1.09 \times 10^9$ | $2.46 \times 10^{10}$ |
| SGX bootstrapping | 7881 | 25044 | 87840 | $1.00 \times 10^6$ |

TABLE V. EVALUATION ON A LOGISTIC REGRESSION TASK (TIME MEASURED IN SECONDS).

| | Key Generation | Data Preparation | Iteration | Memory |
|---|---|---|---|---|
| SEAL | 422.5 | 340.0 | 714.6 | 27.5 GiB |
| TEEFHE | 0.50 | 6.81 | 4.25 | 240 MiB |

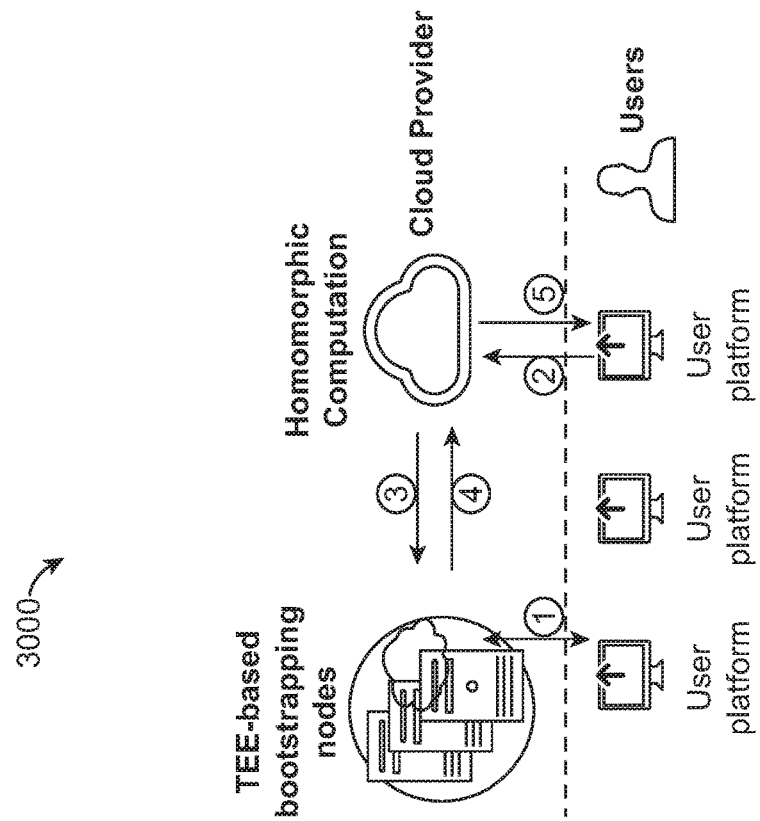

FIG. 30

Performance in terms of overall query processing time:

| # of SNPs | 500 SNPs | | | | | 1000 SNPs | | | | |
|---|---|---|---|---|---|---|---|---|---|---|
| Query size | 5 | 25 | 50 | 75 | 100 | 200 | 5 | 25 | 50 | 75 | 100 | 200 |
| HME computing | 1.085 | 0.059 | 0.061 | 0.059 | 0.061 | 0.041 | 2.114 | 1.461 | 1.321 | 1.233 | 1.211 | 0.903 |
| Enclave computing | 0.013 | 0.002 | 0.002 | 0.002 | 0.002 | 0.005 | 0.015 | 0.014 | 0.017 | 0.016 | 0.017 | 0.019 |
| Overall computing | 1.095 | 0.061 | 0.063 | 0.061 | 0.063 | 0.046 | 2.129 | 1.475 | 1.338 | 1.249 | 1.228 | 0.922 |

HyperRace: an LLVM-based tool to automatically protect a program from all Hyper-Threading side-channel attacks and other same-core side-channel attacks.

SYSTEM FOR DECENTRALIZED OWNERSHIP AND SECURE SHARING OF PERSONALIZED HEALTH DATA

CROSS-REFERENCE

This application is a continuation application of International Application No. PCT/CN2019/082539, filed on Apr. 12, 2019, which is incorporated herein by reference in its entirety.

BACKGROUND OF THE INVENTION

Medical information technology has progressed rapidly in the last few decades, but barriers to effective health data collection still exist. When additional data is required to perform medical research, healthcare providers, research laboratories, hospitals, and clinics must collect it from patients. These patients may not be willing to share their data, out of privacy concerns. The patients may not be affiliated with the entity requesting their data, requiring the entity to partner with other healthcare providers or facilities in order to collect the data securely.

SUMMARY OF THE INVENTION

In an aspect, a computer-implemented method is disclosed. The method comprises managing health information. The method includes obtaining health information associated with at least one data contributor, storing the health information in an encrypted format within a memory storage, utilizing a blockchain system to aid in managing the health information, and permitting a data miner to access and analyze the health information in the encrypted format.

In an aspect, a computer-implemented system for managing a health information system is disclosed. The system includes a memory storage configured to store health information associated with at least one data contributor in an encrypted format, a blockchain system configured to aid in managing the health information, and a portal configured to permit a data miner to access and analyze the health information in the encrypted format.

In an aspect, non-transitory computer-readable storage media are disclosed. The media are managing health information. The media comprise computer code for obtaining health information associated with at least one data contributor, computer code for storing the health information in an encrypted format within a memory storage, computer code for utilizing a blockchain system to aid in managing the health information, and computer code for permitting a data miner to access and analyze the health information in the encrypted format.

In one embodiment, the health information is genomic data.

In one embodiment, the genomic data comprises nucleic acid sequence information.

In one embodiment, the nucleic acid sequence information comprises DNA sequence information or RNA sequence information.

In one embodiment, the health information is associated with personal information about the at least one data contributor.

In one embodiment, the personal information comprises demographic information about the at least one data contributor.

In one embodiment, the demographic information comprises at least one or more of the following: age, ethnicity, gender, and race.

In one embodiment, the personal information comprises socioeconomic information about the at least one data contributor.

In one embodiment, the socioeconomic information comprises at least one or more of the following: education level, marital status, insurance status, occupation, and income.

In one embodiment, the health information comprises the at least one data contributor's medical history, wherein the medical history includes at least one of symptoms, diagnoses, procedures, and outcomes.

In one embodiment, the health information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the at least one data contributor may be able to opt out of selling data.

In one embodiment, the at least one data contributor is a health care provider.

In one embodiment, the at least one data contributor is a research institution.

In one embodiment, the method further comprises utilizing at least one selected encryption technique in managing the health information in the encrypted format within the memory storage.

In one embodiment, the encryption technique utilizes software guard extensions.

In one embodiment, the encryption technique utilizes homomorphic encryption.

In one embodiment, the encryption technique utilizes hybrid software guard extensions and homomorphic encryptions.

In one embodiment, the encryption techniques utilize secure multi-party computation.

In one embodiment, the memory storage comprises one or more decentralized storage nodes.

In one embodiment, health information from the decentralized storage nodes are accessed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed by one or more secure computing nodes.

In one embodiment, the data miner is a research institution or pharmaceutical company.

In one embodiment, the data miner is an insurance agency.

In one embodiment, the data miner is a philanthropy group, support group, health care provider, employer, educational institution, or matchmaker.

In one embodiment, the data miner makes a request for access to the health information.

In one embodiment, the request comprises one or more search parameters for the health information.

In one embodiment, a hash of the request for access forms a smart contract that is included in the blockchain system.

In one embodiment, the data miner is provided access to the health information of the at least one data contributor without being provided with access to personal information about the at least one data contributor.

In one embodiment, a query by the data miner to access and analyze the health information is protected through a privacy-preserving computation over encrypted data.

In one embodiment, the health information from the at least one data contributor is protected through privacy-preserving computation over encrypted data.

In one aspect, a computer implemented method of managing health information is disclosed. The method comprises obtaining health information associated with at least one data contributor, utilizing encryption to aid in storing the health information within a memory storage, utilizing a blockchain system to aid in managing the health information, and providing an incentive token to the at least one data contributor for the health information.

In an aspect, a computer-implemented system for managing health information system is disclosed. The system comprises a memory storage configured to store health information associated with at least one data contributor with aid of encryption, a blockchain system configured to aid in managing the health information, and one or more software modules configured to provide an incentive token to the at least one data contributor for the health information.

In an aspect, non-transitory computer-readable storage media are disclosed. The media are managing health information, the non-transitory computer readable media comprising computer code for obtaining health information associated with at least one data contributor, computer code for utilizing encryption to aid in storing the health information within a memory storage, computer code for utilizing a blockchain system to aid in managing the health information, and computer code for providing an incentive token to the at least one data contributor for the health information.

In one embodiment, the incentive token comprises at least one secure token.

In one embodiment, the incentive token is provided by a data miner to a token pool, and then transferred from the token pool to an account of the at least one data contributor.

In one embodiment, the secure token is identifiable by a unique public key address, wherein only the data contributor has access to the private key.

In one embodiment, the incentive token is provided in terms of a fair market value upon use of the health information for analysis.

In one embodiment, the incentive token is provided by a data miner provided with access to the health information associated with the at least one data contributor.

In one embodiment, the data miner provides incentive tokens to additional entities beyond the at least one data contributor when provided with access and analysis to the health information associated with the at least one data contributor.

In one embodiment, the health information is genomic data.

In one embodiment, the genomic data comprises nucleic acid sequence information.

In one embodiment, the nucleic acid sequence information comprises DNA sequence information or RNA sequence information.

In one embodiment, the health information is associated with personal information about the at least one data contributor.

In one embodiment, the personal information comprises demographic information about the at least one data contributor.

In one embodiment, the personal information comprises socioeconomic information about the at least one data contributor.

In one embodiment, the health information comprises the at least one data contributor's medical history, wherein the medical history includes at least one of symptoms, diagnoses, procedures, and outcomes.

In one embodiment, the health information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the at least one data contributor is a health care provider.

In one embodiment, the at least one data contributor is a research institution.

In one embodiment, the method further comprises utilizing at least one selected encryption technique in managing the health information in the encrypted format within the memory storage.

In one embodiment, the encryption technique utilizes software guard extensions.

In one embodiment, the encryption technique utilizes homomorphic encryption.

In one embodiment, the encryption technique utilizes hybrid software guard extensions and homomorphic encryptions.

In one embodiment, the encryption technique utilizes secure multi-party computation.

In one embodiment, the memory storage comprises one or more decentralized storage nodes.

In one embodiment, the encrypted health information from the decentralized storage nodes are accessed and analyzed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed and analyzed by one or more secure computing nodes.

In one embodiment, the data miner is a research institution or pharmaceutical company.

In one embodiment, the data miner is an insurance agency.

In one embodiment, the data miner is a philanthropy group, support group, health care provider, employer, educational institution, or matchmaker.

In one embodiment, the data miner makes a request for query and analysis to the health information.

In one embodiment, the request comprises one or more encrypted search parameters for the health information.

In one embodiment, a hash of the request for query and analysis forms a smart contract that is included in the blockchain system.

In one embodiment, the request for query and analysis from the data miner will be carried out over encrypted data through secure computing nodes.

In one embodiment, a query by the data miner to access and analyze the health information is protected through a privacy-preserving computation over encrypted data.

In one embodiment, the health information from the at least one data contributor is protected through privacy-preserving computation over encrypted data.

In one aspect, a computer implemented method of managing health information is disclosed. The method includes obtaining encrypted health information associated with at least one data contributor, utilizing encryption to aid in storing the health information within a memory storage, utilizing a blockchain system to aid in managing the health information, and receiving an incentive token from at least one data miner to access and analyze the encrypted health information.

In an aspect, a computer-implemented system for managing health information system is disclosed. The system comprises a memory storage configured to store health information associated with at least one data contributor with aid of encryption, a blockchain system configured to aid in managing the health information, and one or more software modules configured to receive an incentive token from the at least one data miner to access and analyze the encrypted health information.

In an aspect, non-transitory computer-readable storage media are disclosed. The media are managing health information, and comprise computer code for obtaining encrypted health information associated with at least one data contributor, computer code for utilizing encryption to aid in storing the health information within a memory storage, computer code for utilizing a blockchain system to aid in managing the health information, and computer code for receiving an incentive token from at least one data miner to access and analyze the encrypted health information.

In one embodiment, the incentive token comprises at least one secure token.

In one embodiment, at least a portion of the incentive token is provided to the at least one data contributor.

In one embodiment, at least a portion of the incentive token is provided to an entity providing or managing the memory storage.

In one embodiment, at least a portion of the incentive token is provided to an entity providing or managing the blockchain system.

In one embodiment, at least a portion of the incentive token is provided to an entity managing one or more portals through which the data miner may access and analyze the encrypted health information.

In one embodiment, at least a portion of the incentive token is provided to an entity managing one or more portals through which a data contributor may provide the health information.

In one embodiment, at least a portion of the incentive token is provided to an entity that sequences genomic data of the at least one data contributor, or an entity that verifies the sequenced genomic data.

In one embodiment, the health information is genomic data.

In one embodiment, the genomic data comprises nucleic acid sequence information.

In one embodiment, the nucleic acid sequence information comprises DNA sequence information or RNA sequence information.

In one embodiment, the health information is associated with personal information about the at least one data contributor.

In one embodiment, the personal information comprises demographic information about the at least one data contributor.

In one embodiment, the personal information comprises socioeconomic information about the at least one data contributor.

In one embodiment, the health information comprises the at least one data contributor's medical history, wherein the medical history includes at least one of symptoms, diagnoses, procedures, and outcomes.

In one embodiment, the health information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the at least one data contributor is a health care provider.

In one embodiment, the at least one data contributor is a research institution.

In one embodiment, the method further comprises utilizing at least one selected encryption technique in managing the health information in the encrypted format within the memory storage.

In one embodiment, the encryption technique utilizes software guard extensions.

In one embodiment, the encryption technique utilizes homomorphic encryption.

In one embodiment, the encryption technique utilizes hybrid software guard extensions and homomorphic encryptions.

In one embodiment, the encryption technique utilizes secure multi-party computation.

In one embodiment, the memory storage comprises one or more decentralized storage nodes.

In one embodiment, health information from the decentralized storage nodes are accessed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed by one or more secure computing nodes.

In one embodiment, the data miner is a research institution or pharmaceutical company.

In one embodiment, the data miner is an insurance agency.

In one embodiment, the data miner is a philanthropy group, support group, health care provider, employer, educational institution, or matchmaker.

In one embodiment, the data miner makes a request for access and analysis to the encrypted health information.

In one embodiment, the request comprises one or more search parameters for the health information.

In one embodiment, a hash of the request for access forms a smart contract that is included in the blockchain system.

In one embodiment, the request for query and analysis from the data miner will be carried out over encrypted data through secure computing nodes.

In one embodiment, a query by the data miner to access and analyze the health information is protected through a privacy-preserving computation over encrypted data.

In one embodiment, the health information from the at least one data contributor is protected through privacy-preserving computation over encrypted data.

In another aspect, a computer implemented method of managing health information is disclosed. The method comprises receiving one or more encrypted search parameters from a data miner to access, query and analyze encrypted health information associated with one or more data contributors, searching a memory storage for the encrypted health information that meets the one or more encrypted search parameters with encrypted outcomes, utilizing a blockchain system to aid in managing the health information, and providing an option for the data miner to access and analyze to the encrypted health information that meets the one or more search parameters through secure computing nodes.

In an aspect, a computer-implemented system for managing health information system is disclosed. The system includes one or more software modules configured to receive one or more search parameters from a data miner to access encrypted health information associated with one or more data contributors, a memory storage configured to store health information, a blockchain system configured to aid in managing the health information, and one or more software modules configured to (i) search the memory storage for the encrypted health information that meets the one or more search parameters and (ii) provide an option for the data miner to access and analyze the encrypted health information that meets the one or more search parameters through secure computing nodes.

In an aspect, non-transitory computer-readable storage media are disclosed. The media are managing health information, and comprise computer code for receiving one or more encrypted search parameters from a data miner to access and analyze encrypted health information associated with one or more data contributors, computer code for searching a memory storage for the encrypted health information that meets the one or more encrypted search parameters, computer code for utilizing a blockchain system to aid in managing the health information, and computer code for providing an option for the data miner to access and analyze to the encrypted health information that meets the one or more search parameters through secure computing nodes.

In one embodiment, the method further comprises displaying a quantification of the health information that meets the one or more search parameters.

In one embodiment, the quantification of the health information that meets the one or more search parameters comprises a number of individuals whose health information meets the one or more search parameters.

In one embodiment, the method includes receiving, from the data miner, an indication of a quantification of the health information that the data miner wishes to access.

In one embodiment, the quantification of the health information that the data miner wishes to access comprises a number of individuals whose health information the data miner wishes to access.

In one embodiment, the data miner is provided with access to only the number of individuals whose health information the data miner wishes to access.

In one embodiment, the data miner provides an incentive for the number of individuals whose health information the data miner wishes to access.

In one embodiment, the one or more search parameters comprises an amount of incentive that the data miner is willing to provide for the health information.

In one embodiment, the health information is stored in the memory storage in an encrypted format.

In one embodiment, the health information remains in the encrypted format while the searching for the health information that meets the one or more search parameters occurs.

In one embodiment, the health information is genomic data.

In one embodiment, the genomic data comprises nucleic acid sequence information.

In one embodiment, the nucleic acid sequence information comprises DNA sequence information or RNA sequence information.

In one embodiment, the health information is associated with personal information about the at least one data contributor.

In one embodiment, the personal information comprises demographic information about the at least one data contributor.

In one embodiment, the personal information comprises socioeconomic information about the at least one data contributor.

In one embodiment, the health information comprises the at least one data contributor's medical history, wherein the medical history includes at least one of symptoms, diagnoses, procedures, and outcomes.

In one embodiment, the health information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the at least one data contributor is a health care provider.

In one embodiment, the at least one data contributor is a research institution.

In one embodiment, the memory storage comprises one or more decentralized storage nodes.

In one embodiment, health information from the decentralized storage nodes are accessed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed by one or more secure computing nodes.

In one embodiment, the data miner is a research institution or pharmaceutical company.

In one embodiment, the data miner is an insurance agency.

In one embodiment, the data miner is a philanthropy group, support group, health care provider, employer, educational institution, or matchmaker.

In one embodiment, a hash of the request for access forms a smart contract that is included in the blockchain system.

In one embodiment, the request for query and analysis from the data miner will be carried out over encrypted data through secure computing nodes.

In one embodiment, a query by the data miner to access and analyze the health information is protected through a privacy-preserving computation over encrypted data.

In one embodiment, the health information from the at least one data contributor is protected through privacy-preserving computation over encrypted data.

In one aspect, computer implemented method of managing health information is disclosed. The method comprises obtaining health information associated with at least one data contributor, storing the encrypted health information within a memory storage, utilizing a blockchain system to aid in managing the health information, and receiving, from the at least one data contributor, an input that defines a threshold for a data miner to meet to access and analyze the encrypted health information through secure computing nodes.

In an aspect, a computer-implemented system for managing health information system, the system comprising a memory storage configured to store encrypted health information associated with at least one data contributor, a blockchain system configured to aid in managing the health information, and one or more software modules configured to receive, from the at least one data contributor, an input that defines a threshold for a data miner to meet to access and encrypted the health information through secure computing nodes.

In an aspect, non-transitory computer-readable storage media are disclosed. The media are managing health information. The media comprise computer code for obtaining encrypted health information associated with at least one data contributor, computer code for storing the encrypted health information within a memory storage, computer code for utilizing a blockchain system to aid in managing the health information, and computer code for receiving, from the at least one data contributor, an input that defines a threshold for a data miner to meet to access and encrypted the health information through secure computing nodes.

In one embodiment, the threshold for the data miner to meet comprises a minimum amount of incentive that the data miner would need to provide the at least one data contributor.

In one embodiment, the threshold for the data miner to meet comprises a characteristic of the data miner.

In one embodiment, the method further comprises displaying feedback on the threshold to the data contributor.

In one embodiment, the feedback comprises a likelihood that the data miner would meet the threshold.

In one embodiment, the feedback comprises a number of tokens to stake.

In one embodiment, the method further comprises options for the data contributor to provide access to personal information about the data contributor.

In one embodiment, the personal information comprises demographics information.

In one embodiment, the personal information comprises socioeconomic information.

In one embodiment, the personal information comprises health history.

In one embodiment, the health information comprises the at least one data contributor's medical history, wherein the medical history includes at least one of symptoms, diagnoses, procedures, and outcomes.

In one embodiment, the health information is stored in the memory storage in an encrypted format.

In one embodiment, the health information remains in the encrypted format while the data miner is accessing and analyzing the health information through secure computing nodes.

In one embodiment, the health information is genomic data.

In one embodiment, the genomic data comprises nucleic acid sequence information.

In one embodiment, the nucleic acid sequence information comprises DNA sequence information or RNA sequence information.

In one embodiment, the health information is associated with personal information about the at least one data contributor.

In one embodiment, the personal information comprises demographic information about the at least one data contributor.

In one embodiment, the personal information comprises socioeconomic information about the at least one data contributor.

In one embodiment, the health information comprises the at least one data contributor's medical history. In one embodiment, the medical history includes at least one of symptoms, diagnoses, procedures, and outcomes.

In one embodiment, the health information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the at least one data contributor is a health care provider.

In one embodiment, the at least one data contributor is a research institution.

In one embodiment, the memory storage comprises one or more decentralized storage nodes.

In one embodiment, health information from the decentralized storage nodes are accessed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed by one or more secure computing nodes.

In one embodiment, the data miner is a research institution or pharmaceutical company.

In one embodiment, the data miner is an insurance agency.

In one embodiment, the data miner is a philanthropy group, support group, health care provider, employer, educational institution, or matchmaker.

In one embodiment, the data miner makes a request for access to the health information.

In one embodiment, the request comprises one or more search parameters for the health information.

In one embodiment, a hash of the request for access forms a smart contract that is included in the blockchain system.

In one embodiment, the request for query and analysis from the data miner will be carried out over encrypted data through secure computing nodes.

In one embodiment, a query by the data miner to access and analyze the health information is protected through a privacy-preserving computation over encrypted data.

In one embodiment, the health information from the at least one data contributor is protected through privacy-preserving computation over encrypted data.

In an aspect, a computer-implemented method is disclosed. The method comprises managing health information. The method comprises obtaining encrypted health information associated with at least one data contributor, storing the encrypted health information within a memory storage, utilizing a blockchain system to aid in managing the health information, and permitting an insurance agency to access and analyze the health information to provide customized health coverage to the at least one data contributor through secure computing nodes.

In an aspect, a computer-implemented system for managing health information system is disclosed. The system comprises a memory storage configured to store encrypted health information associated with at least one data contributor in an encrypted format, a blockchain system configured to aid in managing the health information, and a portal configured to permit an insurance agency to access and analyze the encrypted health information to provide customized health coverage to the at least one data contributor through secure computing nodes.

In an aspect, non-transitory computer-readable storage media are disclosed. The media are managing health information. The non-transitory computer readable media comprise computer code for obtaining encrypted health information associated with at least one data contributor, computer code for storing the encrypted health information within a memory storage, computer code for utilizing a blockchain system to aid in managing the health information, and computer code for permitting an insurance agency to access and analyze the encrypted health information to provide customized health coverage to the at least one data contributor through secure computing nodes.

In one embodiment, the health information is stored in the memory storage in an encrypted format.

In one embodiment, the health information remains in the encrypted format while the insurance agency is accessing the health information.

In one embodiment, the encrypted health information accessed by the insurance agency is used to determine pricing for the customized health coverage.

In one embodiment, the health information is genomic data.

In one embodiment, the genomic data comprises nucleic acid sequence information.

In one embodiment, the nucleic acid sequence information comprises DNA sequence information or RNA sequence information.

In one embodiment, the health information is associated with personal information about the at least one data contributor.

In one embodiment, the personal information comprises demographic information about the at least one data contributor.

In one embodiment, the personal information comprises socioeconomic information about the at least one data contributor.

In one embodiment, the health information comprises the at least one data contributor's medical history, wherein the medical history includes at least one of symptoms, diagnoses, procedures, and outcomes.

In one embodiment, the health information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the memory storage comprises one or more decentralized storage nodes.

In one embodiment, health information from the decentralized storage nodes are accessed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed by one or more secure computing nodes.

In one embodiment, the insurance agency makes a request for access and analyze to the health information through secure computing nodes.

In one embodiment, the request comprises one or more encrypted search parameters for the health information.

In one embodiment, a hash of the request for access forms a smart contract that is included in the blockchain system.

In one embodiment, the request for query and analysis from the insurance agency will be carried out over encrypted data through secure computing nodes.

In one embodiment, a query by the data miner to access and analyze the health information is protected through a privacy-preserving computation over encrypted data.

In one embodiment, the health information from the at least one data contributor is protected through privacy-preserving computation over encrypted data.

In an aspect, a computer-implemented method is disclosed. The method comprises managing information. The method comprises obtaining information associated with at least one data contributor, storing the information in an encrypted format within a memory storage, utilizing a blockchain system to aid in managing the information, and permitting a data miner to access and analyze the information in the encrypted format while maintaining privacy of the at least one data contributor from the data miner.

In one embodiment, privacy of the at least one data contributor is maintained by preventing the data miner from accessing personal information about the data contributor in plaintext.

In one embodiment, privacy of the at least one data contributor is maintained by preventing the data miner from accessing an identity of the data contributor in plaintext.

In one embodiment, the information is genomic data.

In one embodiment, the genomic data comprises nucleic acid sequence information.

In one embodiment, the nucleic acid sequence information comprises DNA sequence information or RNA sequence information.

In one embodiment, the information is associated with personal information about the at least one data contributor.

In one embodiment, the personal information comprises demographic information about the at least one data contributor.

In one embodiment, the personal information comprises socioeconomic information about the at least one data contributor.

In one embodiment, the information comprises the at least one data contributor's medical history, wherein the medical history includes at least one of symptoms, diagnoses, procedures, and outcomes.

In one embodiment, the information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the memory storage comprises one or more decentralized storage nodes.

In one embodiment, information from the decentralized storage nodes are accessed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed by one or more secure computing nodes.

In one embodiment, the data miner makes a request for access and analysis to the information through secure computing nodes.

In one embodiment, the request comprises one or more encrypted search parameters for the information.

In one embodiment, a hash of the request for access forms a smart contract that is included in the blockchain system.

In one embodiment, the request for query and analysis from the data miner will be carried out over encrypted data through secure computing nodes.

In an aspect, a computer-implemented method is disclosed. The method comprises managing analysis applications. The method comprises providing a plurality of data analysis applications that are configured to access and analyze information in associated with at least one data contributor, wherein the information is stored in an encrypted format within a memory storage and a blockchain system aids in managing the information, and accepting a selection of at least one data analysis application from the plurality of data analysis applications to access and analyze the information.

In one embodiment, the selection is provided by a data miner.

In one embodiment, the selection of the at least one data analysis application comprises a selection for purchase of the data analysis application.

In one embodiment, the plurality of data analysis applications analyze different aspects of the information.

In one embodiment, the plurality of data analysis applications provide calculations of the information.

In one embodiment, the information is genomic data.

In one embodiment, the genomic data comprises nucleic acid sequence information.

In one embodiment, the nucleic acid sequence information comprises DNA sequence information or RNA sequence information.

In one embodiment, the information is associated with personal information about the at least one data contributor.

In one embodiment, the personal information comprises demographic information about the at least one data contributor.

In one embodiment, the personal information comprises socioeconomic information about the at least one data contributor.

In one embodiment, the information comprises the at least one data contributor's medical history, wherein the medical history includes at least one of symptoms, diagnoses, procedures, and outcomes.

In one embodiment, the information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the memory storage comprises one or more decentralized storage nodes.

In one embodiment, information from the decentralized storage nodes are accessed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed by one or more secure computing nodes.

In one embodiment, the selected data analysis application makes a request for access and analysis to the information through secure computing nodes.

In one embodiment, the request comprises one or more encrypted search parameters for the information.

In one embodiment, a hash of the request for access forms a smart contract that is included in the blockchain system.

In one embodiment, the request for query and analysis from the selected data analysis application will be carried out over encrypted data through secure computing nodes.

In one embodiment, the results from the selected data analysis application are protected with optimized perturbation methods for privacy-preserving results dissemination.

In an aspect, a computer-implemented method is disclosed. The method comprises managing analysis applications. The method comprises managing a plurality of encryption keys, each associated with at least one data contributor that provides information, selecting, with aid of a processor, an encryption key from the plurality of encryption keys, based on the at least one data contributor providing information, and utilizing the selected encryption key to store the information in an encrypted format within a memory storage, wherein a blockchain system aids in managing the information.

In one embodiment, each data contributor has multiple encryption keys for information encryption.

In one embodiment, the encryption key can be used to assist the privacy-preserving computation over encrypted data.

In one embodiment, the data contributor is able to create, manage, store, distribute and revoke the encryption key.

In one embodiment, each data miner capable of accessing and analyzing the information has multiple encryption keys for information encryption.

In one embodiment, the encryption key can be used to return encrypted analysis results from the privacy-preserving computation over encrypted data.

In one embodiment, the data miner is able to create, manage, store, distribute and revoke the encryption key.

In one embodiment, the information is genomic data.

In one embodiment, the genomic data comprises nucleic acid sequence information.

In one embodiment, the nucleic acid sequence information comprises DNA sequence information or RNA sequence information.

In one embodiment, the information is associated with personal information about the at least one data contributor.

In one embodiment, the personal information comprises demographic information about the at least one data contributor.

In one embodiment, the personal information comprises socioeconomic information about the at least one data contributor.

In one embodiment, the information comprises the at least one data contributor's medical history. In one embodiment, the medical history includes at least one of symptoms, diagnoses, procedures, and outcomes.

In one embodiment, the information is analysis results about the at least one data contributor.

In one embodiment, the information has been verified by a third party.

In one embodiment, the third party has provided a signature, which allows the data to be included in the blockchain system.

In one embodiment, a hash of the data forms a smart contract that is included in the blockchain system.

In one embodiment, the at least one data contributor is an individual.

In one embodiment, the memory storage comprises one or more decentralized storage nodes.

In one embodiment, information from the decentralized storage nodes are accessed by one or more secure computing nodes.

In one embodiment, a hash of results as part of a task retrieval by the secure computing nodes forms a smart contract that is included in the blockchain system.

In one embodiment, the data remains in the encrypted format when the decentralized storage nodes are accessed by one or more secure computing nodes.

In one embodiment, the data miner makes a request for access and analyze to the information through secure computing nodes.

In one embodiment, the request comprises one or more encrypted search parameters for the information.

In one embodiment, a hash of the request for access forms a smart contract that is included in the blockchain system.

In one embodiment, the request for query and analysis from the data miner will be carried out over encrypted data through secure computing nodes.

In an aspect, a computer-implemented method is disclosed. The method comprises managing health information. The method comprises obtaining health information from a plurality of data contributors, storing the health information in an encrypted format within a memory storage, utilizing a blockchain system to aid in managing the health information, and creating a federated learning model using model parameters or intermediary analysis statistics with the assistance of a privacy-preserving computing node.

In one embodiment, the data contributors do not share raw data in the federated learning model.

In one embodiment, exchange of the model parameters or the intermediary analysis statistics are protected through privacy-preserving computation over encrypted data.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 13 shows an illustration of horizontally distributed data;

FIG. 14 shows an illustration of vertically distributed data;

FIG. 21 shows the average computing time for training the regression models of FIGS. 15, 16, 17, 18, and 20;

FIG. 30 shows a performance evaluation using a hybrid secure solution that combines a trusted execution environment (TEE) system and a homomorphic computation system;

DETAILED DESCRIPTION OF THE INVENTION

Figure 1:
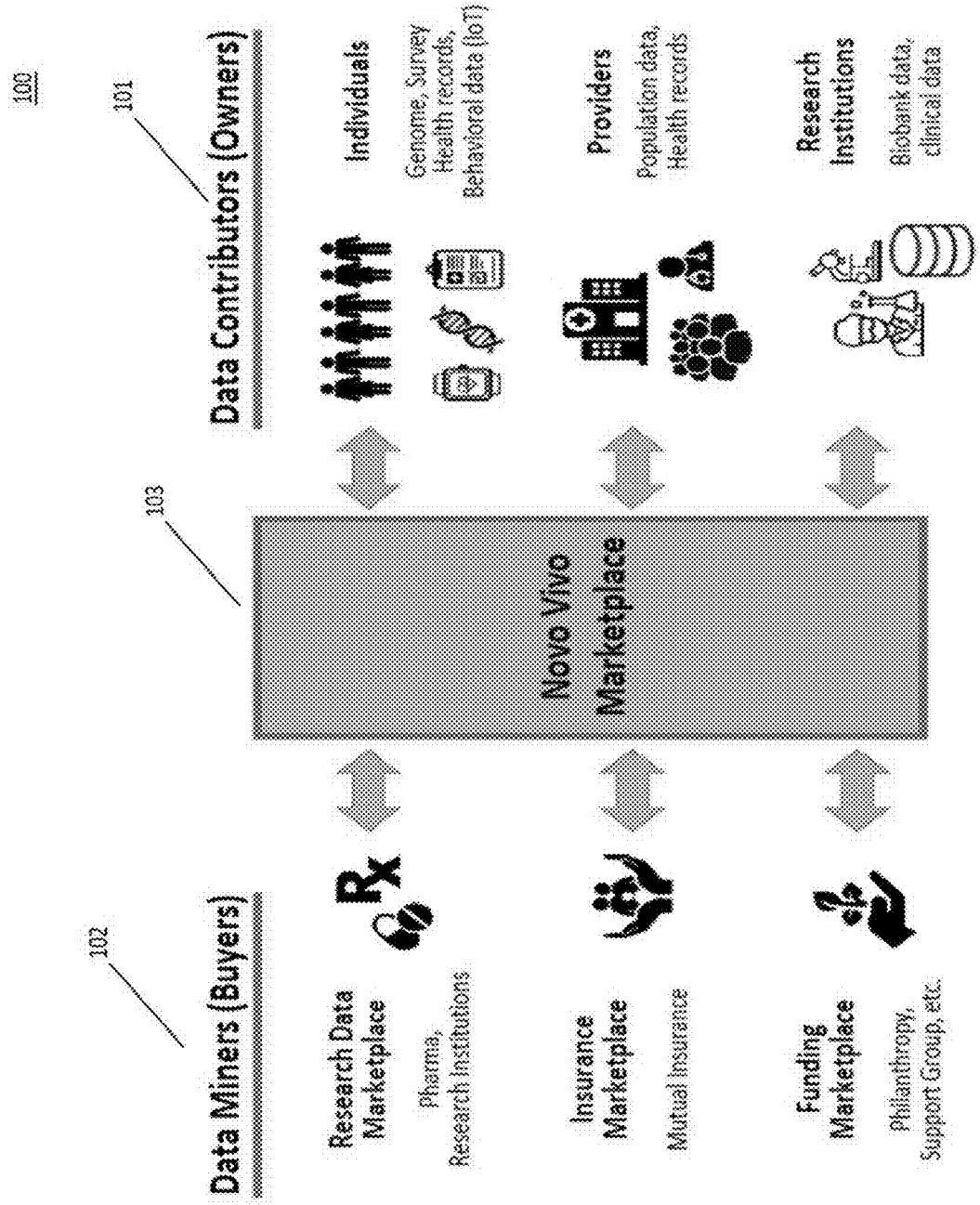
FIG. 1 shows an example of a system comprising one or more data contributors and one or more data miners.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention provides systems and methods for decentralized ownership and secure sharing of personalized data. Various aspects of the invention described herein may be applied to any of the particular applications set forth below. The invention may be applied as a standalone health data system or as a component of an integrated data sharing and analysis system. It shall be understood that different aspects of the invention can be appreciated individually, collectively or in combination with each other.

The system disclosed implements a secure method for facilitating secure exchange of health information among various stakeholders, including data owners or contributors, data requestors or miners, and medical providers, including hospitals, clinics, and research laboratories. Additional aspects of the system provide means for conducting secure research on health data collected from data contributors. Health information is exchanged using a decentralized system that incentivizes data contributors to provide health data to data miners.

The data miners, which may be pharmaceutical companies, medical laboratories, or hospitals, use various methods in order to perform research on aggregated contributor data, while maintaining contributor privacy. Individual methods are explained in greater detail in this disclosure. Many of these methods use software guard extensions (SGX), which provide computing functions to analyze data stored in protected enclaves within computer memory. These functions include encryption, decryption, hashing, and secure data analysis using, for example, statistical methods or machine learning algorithms. Analysis may be performed using a distributed system, in which multiple nodes perform local data analysis and share results securely. Analysis may also be performed using a federated system, in which a central node aggregates local analysis results from a plurality of nodes and produces an aggregated output, while preserving data security for the local nodes. Encrypting the data accessed by system stakeholders encourages contributors to share sensitive data, giving researchers more available information to analyze, for example, as features for a deep neural network. In addition, this method of data sharing can be implemented between jurisdictions that have varying privacy regulations, and may not normally be able to share data legally.

Blockchain and smart contracts enable the system to allow data contributors to share their data while maintaining ownership of the data and preserving privacy. Data contributors use smart contracts to change sharing policies, for example, to enable or disable sharing of specific data. Data miners use contacts to request data from contributors, as well as to securely request analysis tasks from computing nodes. Blockchain is also used to disburse rewards to data contributors. When data miners request data analysis tasks, they send encrypted requests to computing nodes using smart contracts. In the smart contract is a number of tokens. Computing nodes compete in an auction to perform the task and retrieve the tokens, which are released to the data contributors. Tokens may be used to pay for healthcare services, for example, annual checkups.

System

FIG. 1 shows an example of a system 100 comprising one or more data contributors 101 and one or more data miners 102. The one or more data contributors and/or data miners may interact over a marketplace 103.

Data contributors 101 may provide information. The information may be accessible via a marketplace 103. Data contributors may include any party that can provide information for the market place. The information may include health related information.

Data contributors 101 may include individuals, providers, research institutions or any other entities. Examples of individual data contributors may include any human, animal, or other living being that may provide information. For example, individuals may provide genomic information, health records, survey responses, behavioral data, or any other information. Information may include information provided with aid of a biological sample (e.g., blood, serum, plasma, tissue, sputum, urine, stool, perspiration, hair, saliva, nasal swab or nasopharyngeal wash, tears, gastric fluid, spinal fluid, mucus, earwax, oil, glandular secretion, cerebral spinal fluid, semen, and vaginal fluid, throat swab, breath, finger nails, skin, biopsy, placental fluid, amniotic fluid, cord blood, emphatic fluids, cavity fluids, pus, microbiota, meconium, breast milk and/or other excretions). Information may include physiological information that may be measured with aid of one or more instruments (e.g., EEG, MRI, ultrasound scanner, scales, thermometers, pulse oximeter, blood pressure cuff, etc.). Information may be measured with aid of one or more tests, such as testing utilizing ultrasound, echocardiography, magnetic resonance imaging (MRI), x-ray computed tomography (CT), and nuclear medicine scanners (e.g. single photon emission computed tomography (SPECT) and positron emission tomography (PET) with and without CT). Information may be gathered with respect to an individual's electrical activity (e.g., electrocardiogram of heart), blood pressure (e.g., ankle brachial pressure index), air flow (e.g., pulmonary function testing), or other conditions. The information may include data collected with aid of one or more wearable device, such as behavioral data collected by Internet-of-Things (IOT) devices. The information may be actively collected at one or more points of time, or may be passively collected continuously or periodically.

In another example, providers may provide information. For instance, population data, health records, and so forth may be provided. The providers may be health care providers, such as hospitals, clinics, medical offices, pharmacies, or medical laboratories. The information may include medical records of individuals or groups of populations. The information provided may be HIPAA compliant.

The providers may include research institutions. Information may include biobank data, clinical data, or any other type of information. Research institutions may include institutions associated with health care providers, with educational institutions, with pharmaceutical or other companies, or any other entity that may collect and/or analyze data, such as health-related data.

The information provided by data contributors may include health related information. Health related information may include genetic data, medical data (electronic and/or paper health records), fitness data, or any other data.

The health related information may include omics data (e.g. genomics, transcriptomics, proteomics, metabolomics, epigenetics, or microbiomics). The omics data may include nucleic acid data, such as DNA data and/or RNA data, epigenetic data, or any other type of omics data. The genomic data may include nucleic acid sequence information. In some embodiments, the nucleic acid sequence information may comprise DNA sequence information or RNA sequence information. Nucleic acid data may include sequence data, methylation data, expression data, or any other data. DNA sequence data may include whole genome sequence data, partial genome sequence data (e.g., sequence data for one or more genes), whole exome sequence data, partial exome sequence data, or any other type of sequence data. The information may include nucleic acid sequence mutation or variant data. Such data may be derived from comparing an individual nucleic acid sequence with one or more reference genomes. The mutation or variant data may include data on substitutions (including point mutations and/or single-nucleotide polymorphisms (SNPs)), insertions, deletions, missense mutations, nonsense mutations, repeat expansions, and/or frameshifts in one or more genes. In some embodiments, the information may include a genotype based on SNPs present in one or more genes of an individual.

The health related information may include medical records or may utilize medical records. Medical records may include electronic health records (EHRs), personal health records (PHRs) or any other type of medical record. An EHR may include a collection of electronic health information about an individual or population. An EHR may include records of therapies, prescriptions, summaries, orders, or instructions issued by a healthcare provider for an individual. An EHR may include information such as genomic data, metabolomic data, proteomic data, microbiomic data, medical history, medication record, medication history, physical exam, lab test reports (e.g., pathology report, blood cell count report, blood culture report, urinalysis report, throat culture report, genetic test report, etc.) imaging reports (e.g., X-ray, CT scan, MRI, ultrasound, etc.), demographics, family history, allergies, adverse drug reactions, illnesses, chronic diseases, hospitalizations, surgeries, immunization status, vital signs, biometrics (e.g., heart rate, body temperature, blood pressure, respiratory rate, blood diagnostics such as oxygen saturation, glucose concentration, blood count, urine diagnostics such as specific gravity, protein, glucose, and blood, other bodily fluid diagnostics, imaging, etc.), age, weight, height, or other information. An EHR may be maintained by an institution. A PHR may include a collection of health in formation maintained by an individual. PHRs may include any information that may be maintained by an EHR. Inn some instance, a PHR may include information pertaining to immunizations, allergies, adverse drug reactions, chronic diseases, family history, illness, hospitalization, imaging reports, lab test results, medications and dosing, prescription record, procedures (e.g., surgeries), daily living details, activity logs, exercise records, sleep logs, nutrition records, or any other information.

The information may include fitness data. For example, the information may include physiological data (e.g., blood pressure measurements, heart rate measurements (e.g., average heart rate, maximum heart rate), respiration rate, $VO_2$, or any other physiological information such as information described elsewhere herein), or exercise data (e.g., duration and frequency of exercise, type of exercise performed, and metrics regarding specific exercises performed). The fitness data can be collected in any manner. For instance, a user may enter the fitness information into an application, such as a web or mobile application. Fitness data may also be collected with aid of an IOT device, such as a wearable device. Examples of wearable devices may include, but are not limited to Fitbits, Apple watch, Garmin, and so forth. In some instances, sources of fitness information may be linked or communicating with one another. For instance, a fitness log, tracking application, or device may be accessible to obtain and/or share fitness data.

In some embodiments, health information may be associated with personal information about at least one data contributor. The personal information about the data contributor may include demographic information about at least one data contributor, such as age, gender, ethnicity, race, nationality, and income. The personal information may also comprise socioeconomic information about the data contributor. Personal information may be related to an individual's habits (e.g., lifestyle habits, purchase habits, search habits, travel history, fitness habits, etc.). This information may include one or more of the following: education level, marital status, insurance status, occupation, and income. Personal information may include an individual's contact information (e.g., address, phone number, email), account information, identification information (e.g., driver's license ID information, passport information, birth date, social security number, etc.).

Figure 2:
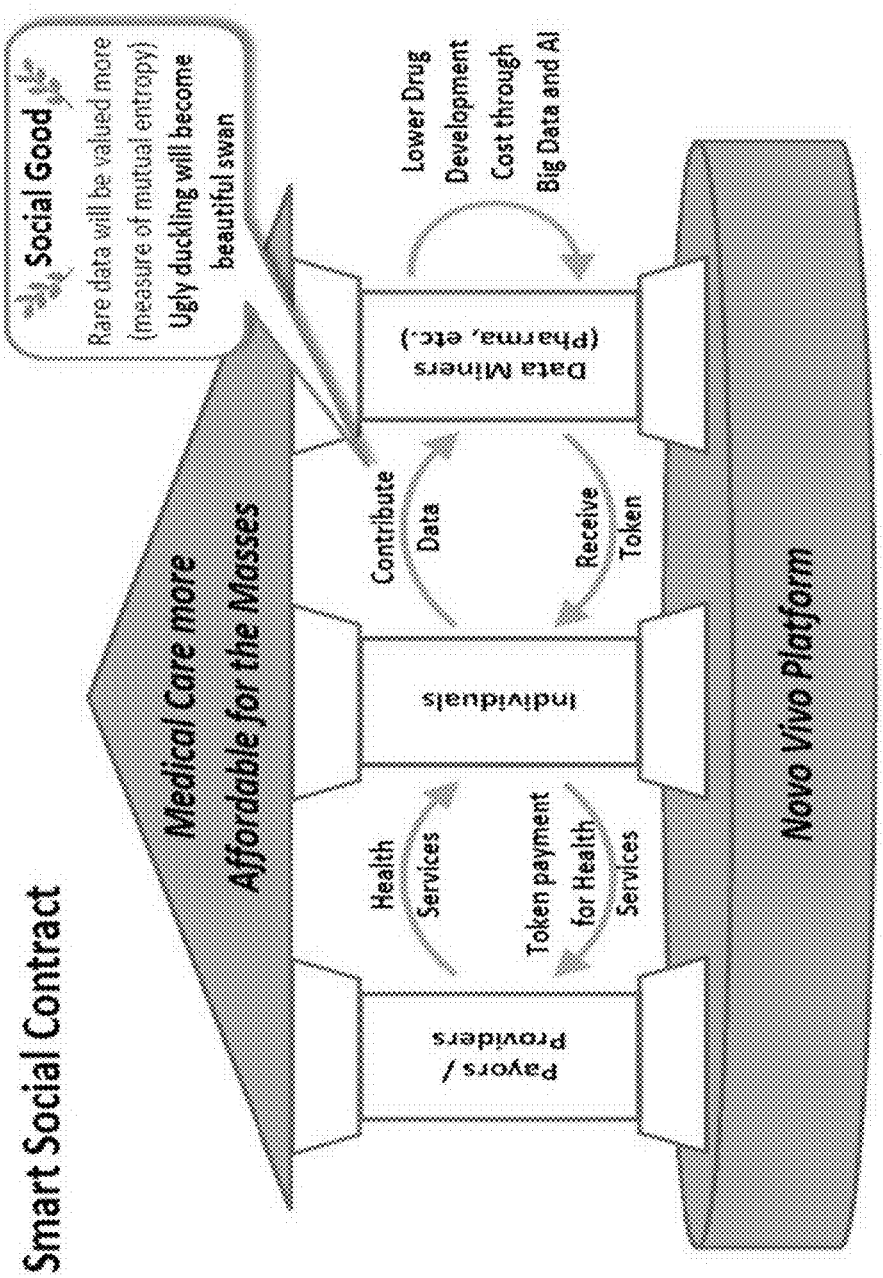
FIG. 2 illustrates a workflow for incentivizing data contributors to provide data to health providers.

FIG. 2 illustrates a workflow 200 for incentivizing data contributors to provide data to health providers. Health providers offer health services to data contributors, whom securely contribute their private data to data miners in exchange for incentive tokens. Data contributed may include genomic data. The data may be encrypted in order to prevent compromise of any individual's private health data. Upon receipt of the contributor data, data miners may issue incentive tokens, enabling the contributors to purchase health goods and services.

The systems and methods provided herein may advantageously provide rewards to data contributors, such as individuals, for providing data. Similarly, data miners may benefit from the data received from the data contributors.

As data contributors provide data, they may be rewarded with tokens. The tokens may benefit the data contributors by allowing them to make purchases. In some instances, the tokens may be used to purchase any goods or services that may accept the tokens. In some instances, the tokens may be used to purchase health services. This may advantageously allow data contributors to use health related information to improve or maintain the data contributor's own health. Alternatively, the data contributors may use the tokens to purchase other goods or services.

The data miners may beneficially be provided with access to a larger data pool. As more data contributors are incentivized to provide data, data miners may have easier access to data from certain desirable groups. For example, a pharmaceutical company that is trying to develop a drug for a particular type of disease may be given access to a larger pool of people who have the disease or at risk for the disease. In some instances, having access to a larger data pool allows more rare types of data to become available. By providing the tokens, the data miners are able to access data that they may not otherwise be able to access. This may allow the data miners to have lower development costs. For instance, drug developers would have lower drug development costs through big data and artificial intelligence (AI).

In one example, rare data may be valued more. For instance, a data contributor with a unique set of genetic conditions, or related health conditions may provide more rare data that will be more valuable to data miners. More rare data may be rewarded by providing more tokens or incentives to the data contributor to provide the data.

Payers and providers may benefit from the systems and methods provided herein. For example, health care providers may be able to reach a larger population than they previously may have been able to reach. The health care providers may receive tokens as payment for health services and provide health services to individuals in turn. Utilizing the marketplace and accepting the tokens may allow health care providers to treat individuals that they may not otherwise have treated. Data providers such as hospitals and research institutions may convert the tokens to cash in order to finance operations, fund new research endeavors, hire personnel (e.g., medical practitioners and scientists), purchase equipment, or donate to charity.

Figure 3:
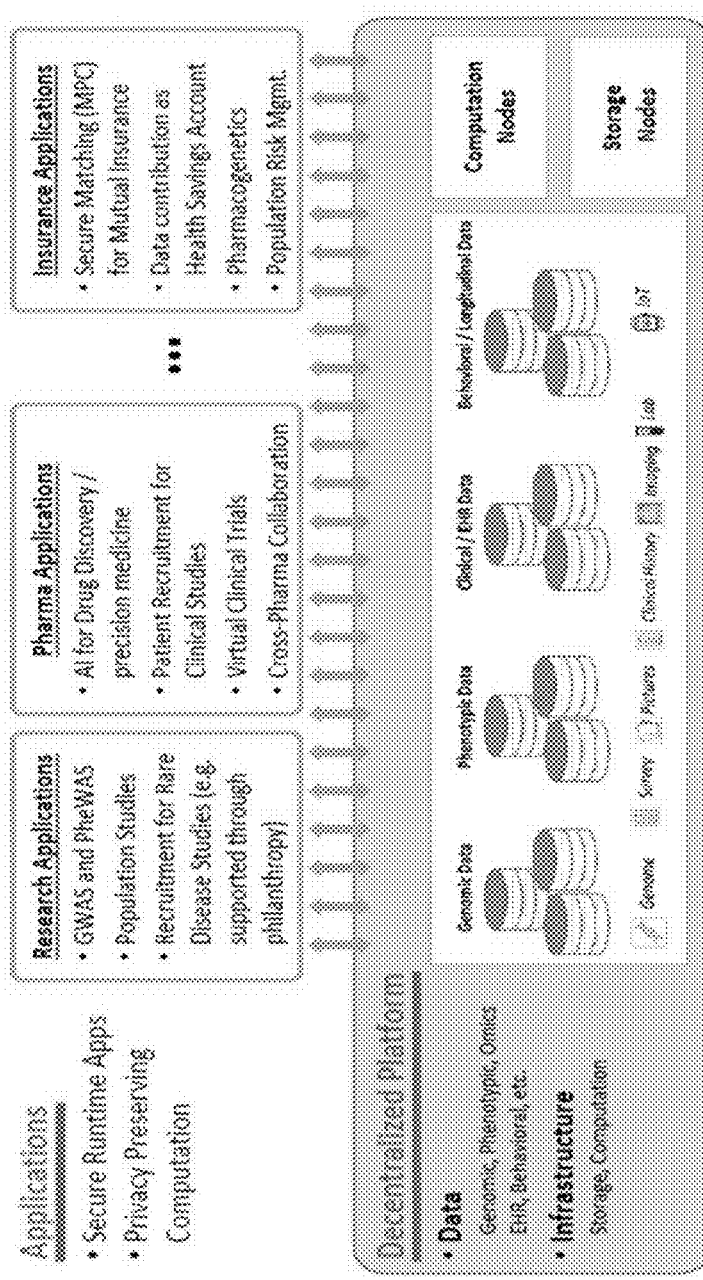
FIG. 3 illustrates how the system may be used for many different applications.

FIG. 3 illustrates 300 system uses for many different applications. These applications may include research applications, pharma applications, and insurance applications. Any applications that may benefit from utilizing secured health-related data from data contributors may be used. For instance, further applications may include, but are not limited to, health care applications, employment applications, educational applications, matchmaking/dating applications, veterinary applications, fitness/sports applications, family planning applications, policy applications, business and marketing applications, or any other applications.

The system may perform data analysis tasks including genome-wide association studies (GWAS), phenome-wide associative studies (PheWAS), population genetic studies, AI for drug discovery, similar patient identification, cross-pharma collaboration, and/or population risk management. For example, the system may be used in research applications, such as the GWAS and PheWAS to see if genomes or phenomes are associated with any variations or traits. This may advantageously create associations which may be useful for determining trends and/or aiding in treatment or support for various populations and individuals. This may also aid in resource allocation and predictive studies. The system may be used for population studies. The data gathered may be useful in helping shape the understanding of many areas, such as population dynamics, fertility and family dynamics, health, aging, mortality, human capital and/or labor markets. The systems and methods provided herein may aid in recruitment for rare disease studies. The pool of data contributors may provide access to individuals with rare diseases, which may otherwise not be available. Such individuals may be incentivized to provide their data with larger rewards (e.g., numbers of tokens). In some instances, the rare disease studies may be supported through pharmaceutical companies, research institutions, or philanthropy.

In another example, the system may be used for pharma applications. For instance, the data collected and analyzed may be used for drug discovery and/or precision medicine. In some instances, AI may be employed to aid in the drug discovery and/or precision medicine. Machine learning techniques may be able to access the large pools of data obtained and analyze the information for pharmaceutical applications. The systems and methods provided herein may aid in patient recruitment for clinical studies. The systems and methods may identify data from particular data contributors that may indicate that the data contributors would be good candidates for a particular study. For example, if a data miner is interested in attempting a clinical trial for a drug to treat a particular disease, data contributors suffering from a particular stage of the disease may be identified and may be offered a chance to participate in the clinical trial. Similarly, a preventive drug may be undergoing a clinical trial, and data contributors who are at risk for the associated disease but not yet diagnosed with the disease may be identified to participate in the trial for the preventative drug. Data contributors who have genetic characteristics that may indicate that they are likely to benefit the most from particular drugs may be invited to participate in the clinical trial. This may also benefit the data contributors since they may be made aware of opportunities to participate in trials that they may not otherwise have been exposed to.

Similarly, virtual clinical trials may advantageously employ the systems and methods provided herein. Virtual trials allow patients to participate in clinical trials remotely, without having to visit a medical research facility. For example, a patient testing a skin treatment may be directed to apply the treatment in his or her home over a period of a few weeks and take daily pictures of the treated area. The participant would then send these pictures to a processing facility over a network for analysis. In this virtual clinical trial, one or more patients are the one or more data contributors. Data miners may be affiliated with the medical research facility administering the trial, and may have issued smart contracts requesting results from the treatment performed. Following this, data miners may compensate the data contributors with tokens.

Cross-pharma collaboration may also advantageously employ the systems and methods provided herein. Pharmaceutical companies face high costs when compounds they develop fail (e.g., they are toxic to humans or other animals). In order to improve success rates, many pharmaceutical companies share resources and allow drug developers and researchers, either independent or from competing companies, to test their compounds and reduce failure rates. Using the system disclosed, data miners, as representatives from companies, may request data from competing companies or independent researchers, and use that data to develop new drugs that are more likely to be successful (e.g., less likely to be toxic). Contributing companies can choose which data they wish to keep private and which data they wish to share. Such a procedure may be mutually beneficial to many companies, as they all may wish to reduce failure rates and, thus, reduce costs.

The system disclosed may also allow data contributors to manage their own mutual insurance plans using a genetic profile. A contributor may map his or her plan to his or her genetic profile, and may view plan information securely by authenticating with a digital signature. The user may be able to manage his or her health data to make configuring his or her plan easier. Insurance companies may also serve as data miners to request insurance or health information from contributors by accessing data from their genetic profiles. In addition, secure computation can also be used by mutual insurance companies to access more personal health records, through which the risks of different diseases can predicted in a more accurate way to support decision making for mutual insurance companies.

A contributor may also be able to use earnings from sharing data in a health savings account (HSA). For example, the contributor may convert earned incentive tokens into cash and transfer the cash to an HSA, where it may remain untaxed. To promote HSA use, the system may offer contributors additional tokens for their data, with the stipulation that these tokens only be used when their values are transferred to the contributors' HSAs.

The system may also be used to aid pharmacogenetic researchers study how drugs affect patients with varied metabolic pathways. Researchers may obtain data from studies of drugs on diverse populations, and aggregate results from these studies to better understand how drugs may affect people with genetic differences. Aggregated data from these studies may be given to insurance companies, which may use the information to affect the premiums they charge customers.

The system may also be used for population risk management. Using the large amount of data processed by the system, research can analyze morbidity patterns among large groups of people in order to determine how to manage disease prevalence and widespread poor health outcomes. Researchers and medical professionals can consolidate patient information, develop cost metrics, create practice guidelines, and track aggregated health outcomes. These practices may also improve pricing by giving medical professionals, insurance providers, and contributors alike more information on how different conditions affect diverse populations and what practices are being put into place to improve health outcomes.

The systems and methods provided herein may be employed for veterinary applications. For examples, pets or other animals may contribute data to the systems and methods provided herein. This may be useful for breeding purposes. For example, for breeding programs for endangered animals, it may be possible to identify potential mates that provide the best chance of breeding success and survival. In another example, for animals with desired traits (e.g., speed in racehorses), the data may be useful for pairing animals that would result in a higher likelihood of offspring with the desired traits. The data may also be useful for maintaining the health of animals. For example, if a pet has a disease, the data may be useful in determining a treatment plan for the pet, such as particular drugs, clinical trials, or lifestyle modifications. The data may also help an individual plan for a care of a pet or other animal. For instance, if the pet is at a high risk for developing epilepsy, the owner can become informed ahead of time, and prepare resource allocation as needed.

The system may be used in educational applications. For example, a student contributor's genetic profile may be viewed to determine whether or not the student has special needs. Data miners, who may be affiliated with educational institutions, may request studies to be performed on data from student contributor profiles, for example, to determine which special education initiatives or programs produce the best results in teaching special-needs children. The system may also be used to determine whether or not aspects of a student contributor's medical history affect his or her performance, by allowing data miners to request research on health factors and educational attainment.

The system may be used in matchmaking/dating applications. For example, a contributor may wish to list dating profile information in his or her genetic profile. Data miners may run queries to find an aggregation of similar profiles of users. Then, a matchmaking program may be used to pair contributors together. Contributors may exchange information and communicate preferences securely using smart contracts.

The system may be used in fitness or sports applications. For example, a data miner interested in creating exercise plans for contributors may request studies relating specific genetic or medical factors to athletic performance. These studies may be used to devise personalized exercise plans for contributors exhibiting particular physical characteristics. The studies may also be used to determine personalized diet plans for individuals, based on their genetic and medical histories.

The system may also be used for family planning applications. For example, prospective parents may wish to know whether their future children may be at risk for genetic diseases or conditions. Data miners may request studies to be performed on prospective parents with particular genetic or medical characteristics, in order to determine whether having the particular characteristics correlates with passing on genetic conditions to children. One such example of this test is the transmission disequilibrium test (TDT), described further in this disclosure.

The system may have applications in health policy. Because large amounts of genetic data can be procured by data miners, it is possible for the miners to conduct many types of studies on the prevalence of health conditions with respect to specific sub-populations of data contributors within the system. This information may be given to policymakers, who may draft legislation to correct undesirable health outcomes affecting particular sub-populations with particular common characteristics.

The system may have business or marketing applications, with respect to the marketing of health care products. Populations of data contributors may be segmented based on one or more common health attributes. These segmented populations may be targeted by marketers as prospective buyers of their products. Data miners may request studies of effects of target advertisements to these groups, such as studies performed by conducting focus groups.

The system supports these data mining methods on different types of data such as genomic data, survey data, clinical/EHR data, and behavioral/longitudinal data. Such data may be stored and accessible in any manner. For example, the data may be stored in individual databases based on the data type (e.g., genomic data database, phenotypic data database, clinical/EHR data database, behavioral/longitudinal data database, etc.). In another example, the data may be stored and/or organized by data contributor or data characteristics (e.g., demographics of the data contributor, health conditions or traits associates with the data contributors, etc.). The data may be associated with the data contributor, even if stored separately. Personal data about the data contributor may be stored separately from the health data, or may be stored with the health data. The personal data may or may not be associated with the health data of the contributor. In some instances, the data may be stored in a manner that will preserve the privacy of the data contributor. Any type of data source may be utilized in gathering the information about the data contributors. For instance, genomic studies (e.g., DNA testing services such as 23andme, Ancestry, services offered through health care facilities, services offered through laboratories, etc.) may be a data source from which the health information is derived, or that is included in the health information. In another example, survey information may be utilized. For instance, a data contributor may fill out one or more surveys from which the health information is derived, or that is included in the health information. Pictures may be utilized. The pictures may be voluntarily contributed by the data contributor, a health care service of the data contributor, or may be collected from a third party source (e.g., a public third party source, such as the Internet). In some instances, clinical history of the data contributor may be provided. The data contributor may voluntarily enter the clinical history, or may provide the clinical history through his or her EHR. The clinical history may be used to derive the health information or may be included in the health information. Images, such as medical images may be a source of health information as well. For example, X-rays, ultrasounds, MRIs, CAT scans, PET scans, or any other types of images may be used to derive the health information or may be included in the health information. Similarly, laboratory data may be used as a data source. For instance, results of blood tests, urine samples, stool samples, cheek swabs, tear samples, tissue analysis, or analysis of any type of biological sample may be used to derive the health information or may be included in the health information. IOT devices may also be a source of data. For example, information from wearable devices (e.g., heart rate, oxygen level, respiratory rate, activity level, movement, location changes, images, sounds, touch-impedance measurements, etc.) may be used to derive the health information or may be included in the health information. The system has a secure application, in which different researchers or institutions can also contribute different data analysis applications with the incentives to receive rewards from data miners.

Data analysis tasks may be performed using machine learning algorithms and statistical methods. For example, data contributors may send encrypted data packages to computing nodes containing secure enclaves. The data contributors and computing nodes may use remote attestation to authenticate one another and exchange cryptographic keys. The secure computing nodes may aggregate data from many contributors in order to perform analysis on large data sets. A set of contributor data may be anonymized using pseudonyms or encryption techniques. Anonymous patients may be related to other patients using unique feature sets. Data may be analyzed from many different patients across jurisdictions. Massive data sets may enhance drug discovery techniques that use artificial intelligence, as access to properties large numbers of biological compounds becomes available through the platform. Results from data analysis applications may be protected with optimized perturbation methods for privacy-preserving dissemination.

In the listed applications, secure computing nodes perform analysis on data of many different types. Data types include genomic data, phenotypic data, clinical/human resources data, and behavioral/longitudinal data. Secure computing nodes may perform machine learning analysis or statistical analysis. Different types of analysis may include support vector machines, decision tree based analyses, logistic regressions, hidden Markov models, and neural networks, including, without limitation, convolutional neural networks (CNNs) and recurrent neural networks (RNNs). Secure storage nodes store data retrieved from data contributors and provide data to the secure computing nodes for analysis. Key management nodes allow data contributors to protect privacy, by only allowing access to stakeholders after the contributors provide the stakeholders with their public keys. Secure applications match data miners with contributor data that the miners request in order to carry out analysis tasks.

In addition to performing research, the system may also be used by contributors to purchase health insurance. The details of a contributor's policy may get linked to his or her corresponding profile within the blockchain. When a contributor undergoes a medical procedure covered by his or her policy, a smart contract may automatically be triggered and the correct payment from the insurance company to the hospital may be made. This may reduce inefficiencies and stresses that come with having to complete insurance claims forms.

Data miners may access and/or analyze the data through the systems and methods provided herein. In some instances, data miners may receive raw data and perform selected analysis of the raw data. In some instances, the data received by the data miners may be pre-processed or processed. Optionally, analysis may occur prior to the data miners receiving and/or viewing the information. In some instances, the systems and methods provided herein may incorporate or work in conjunction with one or more applications that may analyze the data. In some instances, an application store (i.e. 'app store') may be provided with any number of applications that may be able to analyze the data provided by the data contributors. In some instances, various applications may perform different types of analysis on the data. The applications may be developed and/or operated by third parties, or by any party participating in the systems and methods provided herein.

Because stakeholders interact with one another remotely, application programming interfaces (APIs) may be developed and used in order to allow data to be handled by the various parties using the system. APIs may be built to facilitate data file exchange between two stakeholders, such as between the data contributors and the data miners or between the data miners and the secure storage nodes. A data miner, may, for example, send an analysis request to a secure node as an encrypted JSON file containing parameters and values that signify the analysis to be performed and the features used for the analysis. The secure nodes may be programmed to read the information from this file and access the data within memory. They may further be programmed to interpret the instructions from the JSON file and generate a set of computation instructions for the secure computing nodes, and may provide the instructions to the secure computing node in order for the secure computing node to perform the analysis requested by the data miner. APIs may further be used to authenticate users. For example, to access their data, users may be prompted by data verifiers or institutions holding their data to login using their genetic profile identifiers. Contributors may be able to use protocols similar to OAuth to create accounts with or log into external services, such as web portals owned by medical providers or insurance providers, using their genetic identifiers. Secure data storage node operators may use APIs to monitor the filesystems of storage devices, such as server computers, without underlying knowledge of the server computers' filesystems. For example, the node operators may use a custom user interface that makes searching for, organizing, and labeling files more intuitive.

Figure 4:
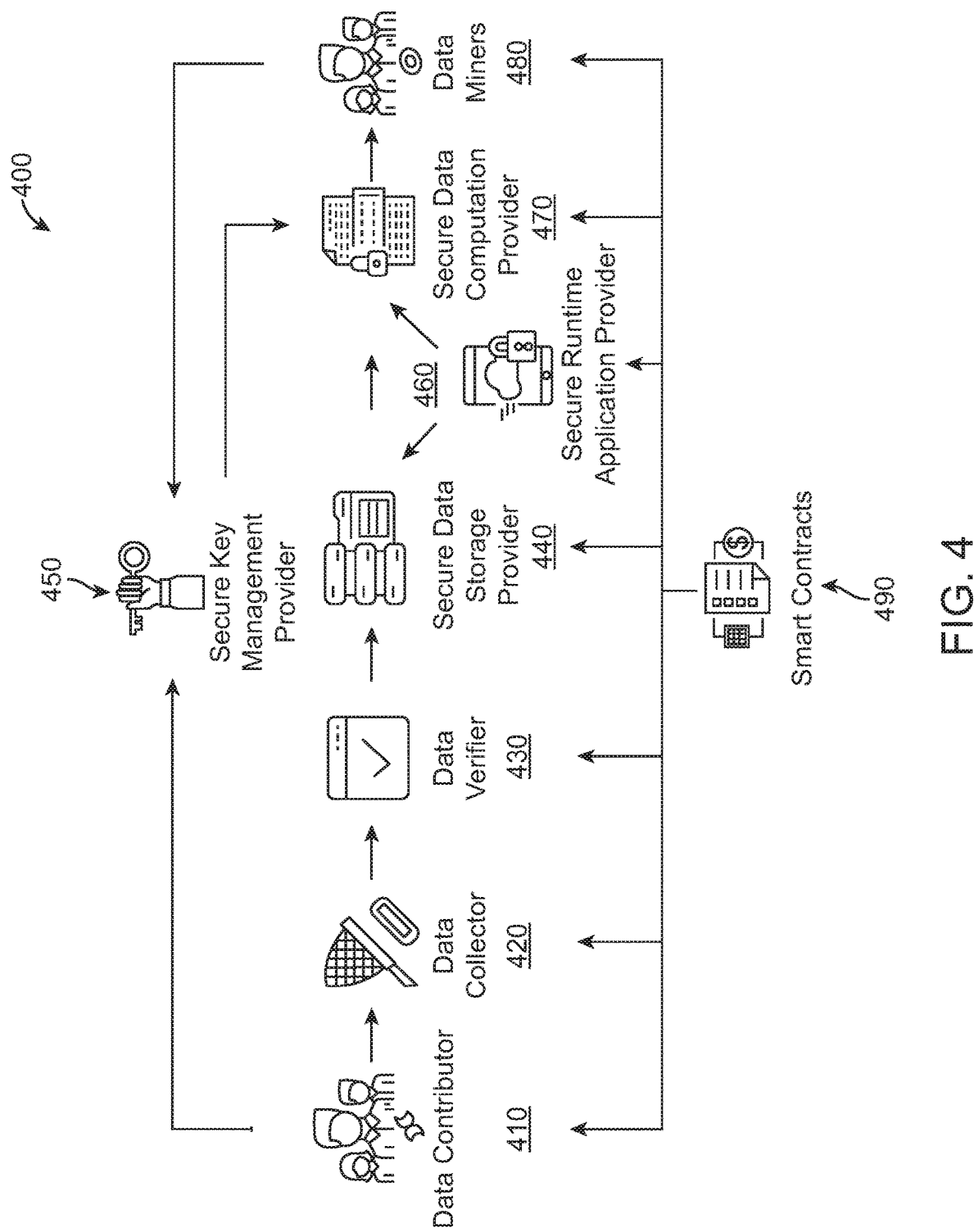
FIG. 4 shows a block diagram of components of the system.

FIG. 4 shows a block diagram 400 of the system components. FIG. 4 includes a data contributor 410, a data collector 420, a data verifier 430, a secure data storage provider 440, a secure key management provider 450, a secure runtime application provider 460, a secure data computation provider 470, a data miner 480, and a smart contract 490. In various embodiments, secure health data marketplaces may have one or more of any of the listed components.

Data miners 480 may be entities that may benefit from access and/or analyze the health information, such as research institutions, insurance agencies, clinical institutions or pharmaceutical companies, whose biomedical research and development require personal genomic data. Data miners may also be philanthropy groups, support groups, health care providers, employers, educational institutions, or matchmakers. Data miners may be incentivized to compensate data contributors when the data contributors share high-quality data. Within the system framework, compensation may be done through the use of smart contracts and blockchain technology: the data miner deposits the payment into the contract account payment. The system then may distribute the payment to all service offering parties once the contract is fulfilled. Payment may be issued as tokens, wire transfers of money, electronic vouchers or coupons, or other electronic payment methods. Compensation for data contributors may be determined using an auction. Alternatively, individual contributors may designate prices for data items using their smart contracts. Alternatively, compensation may be determined algorithmically, for example, pricing data based on amount shared, type of data shared, or quality of data shared. In some implementations, data miners may be required to stake a particular amount of tokens before they are able to request data from contributors.

Data miners may request data needed for particular research activities. For example, data miners may request data on patients expressing specific genes or having specific genetic conditions. For example, the data miners may request contributors who are homozygous or heterozygous for one or more particular alleles. They may also request data from contributors based on medical information, such as whether the patients have diseases, or based on characteristics such as age, height, weight, gender, resting heart rate, blood pressure, diet, exercise level, skin color, or ethnicity. The data miners may request any combination of characteristics, whether they be genetic characteristics, health characteristics, fitness characteristics, demographics, personal information, or any other characteristics. In some instances, the data miners may rank preferences for one or more characteristics. The data miners may request data from contributors that meet all characteristics, or that meet a threshold number of types of characteristics. In some instances, characteristics may be weighted or preferred. Some characteristics may be deemed necessary while other characteristics may merely be deemed preferred. They may request data by specifying criteria on smart contracts. The system then performs matching to find contributor data adhering to the miners' criteria. The data miners may request to perform many different types of data analysis using the requested data. Data miners may request to perform machine learning or statistical analysis on the retrieved data. For example, data miners may want to predict the future occurrence of a specific type of disease on a population of contributors expressing a particular gene. The data miners may be able to choose, using a user interface within a web portal, one or more types of machine learning analysis. These may include binary classification tasks using neural networks or logistic regressions. When the type of analysis is selected, the user interface may alert the data miner that secure computing nodes are competing to perform the type of analysis. When results are available, the user interface may inform the data miner. The data miner may also be able to stake tokens using the user interface, in order to provide rewards for the secure computing nodes to perform the analysis and to the contributors for providing the data. In some instances, the results may be displayed or provided without any regard to order or match of specified criteria. In some instances, the results may be ranked or provided in order based on a degree of how well the data matches the criteria or combination of criteria. A data miner may or may not specify a desired number of hits. For instance, the data miner may only need about 500 results to conduct a desired study. The data miner may specify the number of results, and receive a pool of results that match or are close to the desired number of hits. Alternatively, the data miner may not specify the number of results, and may just utilize the desired amount of data that is returned. In some instances, a data miner may specify a price that the data miner is willing to pay for particular data. This may be on a per unit data basis or a total price for a pool of data. For example, the data miner may specify the data miner is willing to pay X units of currency total for 500 hits that meet the desired criteria. In another example, the data miner may specify the data miner is willing to pay Y units of currency per data contributor that meets the desired criteria. In some instances, recommended pricing points may be displayed to data miners. For example, if a data miner expresses that the data miner wishes to obtain a pool of 1000 data contributors that meet a particular criteria, the system may indicate to obtain at least 1000 hits, the data miner must set at least a particular price point or range of prices, otherwise, there may not be a sufficient number of results. If a data miner is trying to obtain a pool of 100 data contributors that have a particularly rare characteristic, the price point may end up being higher per contributor since the characteristic is so rare. The system may recommend a price point or range of prices to the data miner to obtain a sufficient number of hits.

The data contributor 410 may be an individual or an organization such as a biobank or a company willing to share genomic data. The data contributor receives the compensation for the data in the form of tokens distributed from the smart contracts. Those who participate voluntarily may choose to transfer the received tokens to any charity. Data collectors are registered partners who collect data from the data contributors. A data collector may be a hospital, a research institution, or a health (genome sequencing) provider.

The data contributor 410 may contribute genomic data and health data. Health data may include self-reported health data, such as diet and exercise level. It may also include heart rate, blood pressure, height, weight, BMI, blood type, skin color, eye color, and hair color. Genomic data may include DNA samples. The data contributor 410 may also share his or her genetic history, including family histories of illnesses, using the system.

Data contributors may set prices for sharing their data. For example, if data contributors express genes that are uncommonly expressed or have rare genetic conditions, they may choose to charge miners more for their data. Data contributors may set prices using a user interface. These prices may be listed in the data contributors' smart contracts. For example, the per-record price can be set based on market-driven value of previous studies on the platform. Data from contributors, including personal data and identity data, may be stored in plaintext.

In some jurisdictions, laws may regulate how data may be shared. For example, contributors may be able to opt out of having their data sold. In such an instance, contributors may be compensated less for providing their data.

Data verifiers 430 perform quality control and verify the authenticity of data collected from data contributors. After checking the data quality, data verifiers digitally sign certificates to approve the data. Data verification may be performed by one or more certified organizations, which may operate regionally, nationally, or internationally.

Data verification may be performed in the following way. Chain of custody procedures ensure that samples are not tampered with at any point in the process. A neutral third party may collect the DNA samples. The tested parties may be positively identified when their samples are collected. This may include verifying IDs and photographing and thumb printing the individuals. The samples may be tamper-sealed and securely packaged at the collection site. The samples are carefully inspected for tampering when they arrive at the testing lab. The DNA testing laboratory may be required to send a sample collection kit and explicit collection instructions to the U.S. embassy or embassy-approved panel physician in the foreign country. An additional quality control step may be implemented to verify the EHR data. For example, the disease prevalence within a dataset to be verified can be compared with a population baseline to identify potential quality issues of the data.

A secure data storage provider 440 can be an entity or individual, who can provide a distributed (e.g., OpenStack based SWIFT) or decentralized (e.g., IPFS or Swarm) data storage infrastructure for safeguarding the encrypted biomedical data and for offering reliable and scalable access to data upon requests.

Secure computation providers 450 are computer nodes which provide secure and high-performance biomedical data analysis and computation services. Secure computation technologies may be based on secure hardware and applied cryptography. Secure computation providers 450 may provide storage for genomic and medical data. Secure computation providers may also provide software packages that perform data analysis, e.g., Python data analysis libraries. In order to perform computation-intensive machine learning tasks, secure computation providers may use graphical processing units (GPUs).

Secure key management providers 450 deal with the key generation, exchange, storage, provision, replacement, and revocation of keys within the secure health management system. The secure key management provider manages the access to the underlying sensitive genomic data from the data contributor on the secure storage node and facilitates the secure computation provider to perform secure computation on biomedical data residing on the secure data storage without requiring the peer-to-peer interaction between each data contributor and secure computation provider (upon data contributor's consent). The secure key management provider assists the data contributor and data miner to create and control their encryption keys for encrypting their genome data and queries, respectively, as well as the analysis results.

Symmetric and asymmetric key encryption protocols may be incorporated within the system. Protocols include advanced encryption standard (AES), elliptic curve Diffie-Hellman (ECDH), and elliptic curve digital signature algorithm (ECDSA).

Secure runtime application providers 460 develop secure runtime applications for data miners to be executed by a secure computing provider, where the secure runtime applications can also be hosted on the secure data storage. These apps include intelligent data analytics and direct-to-consumer applications including deep learning, regression models, association test pipelines, genome sequence analysis pipelines, and disease risk analysis applications. Secure runtime applications may be used to perform secure data analysis, by leveraging software guard extensions (SGX). When an application is used by a data miner in a study, a smart contract created by the runtime application provider may be triggered to ensure that certain awards will be provided to the application provider as the incentive.

Smart contracts 490 connect all of the described parties together using blockchain technologies, which enable and ensure individual ownership of data while incentivizing all parties to contribute to the system. Smart contracts are formed from a hash of results as part of a task retrieval by one or more computing nodes. Smart contracts are executed by blockchain miners, where miners have the fundamental roles associated with the blockchain. Privacy protection is achieved by restricting information exchange among off-chain participants. This reduces the volume of transactions that need to be generated and evaluated on the main chain, and instead, keeps only the initial and final transactions there to build a trust root. The system adopts an off-chain secure computation framework, which enables efficient and secure computation over sensitive data.

Figure 5:
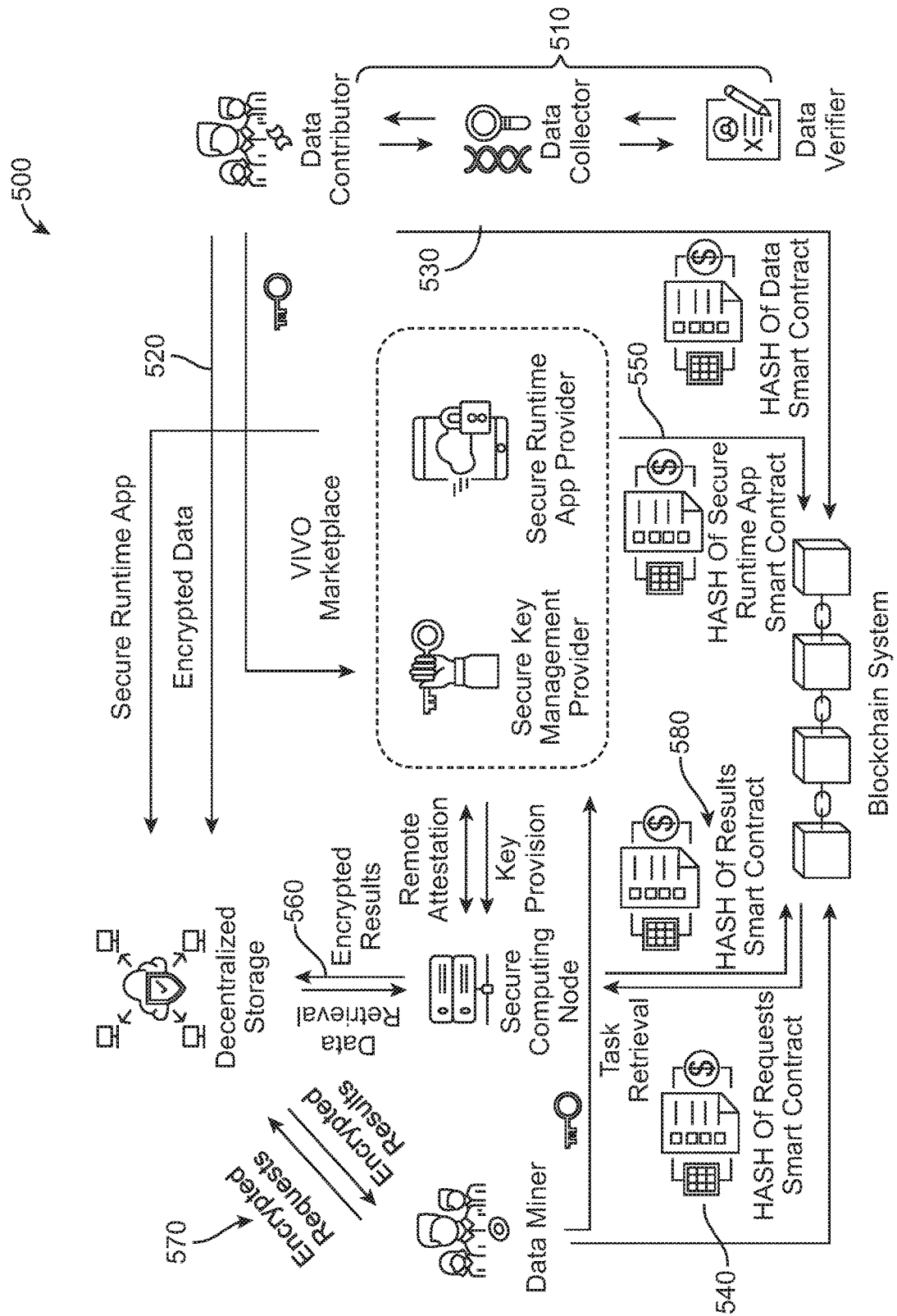
FIG. 5 illustrates data flow through the system.

FIG. 5 illustrates data flow 500 through the system. In a first step, the data contributors (e.g., individuals or institutions) contact 510 the data collectors (e.g., sequencing services or healthcare providers) to obtain their biomedical data (e.g., sequencing or EHR data). A data contributor may provide one or more biological samples to a data collector. The data contributor may provide the biological sample through a mail or package delivery service, or may provide the biological sample in person. The data contributor may provide a biological sample at a health care facility, such as a clinic, hospital, or laboratory. The data collector may receive the sample and perform one or more tests using the sample. For instance, the data collector may sequence the data contributor's sample to obtain genomic data, or phenotypic data. The data collector may perform any type of test or analysis of the data contributor's sample to obtain any type of health related information for the data contributor. The data contributor may or may not provide any other type of information to the data collector, such as clinical history, lifestyle information, or personal information. The data collector may or may not take additional information into account when ascertaining the data contributor's health information.

Contributors may retrieve their data, for example, by communicating with the data collectors using secure email or with a secure file transfer process, such as SFTP. Data files may also sent via secure shell (SSH) or by another secure tunneling protocol. The contributor data may be accessible on a cloud-based system for the data contributor to view and/or access.

The biomedical data may be sent to the data verifier, which validates the data for authenticity along with an unique signature and issues a certificate signed by its private key. The data verifier may be or may use one or more certificate authorities (CA). Issuing certificates may help prevent man-in-the-middle attacks from occurring, making it more difficult for attackers to compromise the contributors' private data. For example, an attacker intercepting the contributor data will not be able to issue the same certificate issued by the data verifier. Thus, other stakeholders within the system would, upon receipt of the data, be alerted to the fact that the data was compromised by a man-in-the-middle attack. The corresponding private key to the data verifier's public key may be stored by the secure key management providers. This public key may be used by data miners and secure computing nodes to verify the digital signature of the data verifier. In order to issue the private key to the secure key management providers, the data verifier may use one of the secure data transfers mentioned.

After obtaining the verified biomedical data, data contributors encrypt 520 their biomedical data and package it with a signature signed by their private key, where private key may be provisioned to the secure key management provider through a secure channel. The secure channel may be implemented using Diffie-Hellman key exchange. To contribute the data to the system, data contributors may first store the encrypted data in the secure data storage. A hash may be generated as the data identifier that may be used for retrieving the specific data by secure computing nodes for data analysis. The hash may be generated using gene identity, for example, by using short tandem repeats (STR) analysis. Gene identity is useful for creating pseudonyms because it is unique to an individual and cannot easily be duplicated or faked. Other gene identifiers that may be used to create hash values include DNA profiling methods such as restriction fragment length polymorphism (RFLP) analysis, polymerase chain reaction (PCR) analysis, amplified fragment length polymorphism (AmpFLP), DNA family relationship analysis, Y-chromosome analysis, mitochondrial analysis, and MiniSTR analysis.

After data contributors have successfully provided the encrypted data along with corresponding keys and the data hash, they may create and manage their profiles on the blockchain. This process is achieved by appending smart contracts 530 to the distributed ledger. If data contributors would like to share their biomedical data, they generate a data profile contract, specify the status of sharing as "open", prepare their data sharing policies, and add the digital signature, public key, and the data identifier to the contract. In addition, the data profile contract may contain separate sharing policies for different types of contributor data, including medical data, insurance data, and genomic data. The data profile contract may contain rules enabling the data to be shared with particular entities, while restricting access to other entities. For example, a data contributor may wish to share data with hospitals, but not with research laboratories or medical clinics. Further, a data profile contract may specify a time or date window in which data may be shared. Outside of this time or date window, data access may be restricted. Whenever the data contributors intend to withdraw their data, they just need to update their sharing status as "closed" by issuing another data profile smart contract. Data contributors may switch their statuses multiple times, while each time a transaction fee associated with the underlying blockchain operation may be charged, to reduce unnecessary changes of sharing status by the data contributors. Data contributors may also edit sharing profile information or preferences by issuing new smart contracts.

A data contributor profile may contain information the data contributor is willing to share. This information may include insurance policy information, such as the contributor's policy number, group number, type of coverage, and payment information. The contributor profile may contain information about medical conditions, types of medications taken or prescribed, medical histories, and family medical histories. The contributor profile may include genomic information, such as DNA sequence information, genetic disease or disorder risks, mitochondrial haplogroup, and inherited trait assessments.

Data miners then generate 540 smart contracts to recruit specified individuals (with "open" status) through the system for a particular type of analysis. These smart contracts are request contracts. The data miners may define matching conditions (encrypted for privacy/security protection of data miners), e.g. contributor personal genomes containing (or not containing) particular mutations or expressing particular genes, contributors exhibiting particular clinical symptoms, contributors having specific health insurance plans, contributors having family histories of particular diseases, and contributors having parents with specific combinations of alleles. Data miners may specify a particular number of matches in the request contract. In order for data miners to receive the data corresponding to their queries, the secure runtime application provider prepares a secure matching application for data miners and registers 550 it through a smart contract on the blockchain. The secure application may include one or more functions used to match data miners' requests with data from data contributors that corresponds with the miners' requests. For example, the secure application may have a function that extracts matching conditions from the data miners' smart contracts. In order to ensure that data retains its integrity and validity as it is transferred, the secure application may have an additional function that digitally signs the extracted matching conditions using an embedded private key. The secure application may also have a function that returns a list of matching candidates to the data miner. A data miner may specify rewards (through the request contract) as incentives to each party involved in the system. Rewards may include a particular number of incentive tokens or a particular cash payment value. Additional tokens may be issued as bonuses to secure computing nodes that perform computing tasks more efficiently. The secure computing nodes may monitor the blockchain periodically. Once there is a new request contract successfully deployed on blockchain whose reward has not been claimed, they may grab the contract and execute 560 the specified computation tasks in a secure environment.

The secure computing nodes may use one or more encryption techniques to provide data security at many stages as the data interacts with various stakeholders. For example, contributors may use one or more encryption schemes when transmitting data to secure computing nodes for analysis. Data miners may make encrypted requests to secure data storage nodes to request particular types of data analysis. The secure storage nodes may then, in turn, send encrypted requests to secure data computation nodes and provide the nodes with the data for secure analysis. The secure data computation nodes may return encrypted results to the storage nodes, which return the results to the data miners. Encryption may be performed using AES based symmetric encryption schemes or homomorphic encryption (HE) based asymmetric encryption schemes, including somewhat homomorphic encryption and fully homomorphic encryption. Executing the computation tasks securely may be performed using homomorphic encryption (HE), secure multiparty computation (SMC) and/or trusted execution environment (TEE). HE allows computation tasks to be computed on encrypted data without having to decrypt the data before performing the computation is performed. For example, HE may be used to compute $x*y$ by encrypting both x and y and finding the product $E(x)*E(y)$. If an encryption scheme is chosen such that $E(x)*E(y)=E(x*y)$, the encrypted product $E(x*y)$ can be decrypted following computation to form the product $x*y$. HE may work with many types of encryption schemes or cryptosystems, including RSA, ElGamal, Goldwasser-Micali, Benaloh, FV, BGV, and Paillier. Secure Multi-Party Computation (MPC) is an interactive protocol for computing some functions (represented as circuits) between multiple parties. Depending on the type of circuit, there are two primary methods to implement MPC. A garbled circuit is efficient for boolean circuits, while performing MPC over shares of a secret is useful for arithmetic circuits. The MPC protocol has the advantage of being information theoretical secure rather than relying on computational assumption as long as there is no collusion. Data is secret-shared rather than encrypted. Shares on each server reveal no information about the secrets without all servers colluding with each other. Trusted execution environment (TEE) provides an isolated memory and computation space (e.g., enclave) within hardware, in which sensitive data can be analyzed efficiently and securely. TEE provides developers with the ability to create isolated memory regions, called enclaves, inside the application address space. The enclave memory is encrypted using strong cryptographic algorithms and is only decrypted when data is loaded into the CPU caches and registers. When an enclave is initialized, the initial codes and data of an enclave are kept in the encrypted memory, called enclave page cache or EPC. A remote party can then verify the identity of the enclave by comparing the enclave's measurement through a process called remote attestation. Using remote attestation, the owner of sensitive data will gain trust about the code running inside an enclave and can therefore let the enclave decrypt the encrypted data on the remote server (e.g., cloud), ensuring only the intended computation to be performed on the data inside the trusted enclave (without exposing the plaintext content of the data to the operating systems or even the owner of the server).

Individual data privacy may be maintained using differential privacy. Differential privacy involves adding noise to a data set, so that an attacker cannot infer information about a particular subject from which data was collected. For example, if a study attempts to identify a correlation between liver cancer and cirrhosis, and an attacker had background information on all but one participant in the study, noise would be added to the data to ensure that the attacker would not be able to infer whether or not the remaining participant had cirrhosis.

Furthermore, the data miner is able to set 570 an additional request contract to issue data analysis tasks by using securely queried data in the previous step. Secure computation may be achieved using dynamic session keys. These session keys may be generated using a trusted execution environment (TEE) that restricts access to many computing processes, lessening a risk of key breach. The dynamic session keys may be used by the stakeholders to distribute private keys, allowing various components within the system to decrypt requests and transferred data. In addition, encryption keys used by the various stakeholders of the system may be placed in a hierarchy. The hierarchy may assign different types of keys to different types of data. Thus, in an event of key breach, a compromised encryption key may still not allow an attacker to decrypt compromised data collected by the attacker.

Once the secure computation is finished, the encrypted results may be sent back to the corresponding data miner and the hash of the results may be recorded 580 on the blockchain through the results contract. The request contract may then be triggered to distribute rewards to contributors and to log transactions onto the blockchain.

Figure 6:
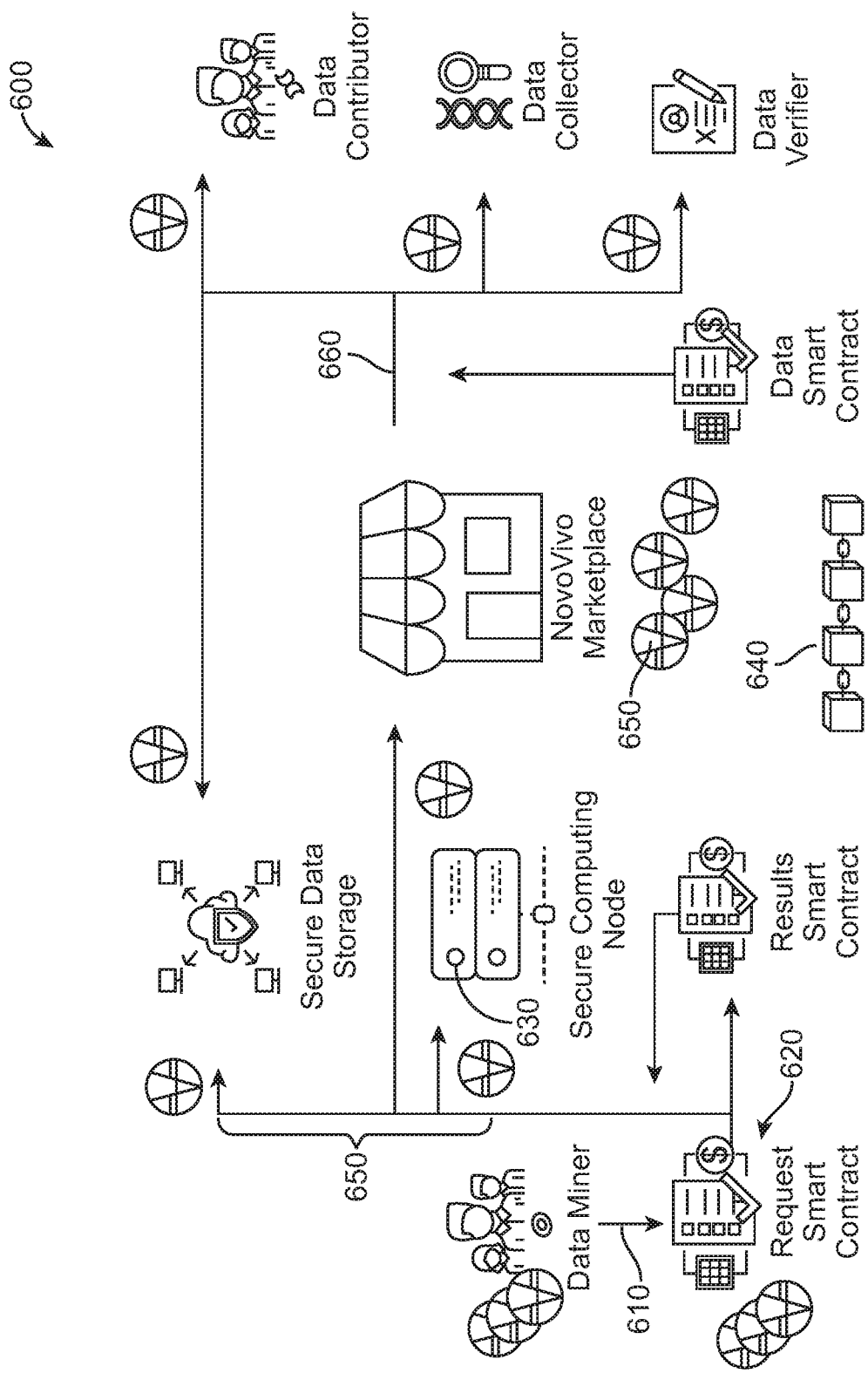
FIG. 6 describes a flow of incentive tokens through the system.

FIG. 6 describes a flow 600 of incentive tokens through the system. The incentive tokens may be secure tokens, with protections that prevent them from being transferred easily between users or stolen. The tokens may be exchangeable for money. A token may have a fixed value tied to a specific currency, or its value may fluctuate in response to an open market. Different tokens may be issued to different stakeholders. For example, investors, researchers, and contributors may each receive different types of tokens with different functionalities. System stakeholders may accept tokens themselves as payment, instead of converting the tokens to money. Tokens may be used to purchase health insurance.

Data contributors may be compensated in particular manners for providing particular data values. For example, data contributors who have rare medical or genetic conditions may be compensated more for providing their genomic or medical histories. In some instances, multiple data contributors may provide data for an analysis task performed by a data miner. Data contributors whom provide more data or better quality data may be compensated with more tokens than are data contributors who contribute less data. Data contributors may also receive greater rewards when their data points are used in more studies. For example, a data contributor who contributes data to five different studies may be compensated more than a data contributor who contributes to only three studies.

Token rewards may fluctuate as the value of data changes over time. For example, when additional data is collected from data contributors, it may be applicable to multiple studies. Because the additional data has more applications, it also has more value. In addition, the data collected from a particular contributor may be augmented when additional data is collected from the contributor. For example, time series data may be collected, on a recurring basis, about a contributor's vital statistics, diet, exercise regimen, and other factors over time. This data may be used for time series analysis, such as for assessing the probability of the contributor contracting a disease or exhibiting a medical event, such as a heart attack or stroke. Thus, the augmented data provides better information for particular types of analysis, and thus appreciates in value. Thus, data contributors may be rewarded with larger amounts of tokens as they remain connected to the system's marketplace. In exchange, data miners may be able to consistently and reliably retrieve new data for analysis, and may be able to perform research on time scales unavailable before the implementation of the system.

In a first operation, a data miner may initiate 610 a request for a secure analysis of health information associated with at least one data contributor to the secure storage nodes. The request may contain the type of information desired, such as genomic sequence data, data on genetic conditions, family medical history, or health-related statistics. The data miner 620 puts a hash of the request in a smart contract on the public ledger. In order to have his or her request picked up by the secure computing node, the data miner may to stake a number of tokens in that smart contract. The number of tokens staked may depend on a type of request made by the data miner. For example, when more data is requested, the data miner may have to stake a larger number of tokens. Data miners can purchase tokens from the market with real currency. In contrast, the blockchain miners can gain token through mining blocks for different transactions. Second, secure computing nodes compete 630 to pick up the requested analysis. A price discovery (auction) mechanism may be used to determine in real time one or more prices for secure computing resources. If additional computing resources are required to execute the requested analysis, one or more computing nodes may each take a share of the computing test and aggregate results securely. After the computation is complete, a hash of results is recorded 640 on the blockchain. This triggers the first smart contract, enabling the data miner to provide 650 the staked number of incentive tokens to a token pool. The token pool implements one or more rules to determine the distribution of tokens to various stakeholders in the system. For example, a hospital providing the data may receive a larger fraction of the tokens than a data contributor, who may receive fewer tokens because he or she did not directly provide the data to the data miner. The tokens are distributed to stakeholders including secure computing nodes, decentralized storage nodes and other system components. To protect the digital identity (e.g., a digital wallet address) of data contributors, tokens may not immediately be released to them in order to avoid creating associations between particular data miners and data contributors. Instead, tokens may be released to contributors on a scheduled basis, such as weekly, biweekly, quarterly, monthly, or annually. Administrators of the secure computing nodes may use the issued incentive tokens to increase, update, or replace computing infrastructure, enabling the secure computing nodes to compete more effectively when bidding to perform analysis tasks from the data miners. Or administrators of the secure computing nodes can resell the token in the market to gain real currency. A secure incentive token is identifiable by a unique public key address, wherein only the data contributor intended by the data miner to receive the token may have access to the corresponding private key. When an incentive token is issued by a data miner to a particular data contributor, the token may be encrypted using the intended recipient's public key. Next, data contributors, data verifiers, and related infrastructure stakeholders (e.g., data collectors like sequencing capacity provider, EHR providers, etc.) receive 660 tokens from the system. The amount of tokens will be calculated such that it reflects a fair value of the data based on the price discovery auctions.

Figure 8:
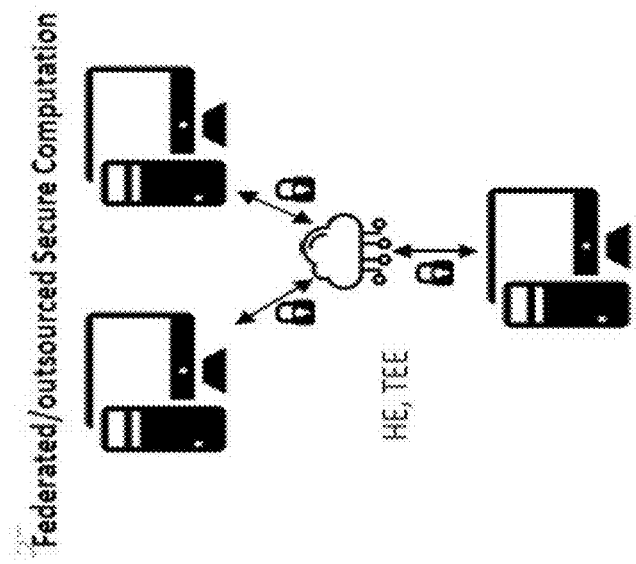
FIG. 8 shows federated or outsourced secure computation.
Figure 7:
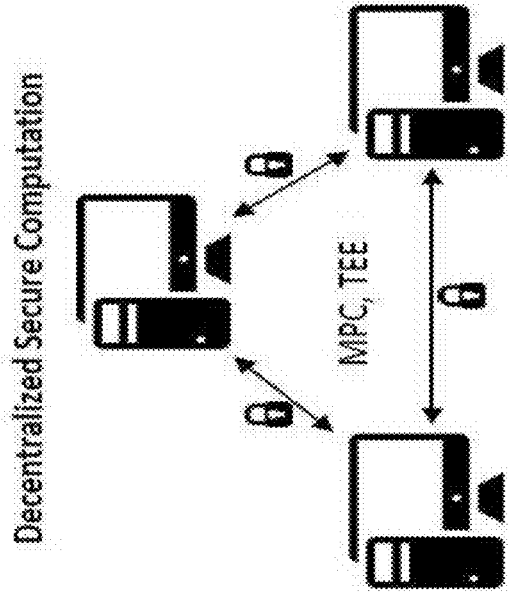
FIG. 7 illustrates decentralized secure computation.

FIGS. 7 and 8 show methods of distributed computing. FIG. 7 illustrates decentralized secure computation. In decentralized secure computation, analysis is performed in a distributed way, without a trusted third party. Data is split among different nodes, and they compute functions together without leaking information to other nodes. Specifically, no single party ever has access to data in its entirety; instead, every party has a meaningless (i.e., seemingly random) piece of it. FIG. 8 shows federated/outsourced secure computation. In federated data analysis, computers each perform local analysis on their data using local methods. The data is then encrypted and combined at a central node (outsourced computation), which performs an aggregated total analysis. Federated data analysis methods try to learn a global statistical model without disclosing patient-level data from local parties.

Figure 9:
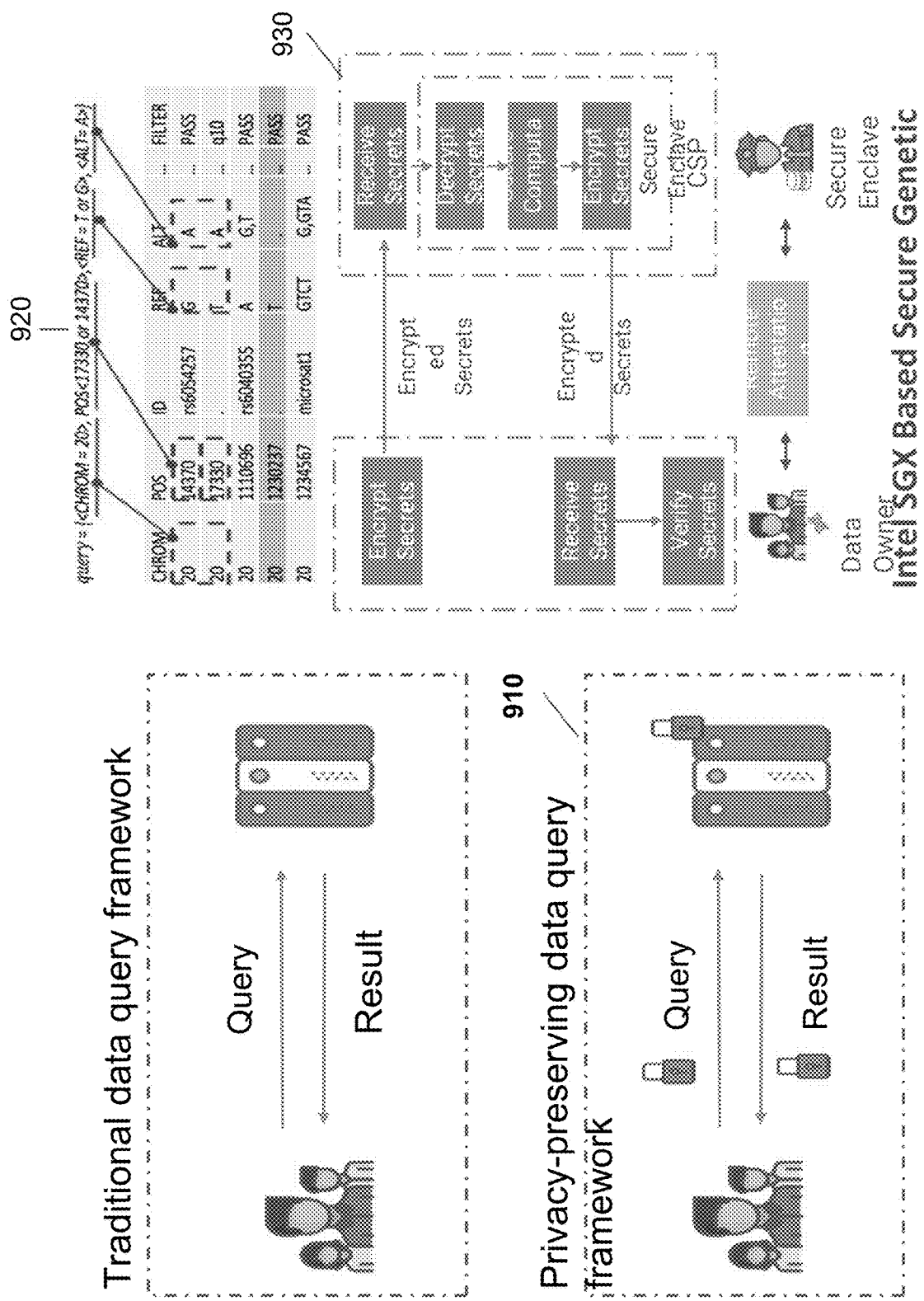
FIG. 9 shows a high-level diagram of a privacy-preserving secure method of genetic testing.

FIG. 9 shows a high-level diagram 910 of a privacy-preserving secure method of genetic testing. Using this method, the query, information storage, and received result are all encrypted. The privacy-preserving method may be implemented by using Intel® Software Guard Extensions (SGX).

FIG. 9 shows an example of a query 920 used to request data from a data owner. In this example. The query includes 4 tuples, and each tuple indicates a matching condition. In this example, the query will locate all records in a file that meet the conditions of CHROM=20, POS=17330 or 14370, REF='T' or 'G' and ALT='A'. The results of this query will the count of matched records (i.e. 2 in this example). This query is equivalent to a Structured Query Language (SQL) query as follows: SELECT count(*) FROM sample.vcf WHERE CHROM=2 AND (POS=17330 or 14370) AND (REF='T' or 'G') AND ALT='A'.

An overview 930 of an SGX framework is also illustrated in FIG. 9. An SGX based application consists of data owner, untrusted cloud service provider (CSP), and a secure enclave. First, the data owner establishes a secure channel with the enclave hosted by an untrusted CSP through a remote attestation process. Then, the data owner can securely upload data to the CSP (data provisioning). In SGX, all decrypted secrets can only be accessed by the authorized codes, which also lie inside the enclave. A hardware supported access control proxy guarantees the code and data cannot be accessed or modified by software installed outside the secure enclave.

Figure 10:
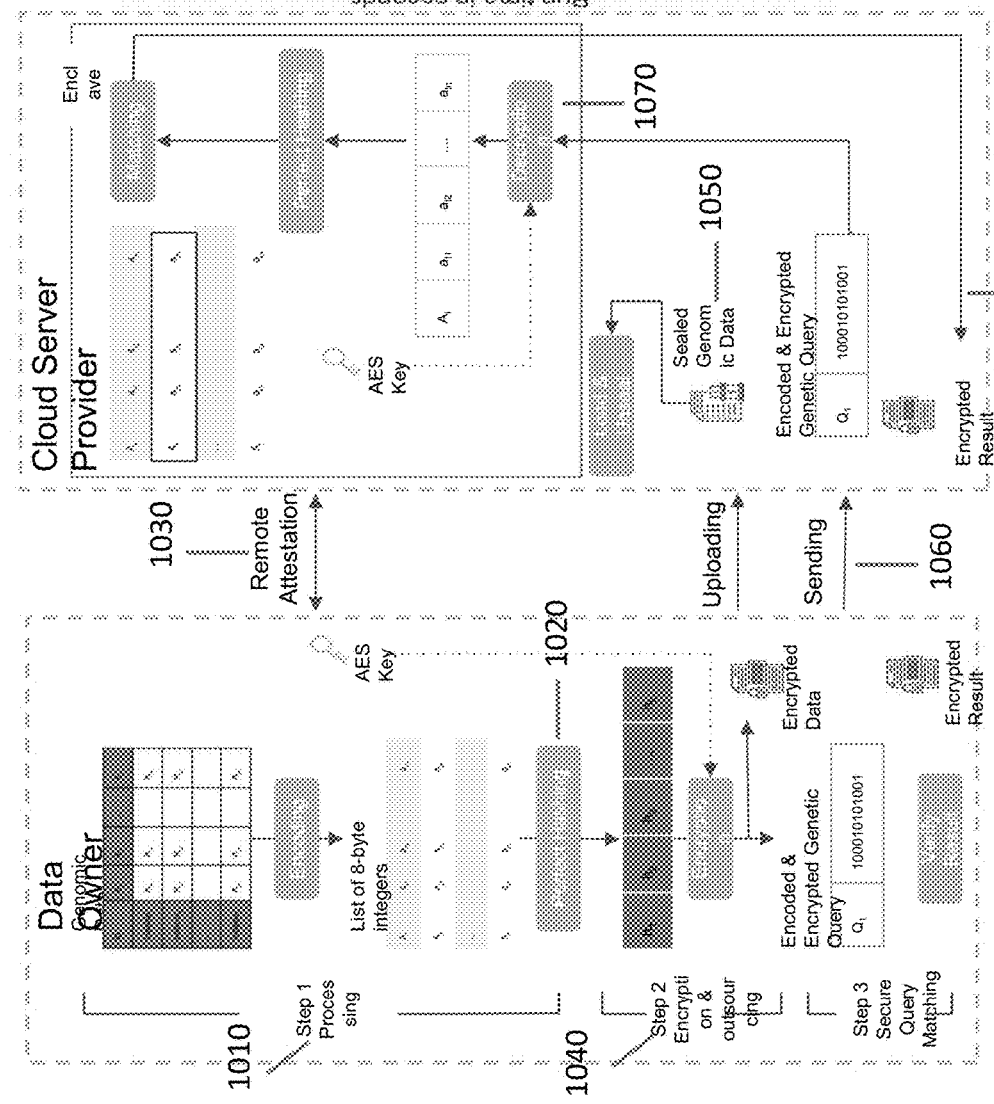
FIG. 10 shows an implementation using the SGX framework of FIG. 9 in order to securely test genomic data.

FIG. 10 shows an implementation 1000 using the SGX framework of FIG. 9 in order to securely test genomic data. In the implementation of FIG. 10, the data owner holds a private genomic database in Variant Call Format (VCF). Pre-processing is first performed 1010 to reduce overheads during test performance. After the pre-processing, the data owner hashes 1020 the data to further increase efficiency. Next, the data owner and CSP perform 1030 remote attestation to authenticate one another and ensure data integrity. The data owner next negotiates a session key with an enclave within the cloud service provider. Then, the data owner encrypts 1040 the genomic data and uploads it to the cloud service provider. The data may be sealed 1050 for long-term storage. After receiving the data the CSP may respond to queries from the data owner. Before sending a query, the data owner again remotely attests the enclave located within the CSP. It then sends an encrypted query 1060, requesting, for example, the chromosome number, position, reference, and alternative alleles. When it receives the query, the enclave unseals the data and uses the hash function in order to execute 1070 the query. The enclave then encrypts a number of matches to the data owner's query and sends 1080 them back to the data owner.

Figure 11:
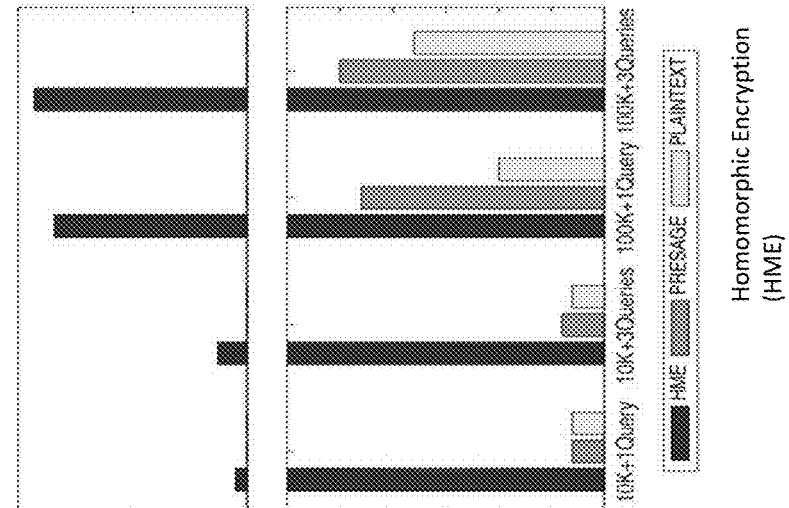
FIG. 11 shows an evaluation of the secure genomic testing SGX framework.

FIG. 11 shows an evaluation 1100 of the secure genomic testing SGX framework. In this example, the framework was implemented over 10,000 single nucleotide polymorphisms (SNPs), and 100,000 SNPs. SNPs are among the most common types of genetic variation. As shown, the SGX framework is 120-times faster than a method using holomorphic encryption (HME).

Figure 12:
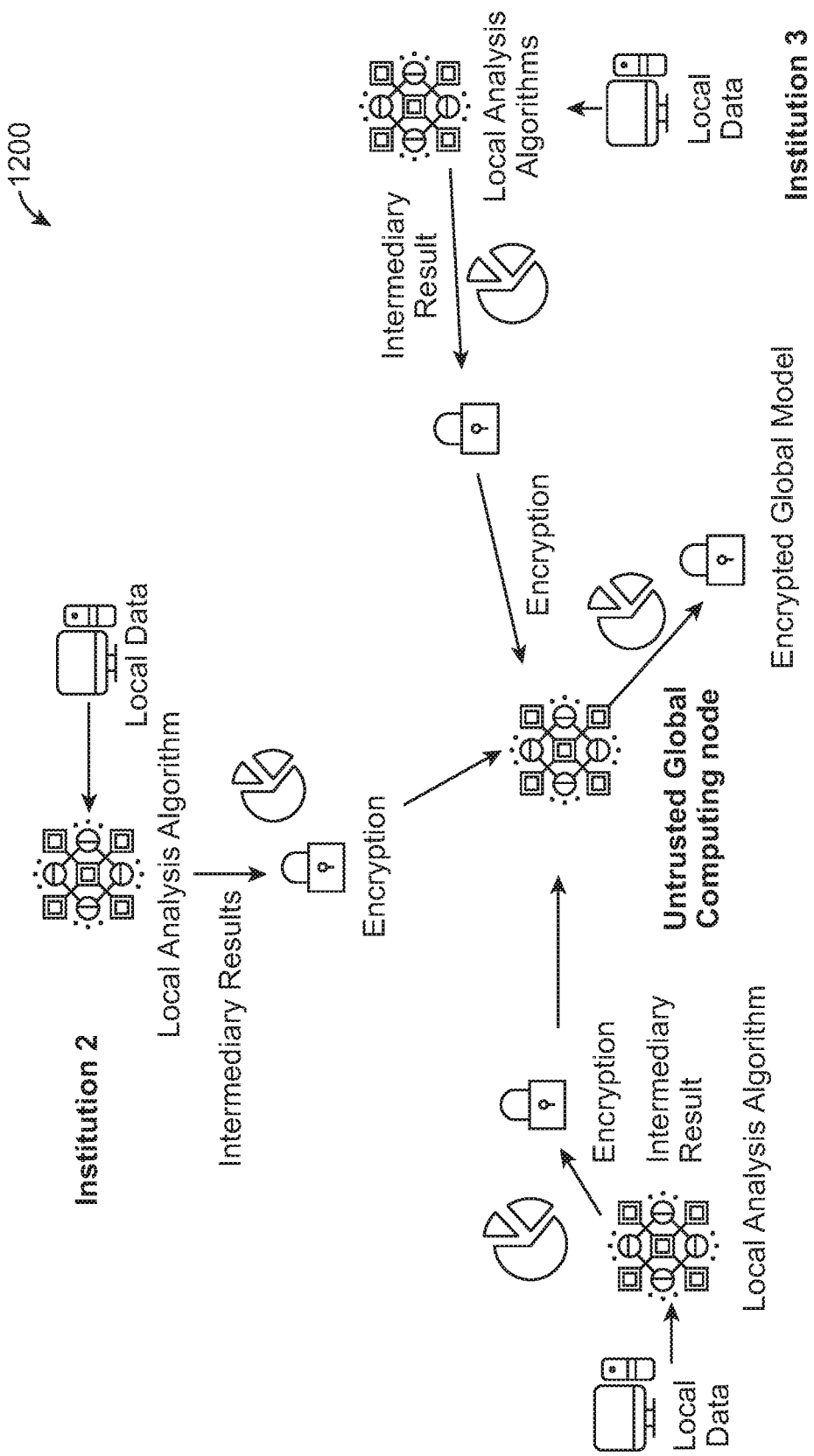
FIG. 12 shows an embodiment of federated data analysis.

FIG. 12 shows an embodiment 1200 of federated data analysis. At three different institutions, algorithms are performed on local data in order to obtain intermediate results. These results are then encrypted and sent to an untrusted global computing node. The global node performs analysis on the aggregated local data and encrypts the result of its analysis. This result becomes an encrypted global model.

FIGS. 13 and 14 show two methods of distributing data in order to perform federated data analysis. These methods allow analysis to be performed in a secure manner, preserving data privacy for institutions. Different types of analysis may be performed, including logistic regressions and support vector machines.

FIG. 13 shows an illustration 1300 of horizontally distributed data. Horizontal partitions have different observations, each with values for the same set of features. In FIG. 13, two institutions have different sets of local data for different patients, but the same features from each patient are collected at each institution. This method of data analysis may allow, for examples, hospitals to jointly study the effect of a specific treatment with larger sample size from different patients.

FIG. 14 shows an illustration 1400 of vertically distributed data. Vertical partitions share a set of observations, but each partition collects data representing a different set features. Such a setup can allow hospitals to perform collaborative analysis, even though they each may maintain different pieces of information per patient.

Figures 15, 16:
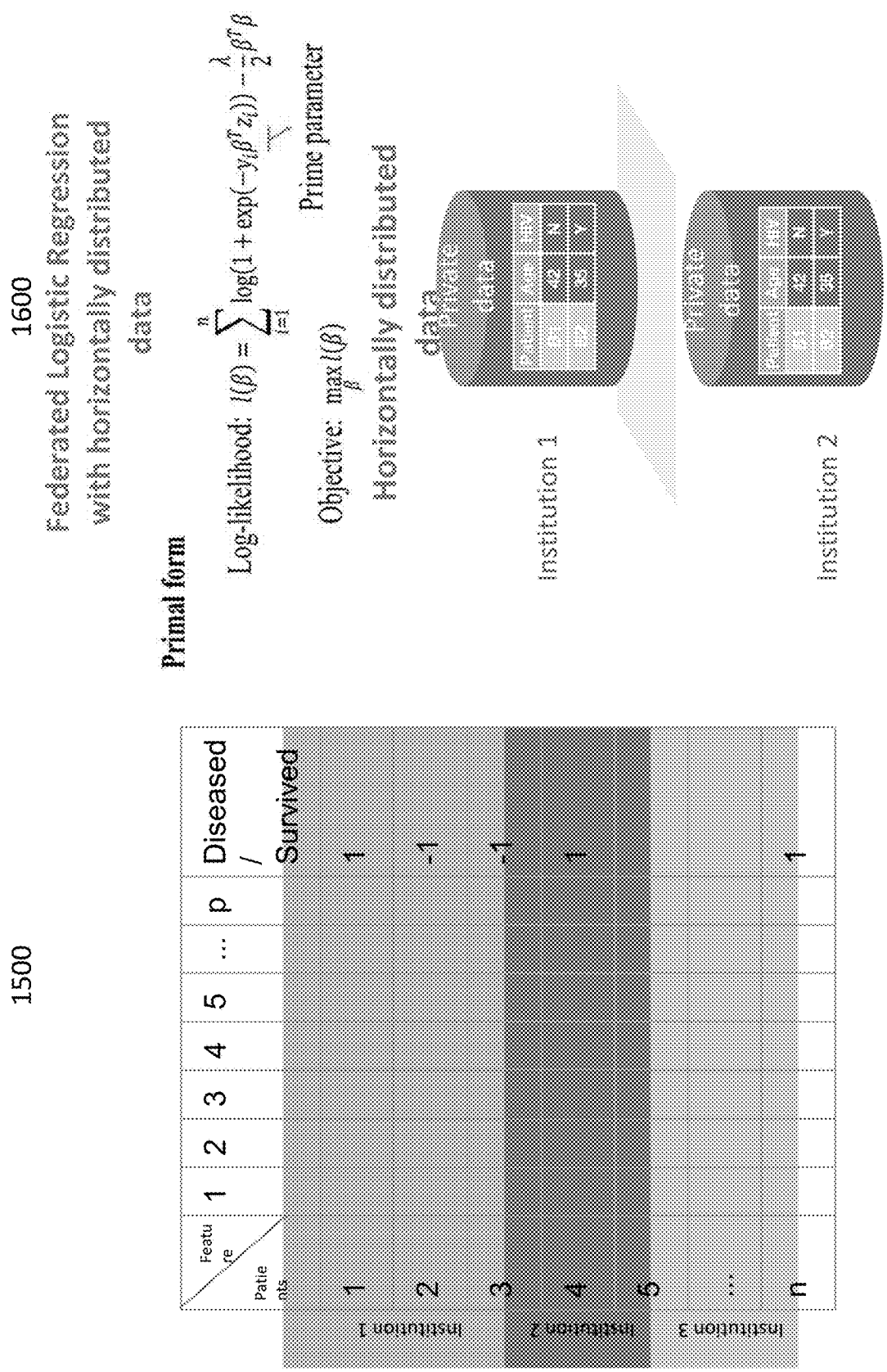
FIGS. 15 and 16 show an example type of data analysis used to perform a federated logistic regression on horizontally partitioned data.

FIGS. 15 and 16 show an example type of data analysis used to perform a federated logistic regression on horizontally partitioned data. Logistic regressions are used to perform binary classification. For example, a logistic regression may be used to analyze a set of patient features and perform disease risk prediction or decision supports. In order to calculate the federated logistic regression on horizontally partitioned data, a virtual matrix is created by concatenating the patients across all institutions to form a set of rows, with individual patient feature values comprising the columns. In order to enhance security, dot products of the feature values within each institution will be used. Calculating dot products of these values within each institution preserves the individual patient privacy, by sharing aggregated statistics instead of patient-level information. Additional encryption can be applied on top of the statistics, through which unauthorized user would not be able to reverse-engineer to find the underlying feature values. FIG. 15 shows this virtual matrix 1500. FIG. 16 shows a method 1600 for maximizing a log-likelihood function, used to train the logistic regression by estimating the prime parameter $\beta$. $\beta$, in this expression, relates model parameters of the logistic regression trained over the patient feature values.

Figures 17, 18:
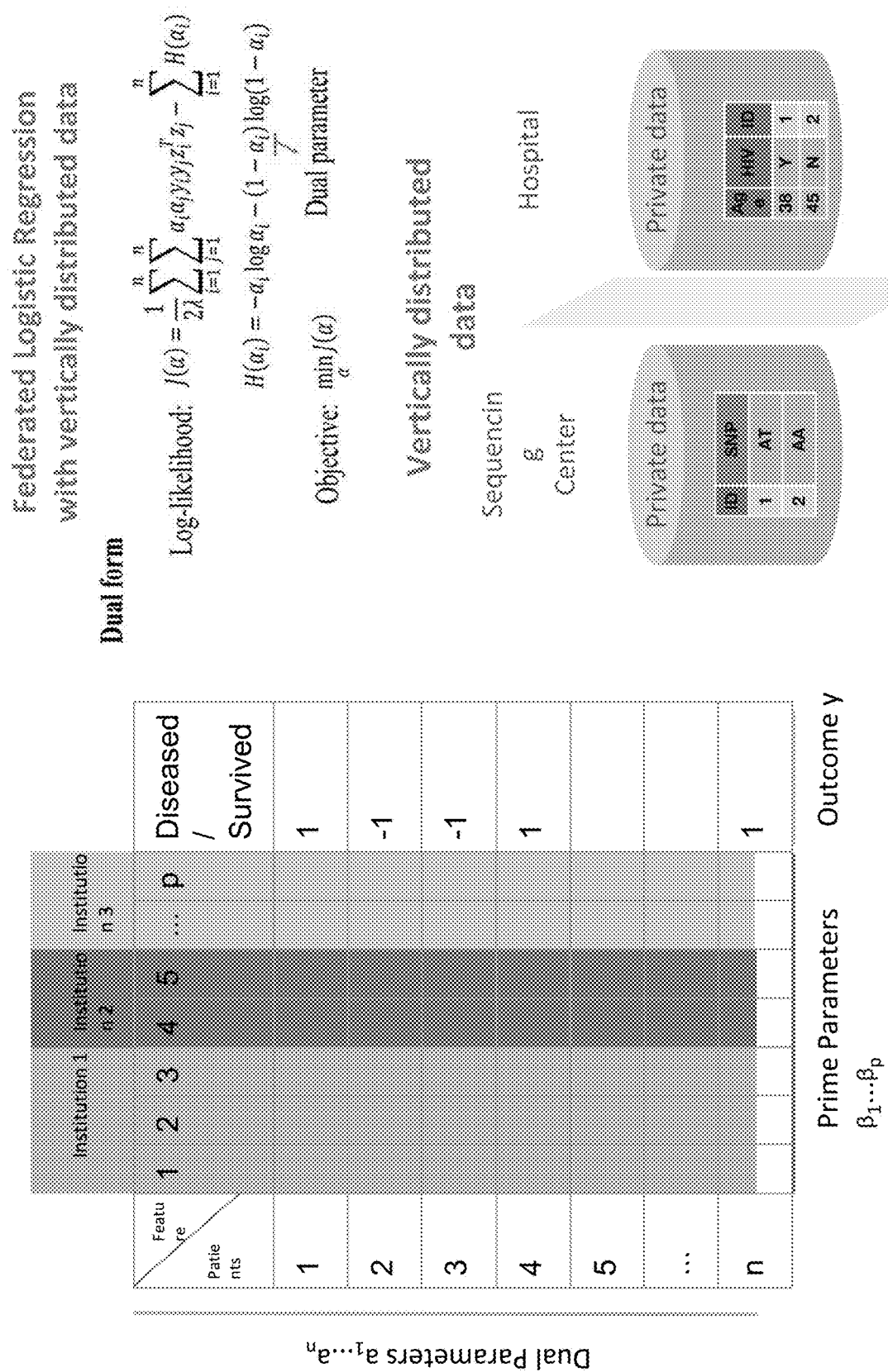
FIGS. 17 and 18 show a federated logistic regression for vertically partitioned data.

FIGS. 17 and 18 show a federated logistic regression for vertically partitioned data. The method for maximizing the log-likelihood function used in FIG. 16 cannot be used with vertically partitioned data, so the log-likelihood function is optimized for a dual parameter α instead. Thus, the dual parameter α, instead of β, determines the relationship between the features and the classification output.

Figure 19:
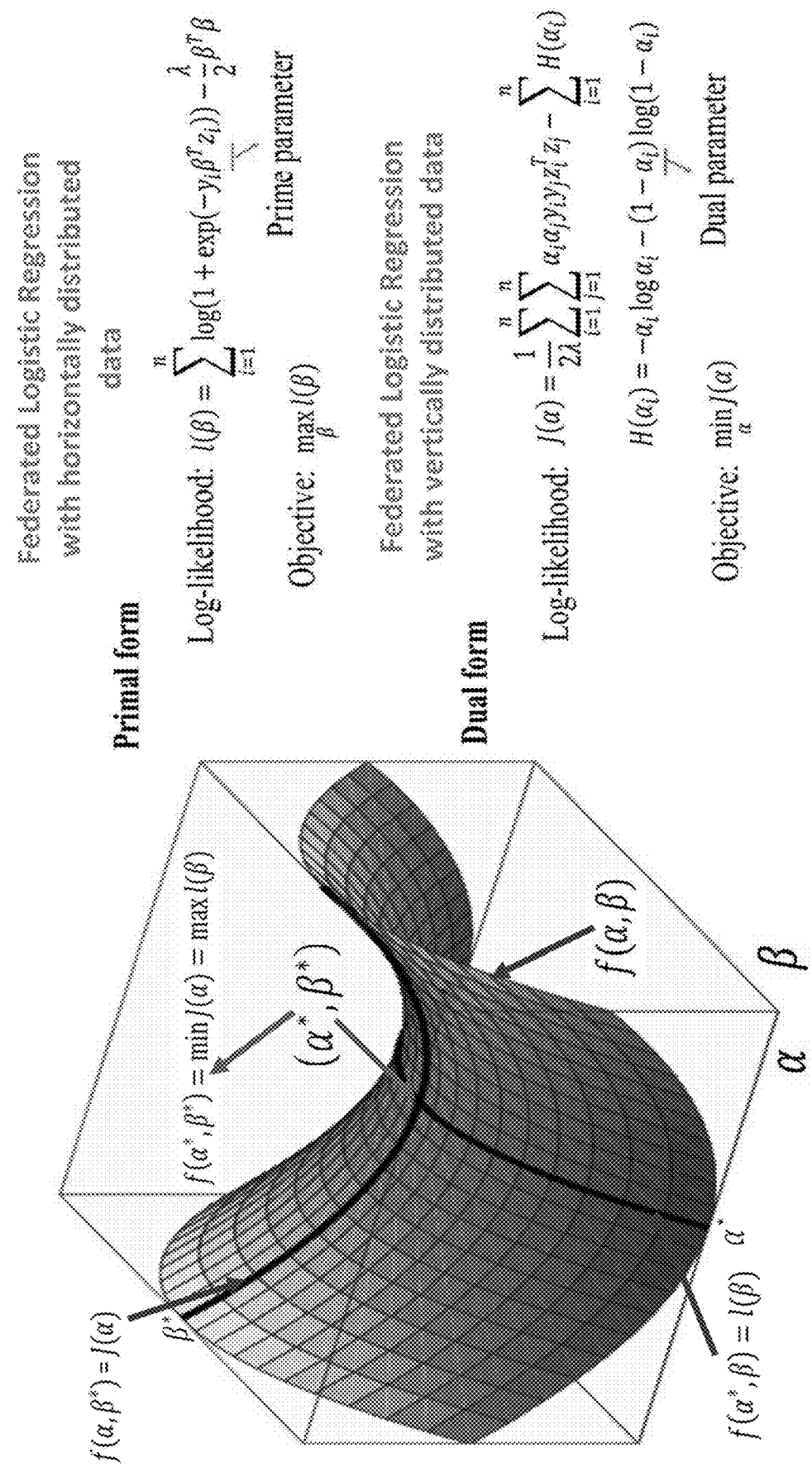
FIG. 19 shows a plot of dual and primal log-likelihood functions.

FIG. 19 shows a plot 1900 of dual and primal log-likelihood functions. It is shown in the graph that the maximum of the prime function is equivalent to the minimum of the dual function. This shows that an accurate logistic regression can be determined for both partitioning methods.

Figure 20:
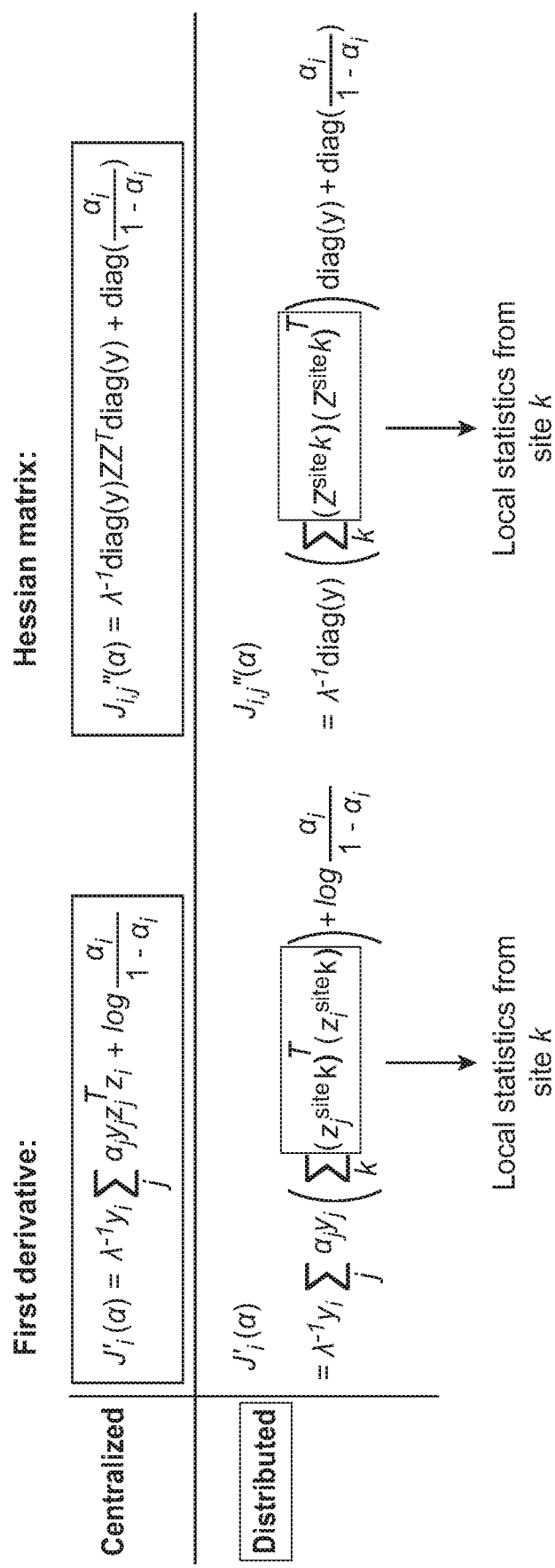
FIG. 20 shows a decomposition of the dual logistic regression of FIGS. 17 and 18 with each set of local statistics isolated.

FIG. 20 shows a decomposition of the dual logistic regression of FIGS. 17 and 18 with each set of local statistics isolated. FIG. 20 also shows method of calculating the dual logistic regression using a Newton-Raphson method. In addition, a fixed-Hessian matrix can be used to reduce the complexity of the algorithm used to calculate the regression, by avoiding time-consuming matrix inversion operations in each iteration.

FIG. 21 shows average computing times for training the regression models of FIGS. 15, 16, 17, 18, and 20. FIG. 21 includes times for the vertically distributed federated logistic regression, with iterative or fixed Hessian using both GPU and CPU, as well as for the horizontally distributed federated logistic regression.

Figure 22:
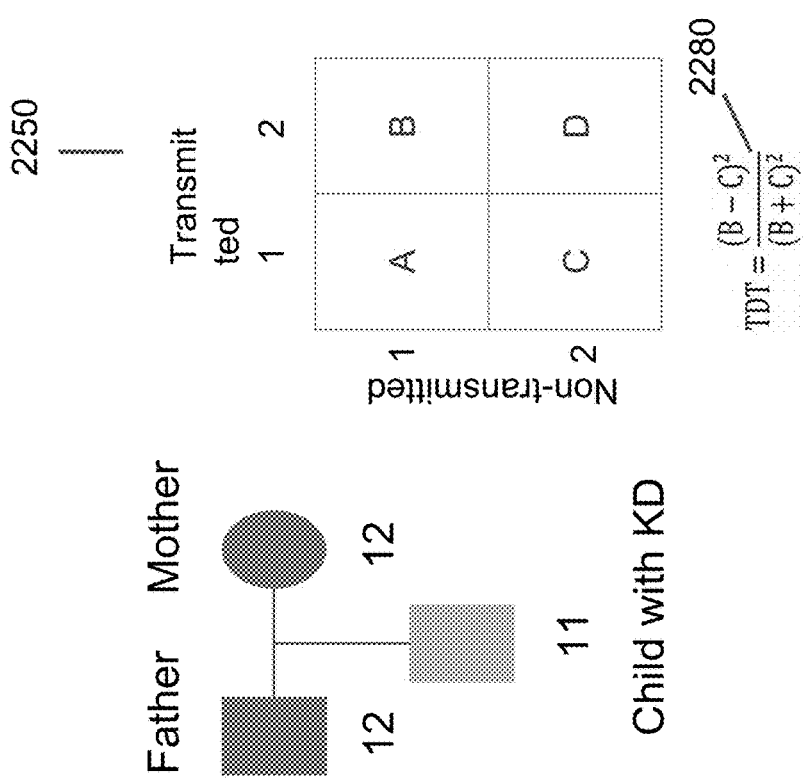
FIG. 22 shows a transmission disequilibrium test (TDT)
Figure 23:
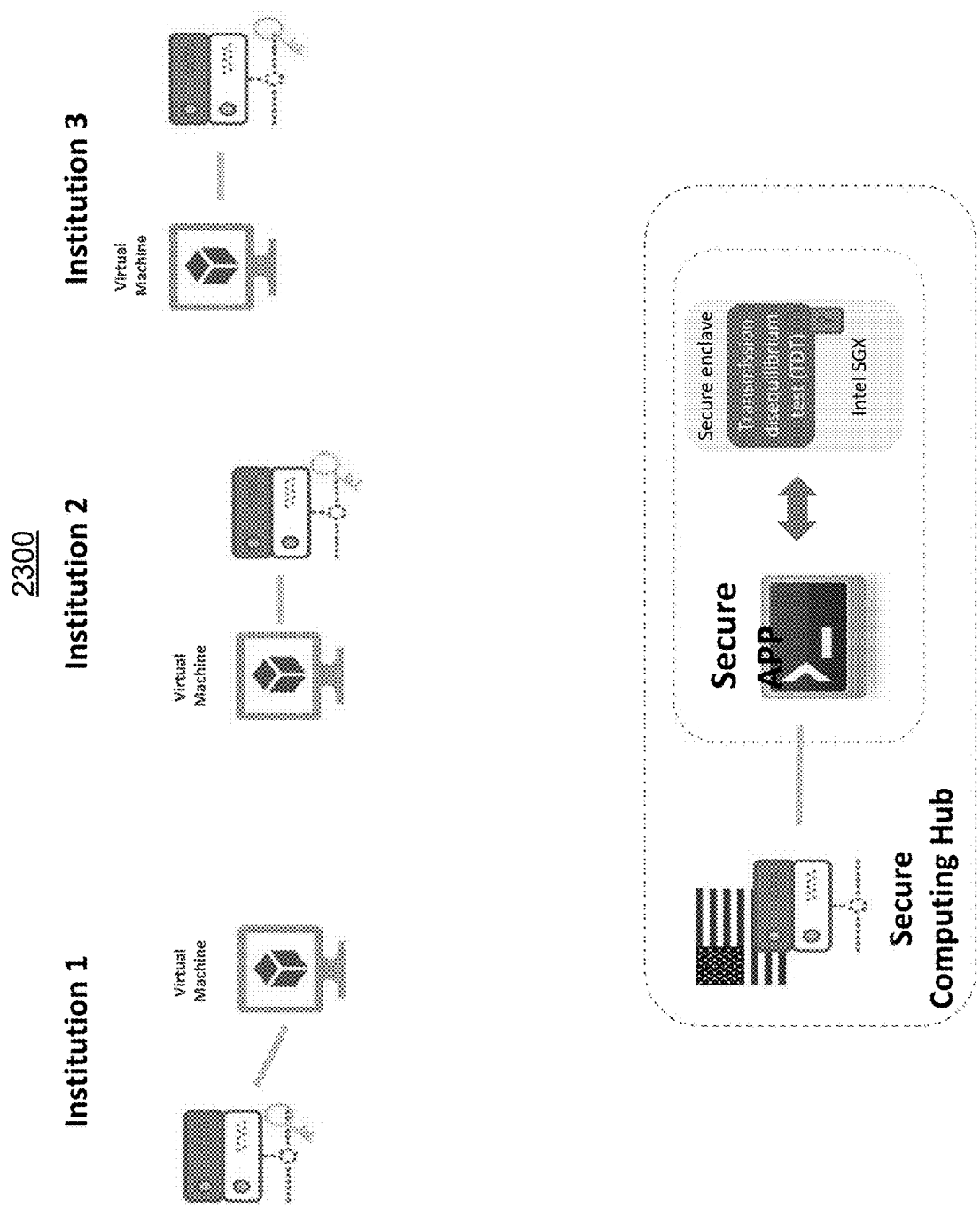
FIGS. 23-26 show a system for computing the TDT test with federated data from multiple sources.
Figure 24:
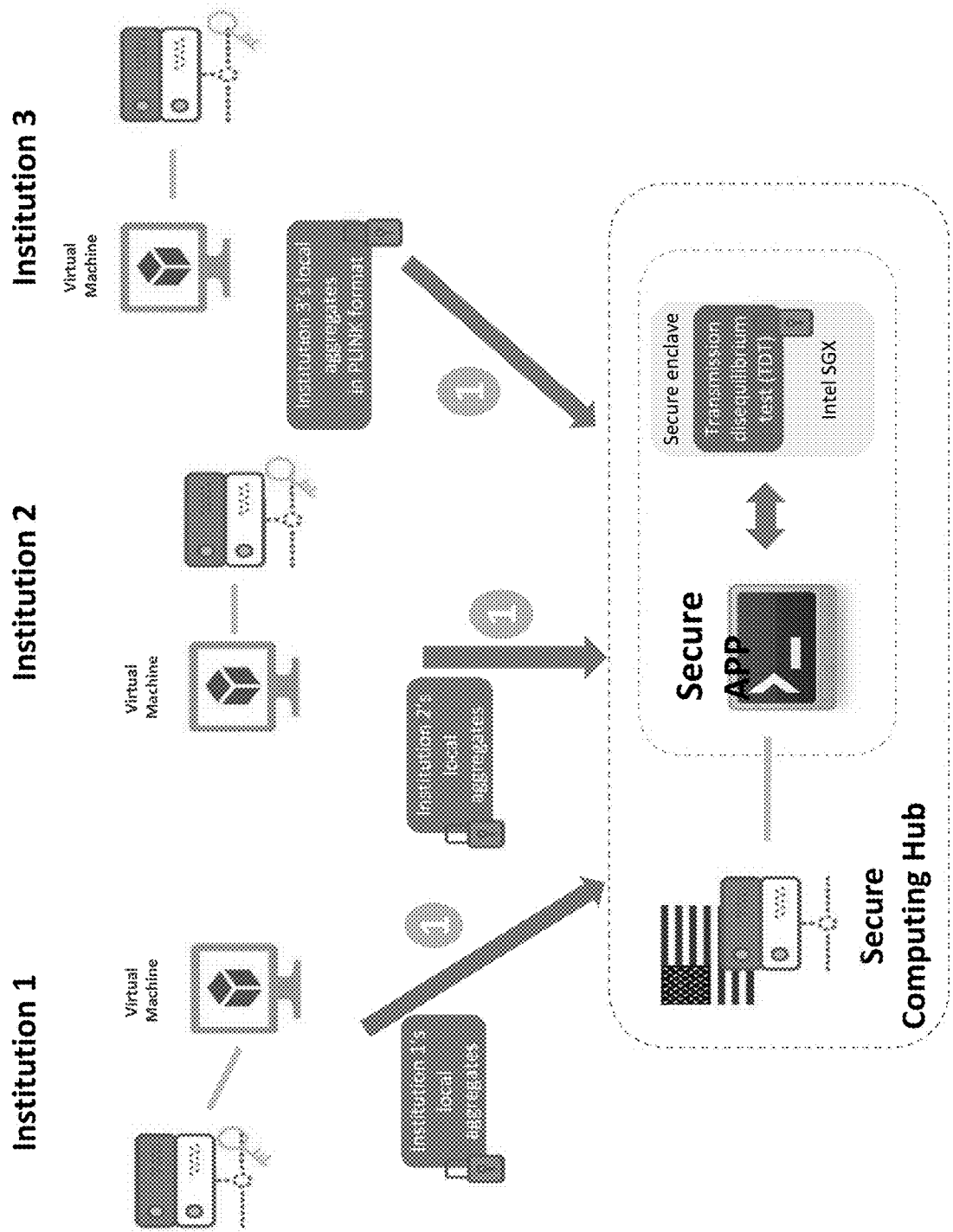
Figure 25:
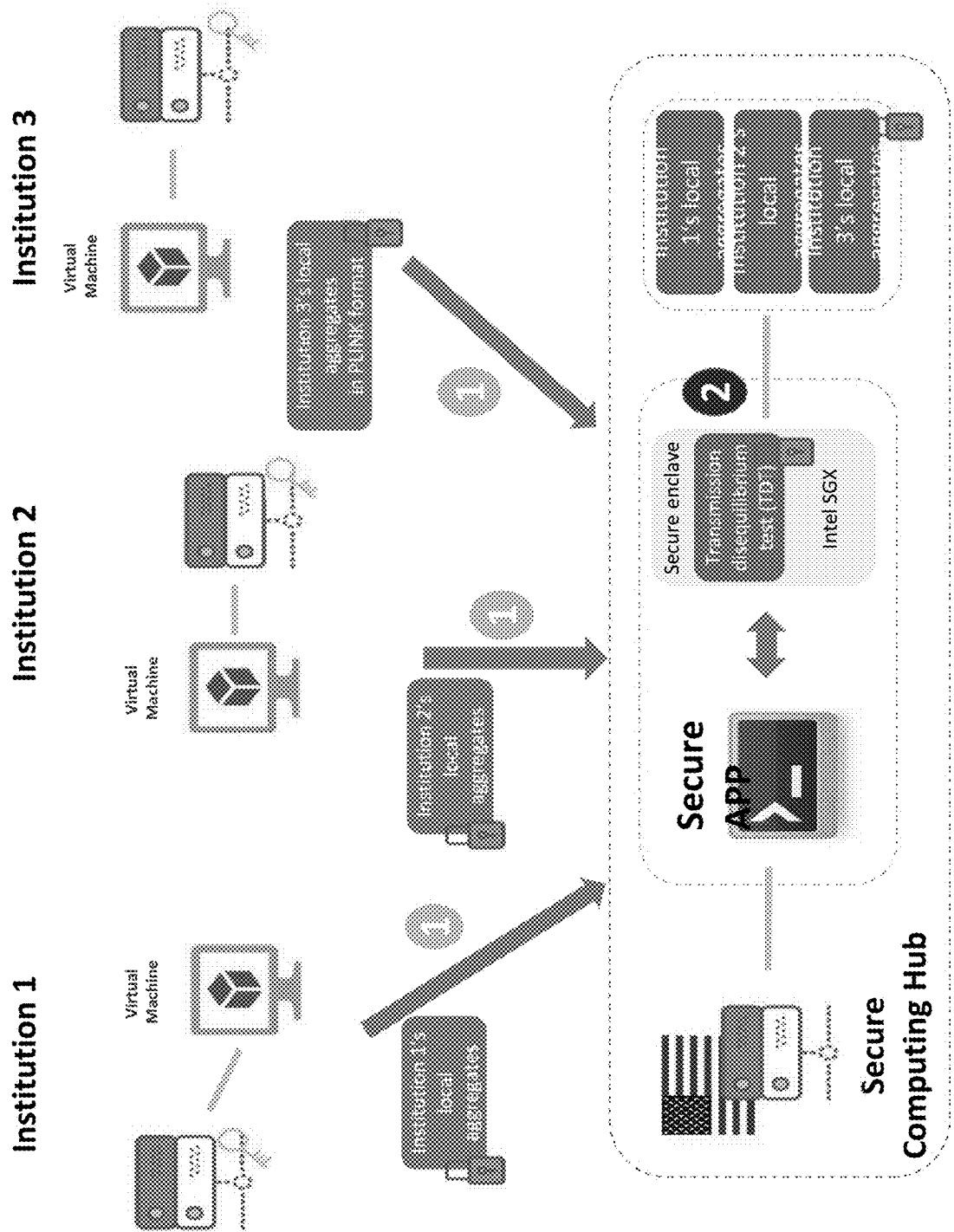
Figure 26:
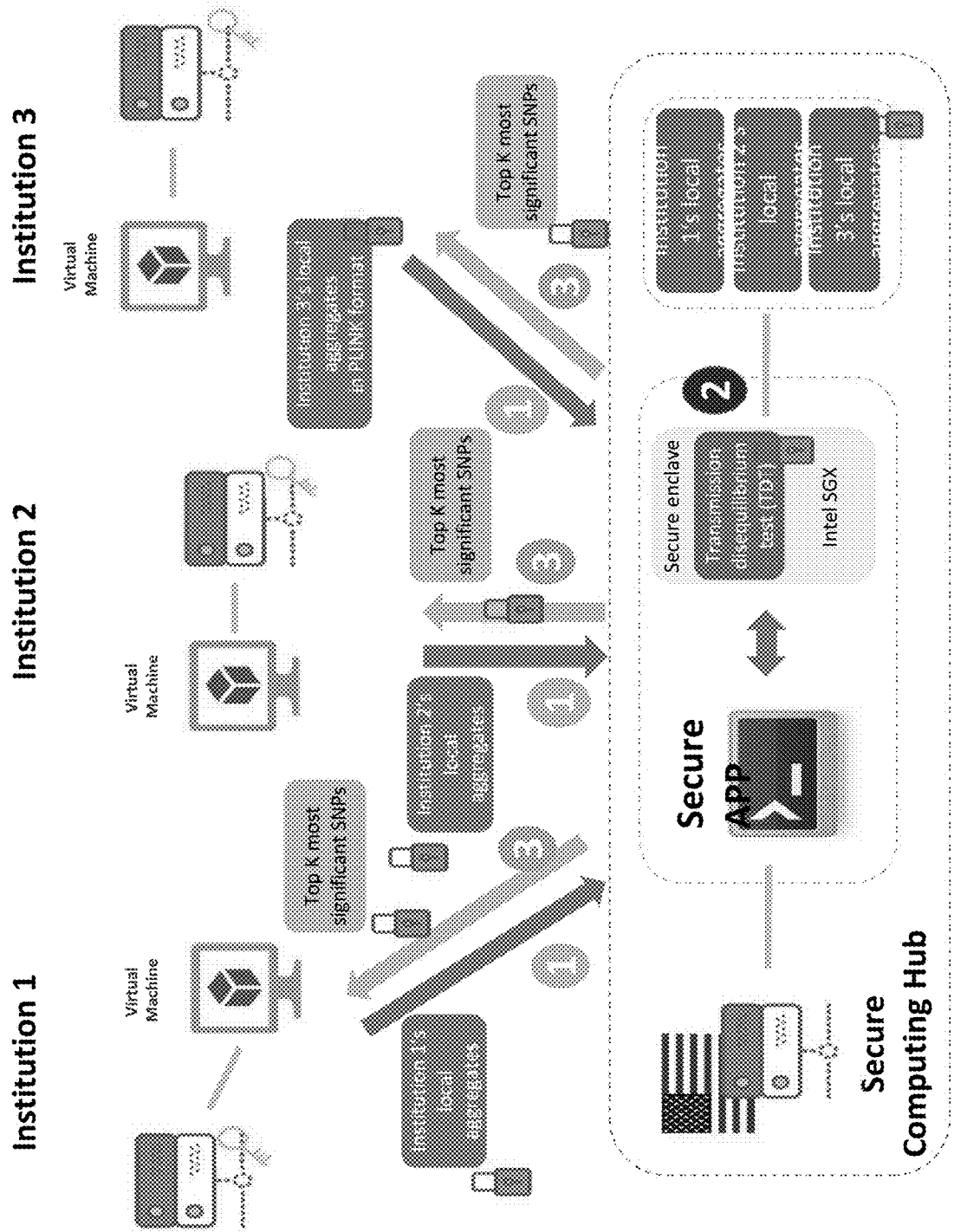

FIG. 22 shows a transmission disequilibrium test (TDT) 2200. The TDT 2200 determines genetic linkage in families comprising two parents and a child affected by a genetic condition. Genetic linkage is the tendency of two genes that are close together on the same chromosome to be inherited together. FIG. 22 shows a Punnett square 2250 including homogeneous parents (11 and 22) and heterogeneous parents (12). In particular, data showing the frequencies of heterogeneous parents either not transmitting 1 or not transmitting 2 to their affected children is used to calculate a chi-squared statistic 2280. If there were no genetic linkage in transmission of the condition, it would be expected that there would be an equal probability of transmitting either 1 or 2 to the child. But if the chi-squared statistic is large enough, it indicates that the transmitted allele to a child with the condition is not independent of the non-transmitted allele—thus, specific types of alleles are linked.

FIGS. 23-26 show a system 2300 for computing the TDT test with federated data from multiple sources. This is useful for obtaining genomic data for rare diseases, which may be distributed across continents. In the embodiments of FIGS. 23-26, TDT testing is performed on families with children exhibiting Kawasaki Disease (KD) using data from three institutions in the US, UK and Singapore, respectively. The test is done using many different types of SNPs. The SNPs most closely associated with disease transmission are ranked and sent back to each of the institutions.

The system 2300 of FIGS. 23-26 may leverage SGX in order to perform secure data analysis. The institutions' servers and a server with a secure enclave may perform remote attestation to authenticate one another. The data may then be exported from the institutions in a file format such as PLINK to the secure enclave. The enclave performs the TDT test on all of the data and sends an encrypted result back to the institutions.

Figure 27:
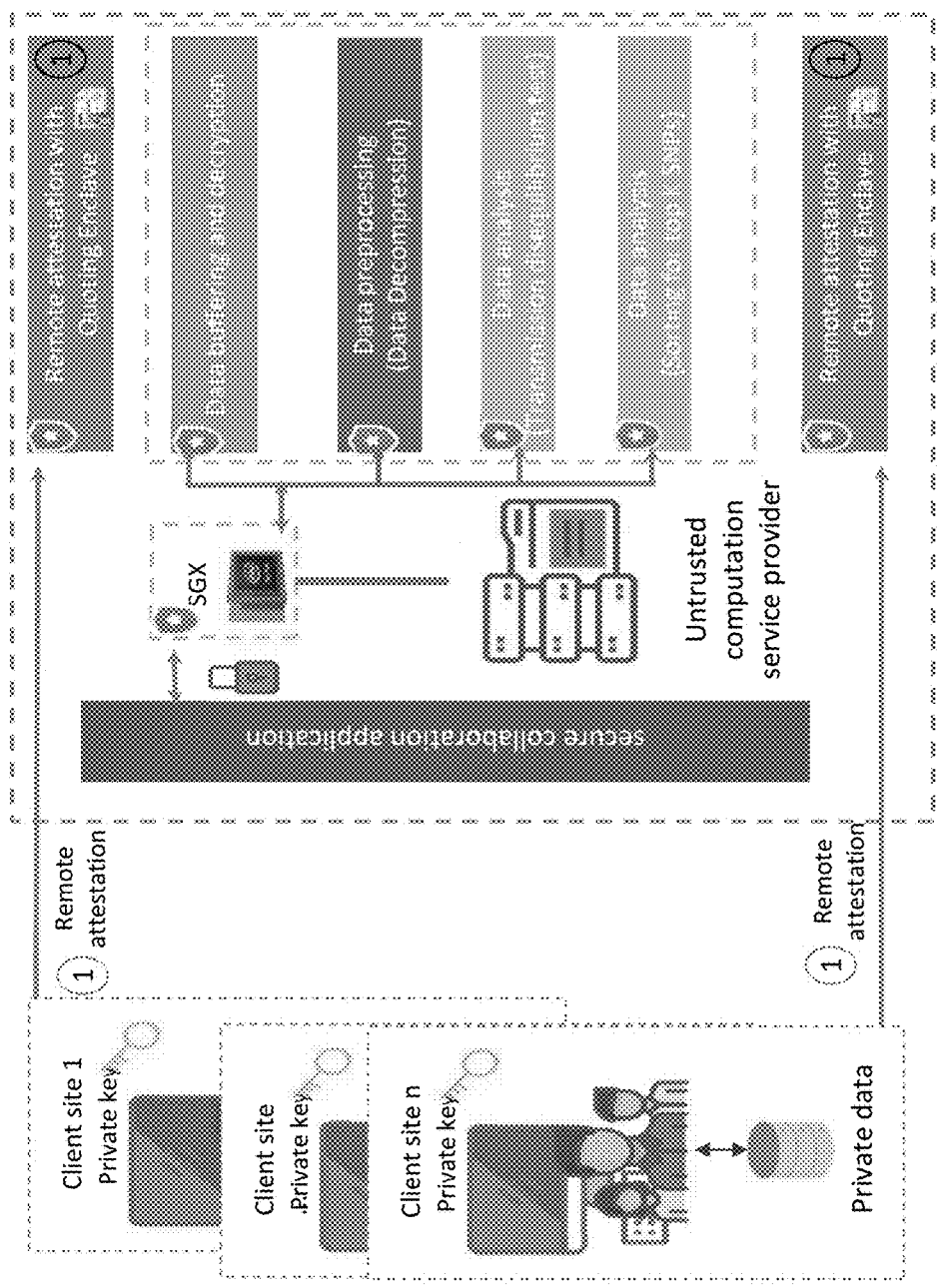
FIG. 27 illustrates the system architecture of the testing system of FIGS. 23-26.

FIG. 27 illustrates an architecture 2700 for the testing system of FIGS. 23-26. The architecture supports secure transmission and analyses of sensitive genomic data, and joint analyses without compromising either control over personally identifiable data (privacy) or disclosure of intermediary results (confidentiality), whether deliberate or accidental. The system is designed to be scalable and easy to extend with support of plug-in modules for new features/new tasks. These modules include analysis algorithms, data management tools, and compression methods. The system provides base classes for these modules and defines common application programming interfaces (APIs). Thus, when new modules are implemented based on APIs, they may be easily integrated into the system. The data management module on the client side recognizes the standard PLINK format in the input file and can parse input data into memory so that the compression module or encryption module can process parsed data accordingly. The compression module provides an interface to client sites (data owners) to transfer compressed data using range coding to the service provider, which has a static decompression library running inside the enclave (since the range-coding algorithm is lightweight, it is feasible to implement it inside the enclave). When the enclave at the server receives the encrypted data from all client sites, it can decrypt the data inside the enclave (this step is blind even to the system at the service provider). Then, the TDT is performed securely according to data owners' instructions.

Figure 28:
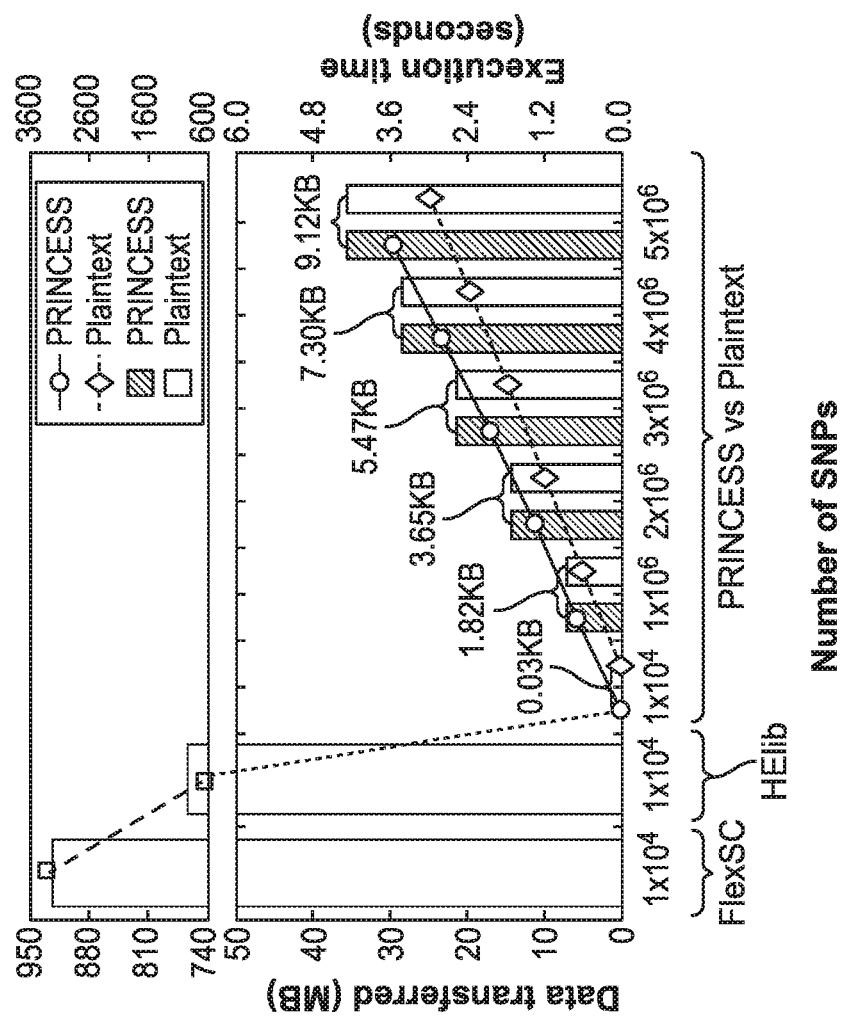
FIG. 28 shows the experimental performance of the system of FIGS. 23-26.

FIG. 28 shows the experimental performance 2800 of the system of FIGS. 23-26. FIG. 28 shows the total time spent (red line plot) and data transferred (bar plots) by three methods to compute securely with different input sizes based on a two-site setting. The system's performance is comparable to performance on a plaintext system, and much faster than an HME-based system.

Figure 29:
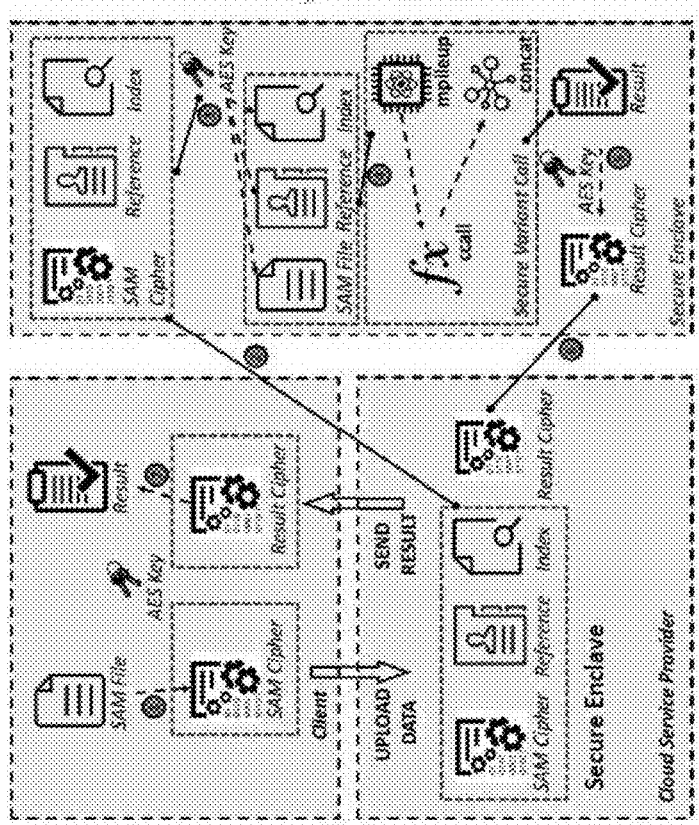
FIG. 29 shows a method of using secure enclaves to perform secure variant calling.

FIG. 29 shows a method 2900 of using secure enclaves to perform secure variant calling. FIG. 29 shows a performance evaluation using a hybrid secure computation framework that combines both trusted execution environment (TEE) system and homomorphic computation system.

The method of FIG. 29 allows analysis to be performed in a way that ensures data security and privacy. This is achieved by performing secure computations within enclaves, such as Intel® software guard extensions (SGX). Variant calling (VC) identifies variants from sequence data. In variant calling, an entire genome is sequenced and then aligned. The sequenced, aligned genome may be compared to a reference genome. Variants are found where the sequenced genome differs from the reference genome, and recorded into a variant calling format (VCF). VC can be conceptually demanding. Outsourcing VC computation may be beneficial for large-scale data analysis, but it is difficult to preserve privacy when computation is outsourced. FIG. 29 describes a secure architecture configured to preserve privacy while outsourcing VC computation.

The secure architecture includes three components, a cloud service provider (CSP), data owners, and an attenuation service provider. A cloud server may be an untrusted entity which can provide elastic computation capabilities. Data owners seek to outsource computation onto the CSP.

FIG. 29 shows a process for securely outsourcing computation onto the CSP. First, a secure VC server at the CSP and a data owner's client device perform a remote attestation. This enables both parties to prove each other's identities and securely negotiate encryption keys. The secure architecture may use AES Galois Counter Mode (AES-GCM) encryption. Next, private genome data may be securely provisioned onto the CSP and sealed outside the SGX enclave in a protected storage area. Next, the data owner may send encrypted command line requests to an SGX enclave running at the CSP. The enclave may then process the command line requests by loading and unsealing the private genome data. Because the data is still within the protective enclave, it is invisible to processes running elsewhere on the CPU and safe from attack or compromise. After the genomic data is unsealed, the enclave performs a variant calling task and returns encrypted results to the data owner using an encrypted VCF file. Using its encryption key, the data owner may decrypt the results.

FIG. 29 also shows a table 2950. The table 2950 shows runtime performance data for running the secure variant calling function. Compared to the plaintext evaluation "BCFTools", the table shows that the secure variant calling method adds 10-15% computational overhead. The table thus shows that the secure variant calling method is efficient, as encryption using other methods may add significantly more overhead.

FIG. 30 shows an illustration of a method 3000 to perform fully homomorphic encryption (FHE) in order to perform analysis on large data sets. The illustrated method allows data to be outsourced from data owners to cloud service providers, which may have ample resources to process, store, and analyze massive data sets. FHE allows any computation to be executed on encrypted data in order to return an encrypted result to a data owner.

FHE schemes allow secure calculations of an unlimited number of addition and multiplication operations. Many HE schemes add noise to ciphertext as calculations are performed. After many iterations, the ciphertext becomes too noisy to further perform calculations, and the cumulative noise needs to be removed from the ciphertext. This process is called bootstrapping. HE may be performed within a secure enclave, such as an Intel SGX enclave. This is called a trusted execution environment-assisted FHE (TEEFHE). Although performing these calculations in such an environment may prevent many attacks, the calculations may be vulnerable to side-channel attacks. In side-channel attacks, an adversary at the OS-level may perform operations that allow the adversary to infer the content of user data, such as inducing page faults and monitoring cache.

The method disclosed in FIG. 30 uses an enclave-based TEE in order to perform bootstrapping on ciphertext to be computed, and maintain privacy of the data owners. The method includes users, such as the data miners, who outsource computations to cloud service providers. Homomorphic computation (HC) nodes perform the secure calculations, and bootstrapping nodes remove noise from the encrypted ciphertext.

In a first step, the users verify a configuration of the cloud through remote attestation, and establish a shared secret key with the bootstrapping nodes. The users then provision their encryption parameters as well as the secret and public keys to the bootstrapping nodes through the established secret channel. The user's data encrypted under the homomorphic secret key may then be sent to the HC nodes to perform homomorphic computations. If the computation requires private data from multiple users, each user may send the data encrypted using his or her own key to the HC nodes. When bootstrapping is needed in the homomorphic computation, the current intermediate ciphertext may be sent from the HC nodes to the bootstrapping nodes. The bootstrapping nodes, running inside a secure enclave, first decrypt the ciphertext, then re-encrypt it using the secret key and send the refreshed ciphertext back to the HC nodes. This TEE-based bootstrapping step removes the noise in the ciphertext, and thus enables further homomorphic computation by the HC nodes.

FIG. 30 illustrates a table 3050, which shows runtime data for various operations, measured in microseconds, for different values of the parameter n (a general parameter for homomorphic encryption, with an impact on ciphertext encryption characteristics). The table shows that the method of FIG. 30, using SGX enclave bootstrapping, runs orders of magnitude faster than methods using software-only bootstrapping.

Figure 31:
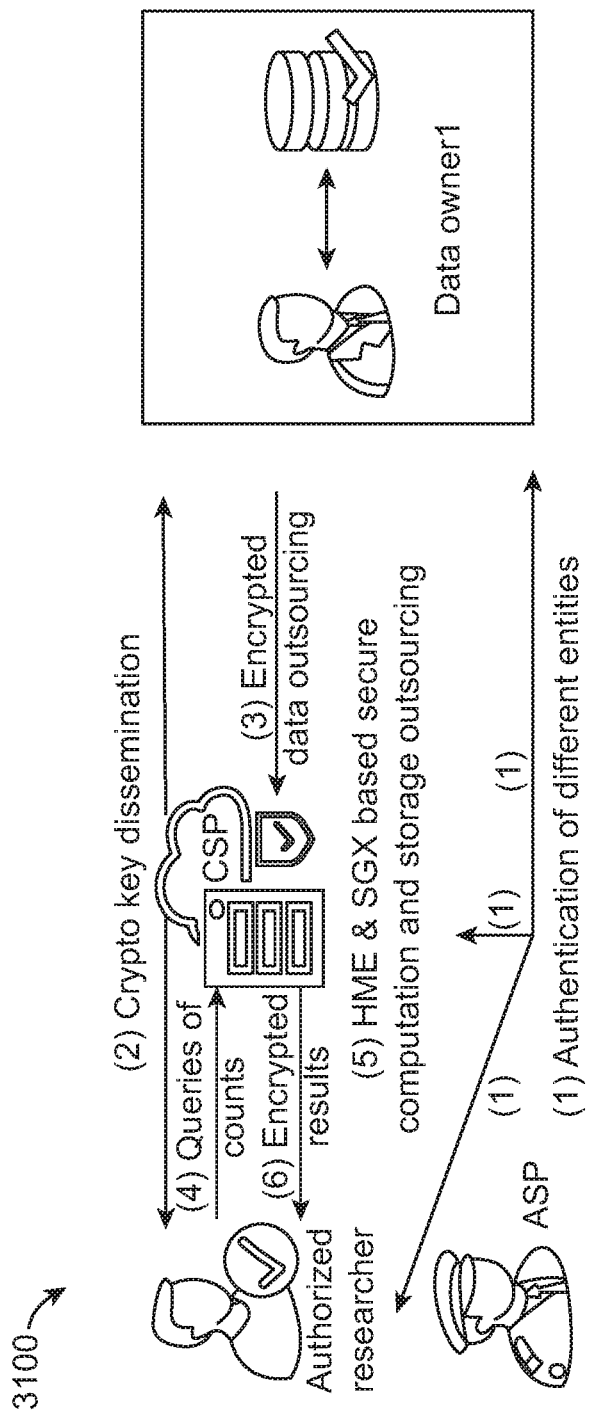
FIGS. 31 and 32 show a framework for securely executing count query on genomic data.
Figure 32:
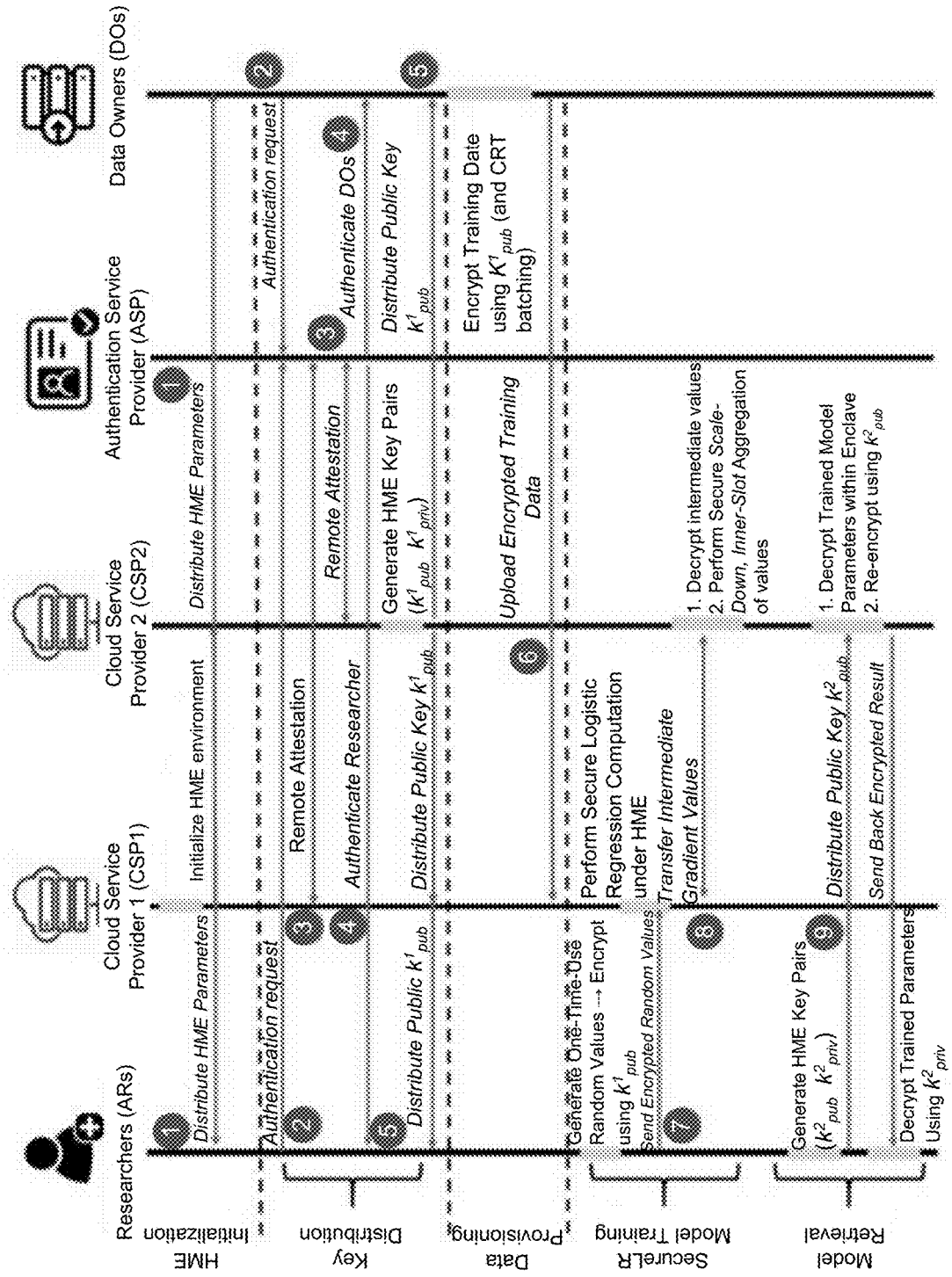

FIGS. 31 and 32 show a framework for securely executing count query on genomic data using the hybrid secure computation framework. Counting query of genotypes is a basic function for many downstream applications in biomedical research (e.g., computing allele frequency, calculating chi-squared statistics).

FIG. 31 shows an overview 3100 of the framework and its components. The authentication service provider (ASP) is a trusted entity, which can authenticate (1) data owners to securely outsource their sensitive and private data to a public cloud, (2) authorized researchers to initiate data analysis queries and to securely receive the final results, and (3) the secure enclave that is running on the SGX-enabled hardware hosted by an untrusted Cloud Service Provider. The cloud service provider is (CSP) an untrusted entity which can communicate with all the other entities. It provides securely outsourced storage of encrypted genomic data from the data owners. Based on a hybrid strategy using HME and SGX, the CSP securely evaluates the encrypted query from an authorized researcher against the encrypted data from the data owner to obtain the encrypted final results. Authorized researchers are individuals who have been granted the permission by the ASP to execute a query (i.e., the counts of multiple alleles of a genomic database). An authorized researcher sends the query to the CSP and receives encrypted results based on data from certain data owners. Data owners (are institutions or hospitals that possess databases upon which would like to outsource both storage and computation on the public cloud and allow authorized researcher to perform queries.

FIG. 32 shows an implementation 3200 of the framework workflow. The framework workflow contains three major steps: key distribution, data provisioning, and secure query execution. Key distribution exchanges the HME encryption keys among the CSP, data owners, and authorized researchers. Data owners securely pack their private genomic data and upload to the CSP through data provisioning. Then, researchers execute secure queries on CSP and count the results.

Figure 33:
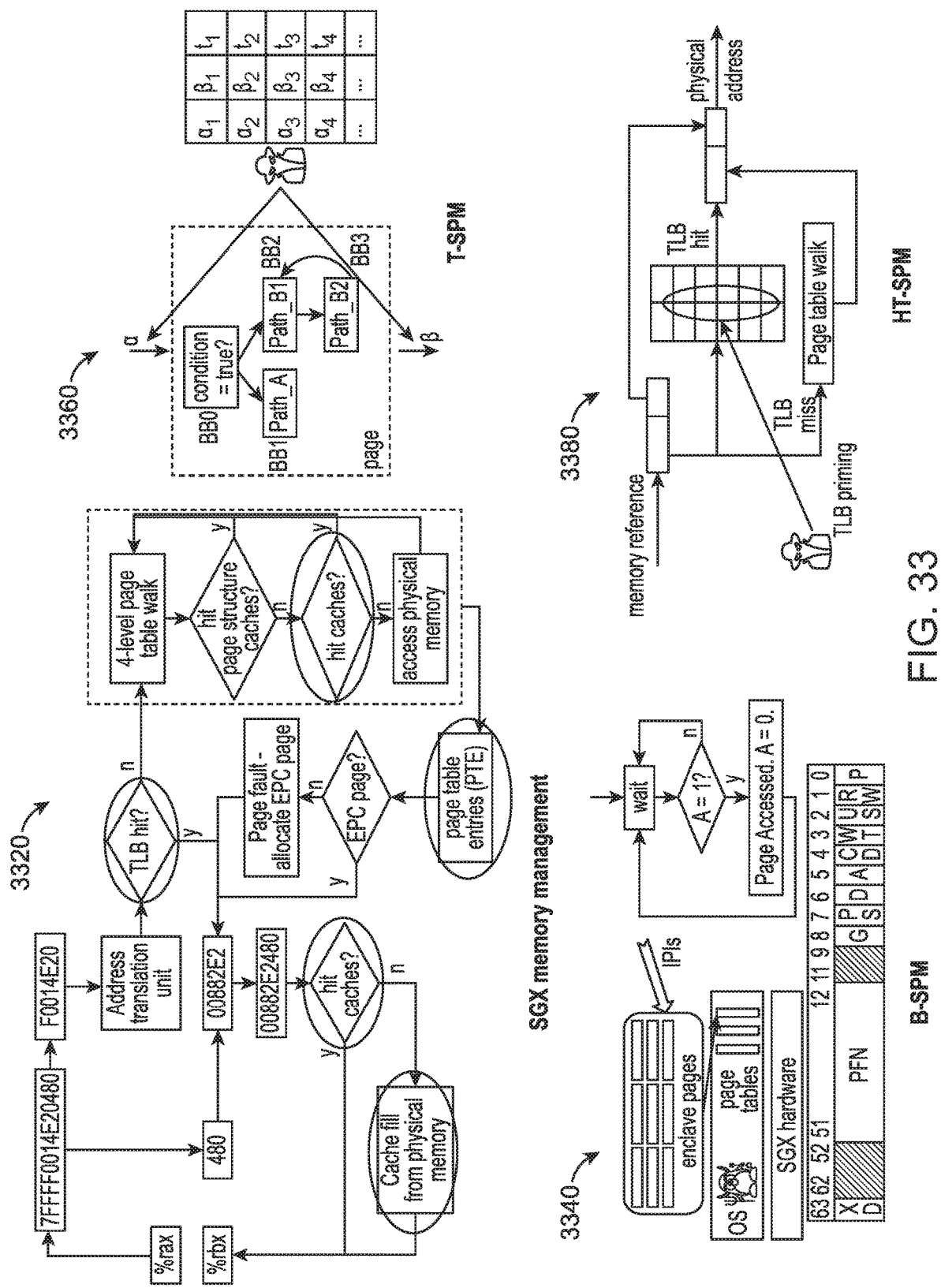
FIG. 33 illustrates examples of side-channel attacks that may compromise data security in SGX systems.

FIG. 33 illustrates examples of side-channel attacks that may compromise data security in SGX systems. Side-channel attacks are attacks in which an adversary outside of an enclave, such as an SGX enclave, can infer sensitive information inside the enclave from observed operations on resources used by the enclave which are partially or fully controlled by the operating system (an untrusted system). Side channel attacks may be performed by attackers who manipulate page tables. These attackers may identify an execution trace of a program in order to extract text documents, outlines of images, and compromising cryptographic operations. Such attacks are called page-fault side-channel attacks. FIG. 33 also illustrates a diagram 3320 of memory management in an SGX environment.

A class of memory-based side-channel attacks is called sneaky page monitoring (SPM). SPM sets and resets a page's accessed flag in order to monitor when the page is visited. Such monitoring does not directly cause interrupts, which would alert an enclave owner to an attacker by slowing down the system. Reducing the number of interrupts reduces the chance of the attack being detected.

One type of SPM attack is a B-SPM attack, or basic SPM attack 3340. This attack, as discussed earlier, simply manipulates and monitors the accessed flags on the pages of an enclave process to identify its execution trace.

Another type of SPM attack, the T-SPM 3360, is configured to account for repeated visits to a page. When repeated visits occur during an attack, the translation lookaside buffer (TLB) is shut down, causing an interrupt. Thus, repeated visits may cause an enclave owner to detect an attack. T-SPM mitigates this by leveraging a timing channel to enhance SPM, making it stealthier. Specifically, given a code fragment with a unique entry page $\alpha$ and a unique exit page $\beta$, together with multiple input-dependent paths between the two points on different pages, T-SPM continuously monitors $\alpha$ and $\beta$, measuring the execution time between these two points, and once the accessed flag of $\beta$ is found to be set, flushes the TLB and resets the accessed flags for both PTEs. The timing recorded is then used to infer the input of the code fragment.

Finally, HT-SPM 3380 is used when HyperThreading is enabled for a processor to clear up TLBs without shutting them down and causing interrupts. In HyperThreading, two virtual cores are run on a physical core, in order to handle workloads from two different operating system processes. The processes running on the two virtual cores share some of the TLBs, which allows the attacker to remove some TLB entries outside the enclave, without causing any interrupts.

Figure 34:
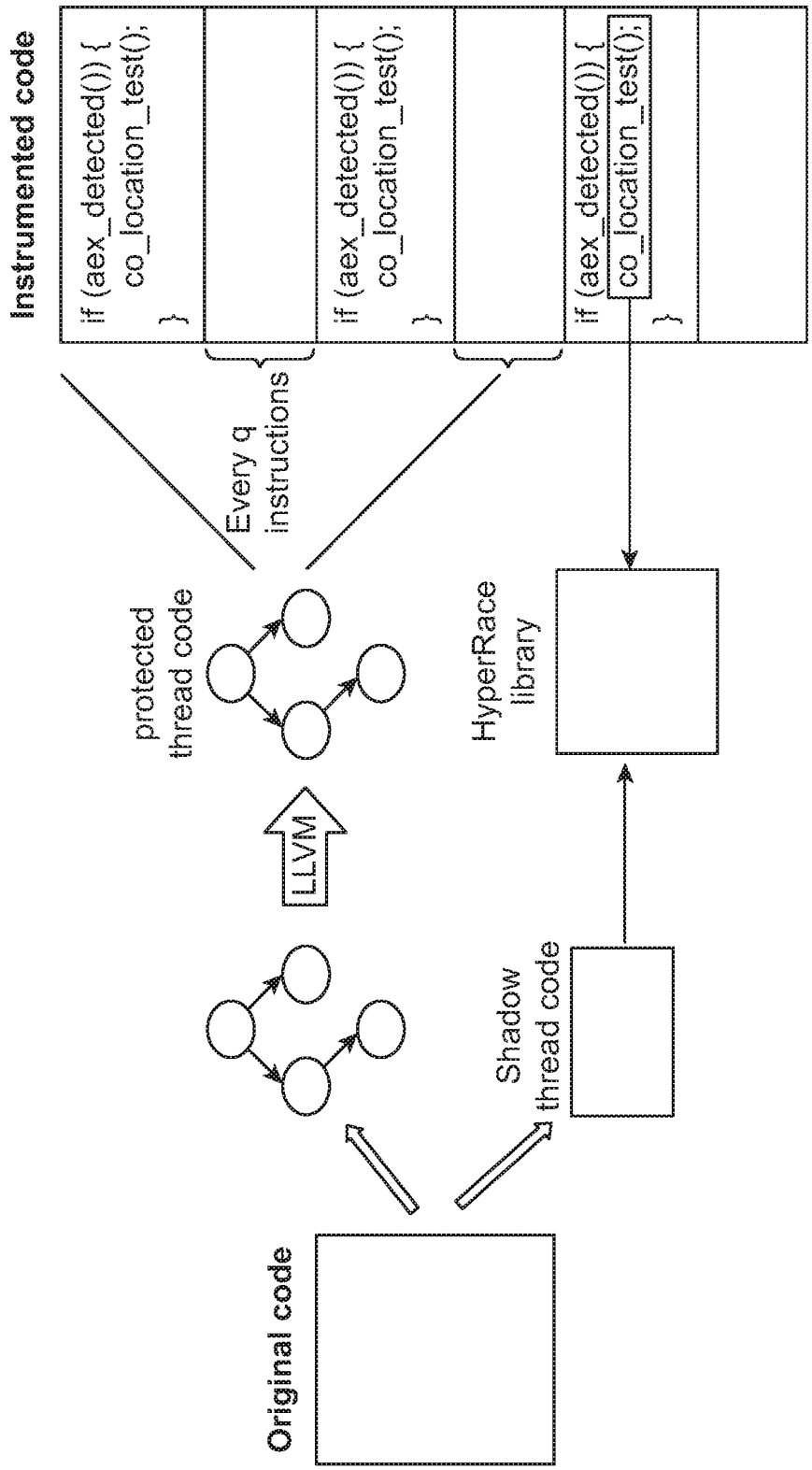
FIG. 34 shows a method for protecting data from attacks in a HyperThreading environment using Intel SGX.

FIG. 34 shows a method 3400 for protecting data from attacks in a HyperThreading environment using Intel SGX. The method uses a physical core co-location test using contrived data races between two threads running in the same enclave. A co-location test is a test that verifies that two process threads are on the same core. Contrived data races instruct two threads to continuously read from and write to a shared variable. By carefully constructing the read-write sequences, it is ensured that when both threads operate on the same core, they will read from the shared variable the value stored by the other thread with very high probabilities. Otherwise, when the threads are scheduled to different cores, they will, with high probabilities, only observe values stored by themselves. The test runs the co-location test on a protected thread and a shadow thread. The test relies on the OS to schedule the protected thread and its shadow thread to the same physical core at the beginning, which is then verified by the protected thread before running its code. Because thread migration between logical cores requires context switches (which induce asynchronous enclave exits (AEX)), the protected thread periodically checks the occurrence of AEX at runtime and whenever an AEX is detected, verifies its co-location with the shadow thread again, and terminates itself once a violation (signifying an attack) is detected.

The method 3400 guarantees that when the two threads run on co-located logical cores of the same physical core, they will both observe data races on a shared variable with a close-to-one probability. An adversary is not able to schedule the two threads on different physical cores while keeping the same probability of data races that are observed by the enclave threads.

Figure 35:
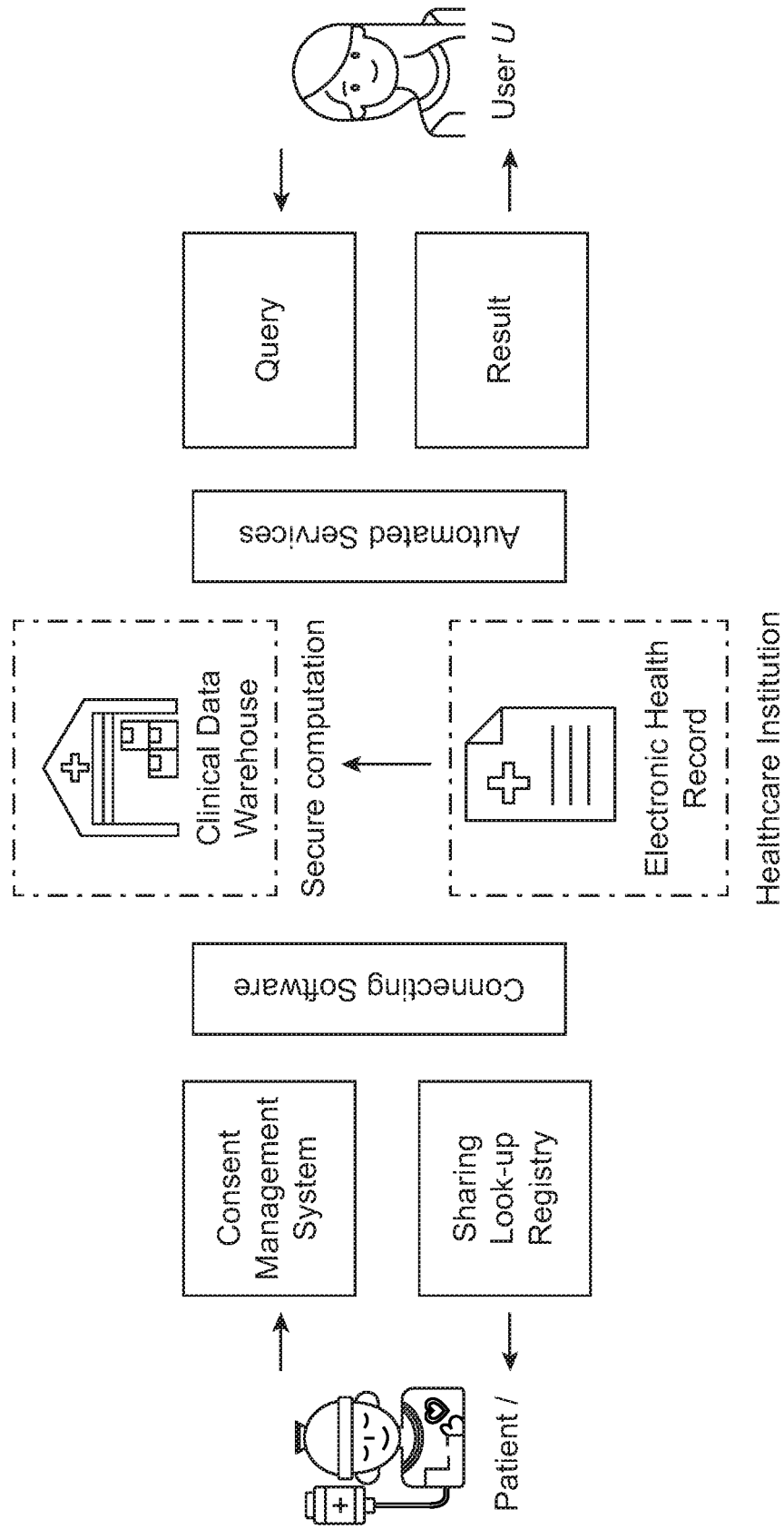
FIGS. 35 and 36 are directed for a method for providing informed consent for sharing genomic information.
Figure 36:
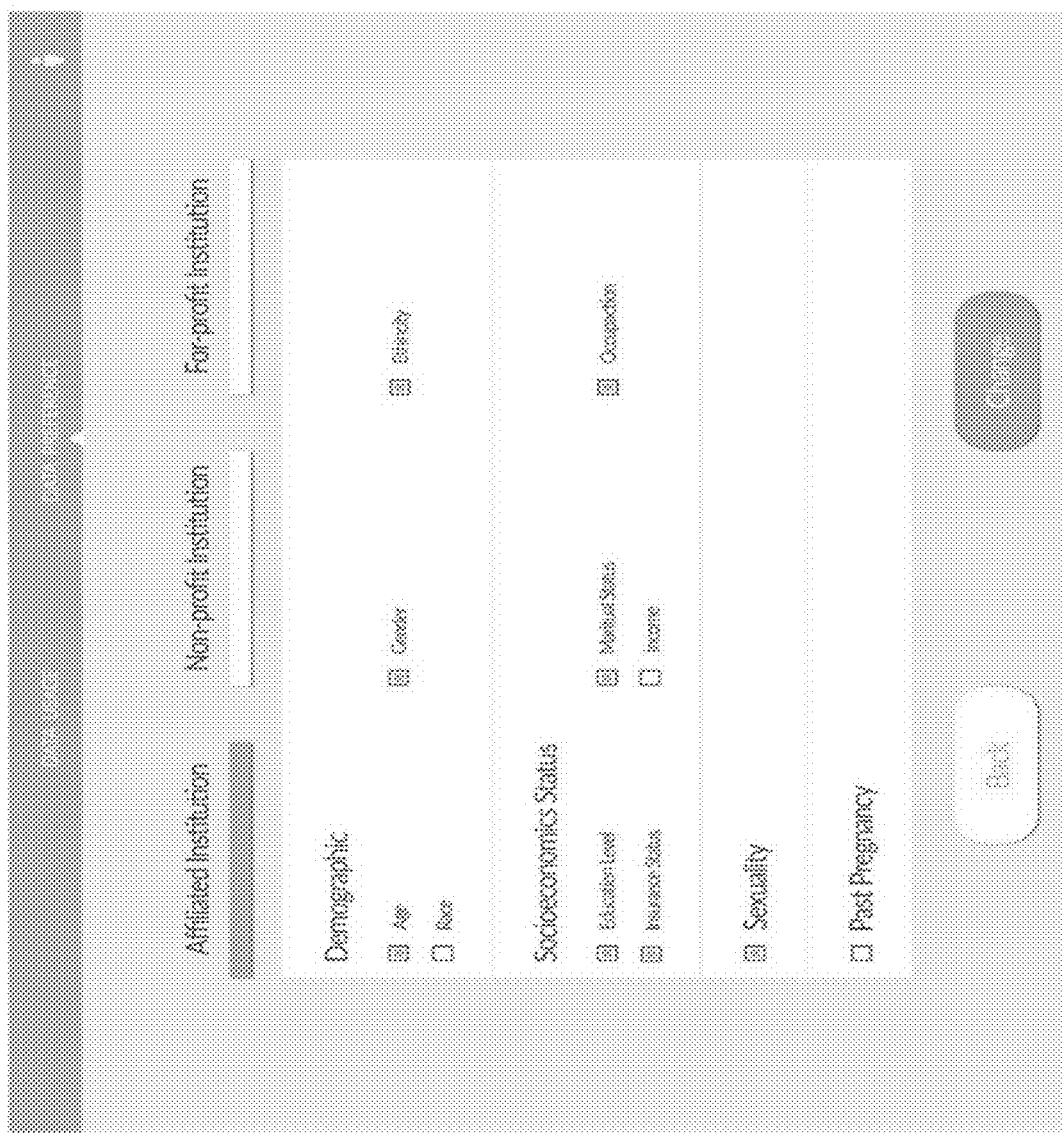

FIGS. 35 and 36 are directed for a method for providing informed consent for sharing healthcare and genomic information. The method includes a user interface that may enable users to provide dynamic consent for sharing their personal health data. The method provides patients with options for sharing one or more data elements, including demographic information, socioeconomic information, disease history, social history, and test results. The user interface may enable users to select which types of researchers and health care providers they wish to share data with. Such a granular system may help health care providers and researchers study what types of data contributors are willing to share and determine methods for obtaining consent from the contributors.

FIG. 36 shows a web portal user interface 3600 allowing a data contributor to share data with data miners. The portal shows characteristics that a data contributor may share with a data miner. The characteristics include age, ethnicity, gender, race, education level, insurance status, marital status, occupation, income, sexuality, and pregnancy status. The contributor may also choose one or more institutions with which to share the data. In FIG. 36, these institutions include university hospitals, non-profit organizations, and for-profit organizations.

Such designations are provided by way of example only. A data contributor may specify to share information on any level of specificity. For example, a data contributor may choose to share or not to share particular categories of information. For example, the data contributor may be comfortable with sharing all financial information, but not sharing health related information. A category of information may have one or more specific items of information. In some instances, a data contributor may specify whether the data contributor chooses to share the one or more specific items of information. For example, within a financial category, the data contributor may choose to share the data contributor's income, but not share debt information. In another example, the data contributor may share the data contributor's age and gender, but not share ethnicity. Any number of categories or subcategories of information may be provided. In some instances, default settings may be provided whether a data contributor shares information or not. For example, the default setting may be that the data contributor not share information, unless the data contributor specifically indicates that the data contributor is willing to share information.

The data contributor may also determine the types of data miners that may be granted information. For example, a data contributor may share certain information with a research institution, but not share the same information with a pharmaceutical company. In some instances, for each category, subcategory, or specific item of information, the data may be able to control who may be able to access the information. This may affect the results of what type of information shows up in a data miner's search.

A data contributor may have the option of opting in or out of particular programs. For instance, a data contributor may be able to opt out of participating in government surveys or other types of studies. A data contributor may be able to store the data contributor's information, while opting out of having the data contributor's information accessed. For instance, the data contributor may choose to not make all of the data contributor's information or certain portions of the data contributor's information available to data miners. The systems and methods provided herein may be designed to protect the data contributor's privacy. Data that the data contributor does not choose to share may be anonymized. Even if a data miner accesses certain health information from the data contributor, the data miner may not be obtained to obtain any identifying or personal information about the data contributor, unless the data contributor chooses the share the information. The encryption systems and methods may aid in insuring privacy.

As previously described, a data contributor may be able to control one or more pricing points for the data contributor's data. A user interface may allow a data contributor to control the pricing point. The user interface may provide one or more regions where a data contributor may enter a price to access the data contributor's data. In some instances, the price may be the same regardless of an entity that accesses the data contributor's data. Alternatively, the price may vary depending on one or more factors. For instance, the data contributor may specify different prices depending on the identity or type of the data miner. For example, a data contributor may provide a higher price for a for-profit drug company vs. a non-profit research institution. The data contributor may only allow certain entities or types of entities to purchase the data contributor's data. In some instances, the system may calculate a recommend pricing point, or pricing point range depending on data provided by other contributors. For instance, if other data contributors with similar key characteristics to a particular data contributor are able to sell data at a particular price point, this data may be made available to the data contributor, or a pricing point may be recommended and displayed on the user interface. In some instances, a recommended pricing point or range may be displayed as a numerical value or a range of numerical values. In some instances, the pricing recommendations may be provided in a graphical manner, such as a pricing curve, graph, chart, histogram, or any other manner. A graphical display may advantageously allow a user to intuitively grasp the pricing data from multiple data points and come to the user's own conclusion on a desired price.

Computer Systems

Figure 37:
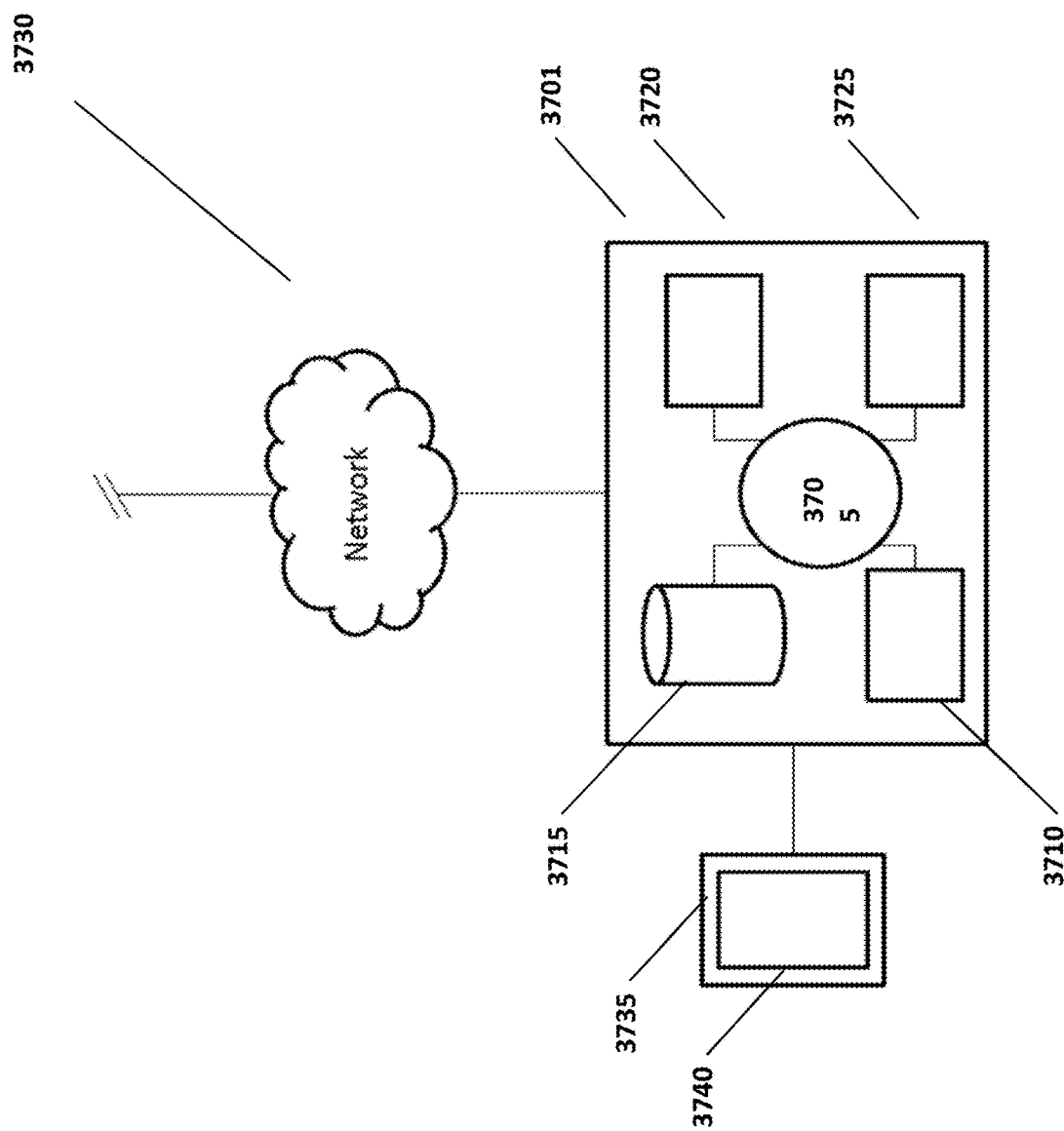
FIG. 37 shows a computer system that is configured or otherwise programmed to implement the methods disclosed herein.

The present disclosure provides computer systems that are programmed to implement methods of the disclosure. FIG. 37 shows a computer system 3701 that is programmed or otherwise configured to perform data sharing and analysis tasks. The computer system 3701 can regulate various aspects of the present disclosure, such as, for example, storing health data, encrypting data, performing key exchange, performing analysis on data, performing secure computations, and issuing digital tokens. The computer system 3701 can be an electronic device of a user or a computer system that is remotely located with respect to the electronic device. The electronic device can be a mobile electronic device.

The computer system 3701 includes a central processing unit (CPU, also "processor" and "computer processor" herein) 3705, which can be a single core or multi core processor, or a plurality of processors for parallel processing. The computer system 3701 also includes memory or memory location 3710 (e.g., random-access memory, read-only memory, flash memory), electronic storage unit 3715 (e.g., hard disk), communication interface 3720 (e.g., network adapter) for communicating with one or more other systems, and peripheral devices 3725, such as cache, other memory, data storage or electronic display adapters. The memory 3710, storage unit 3715, interface 3720 and peripheral devices 3725 are in communication with the CPU 3705 through a communication bus (solid lines), such as a motherboard. The storage unit 3715 can be a data storage unit (or data repository) for storing data. The computer system 3701 can be operatively coupled to a computer network ("network") 3730 with the aid of the communication interface 3720. The network 3730 can be the Internet, an internet or extranet, or an intranet or extranet that is in communication with the Internet. The network 3730 in some cases is a telecommunication or data network. The network 3730 can include one or more computer servers, which can enable distributed computing, such as cloud computing. The network 3730, in some cases with the aid of the computer system 3701, can implement a peer-to-peer network, which may enable devices coupled to the computer system 3701 to behave as a client or a server.

The CPU 3705 can execute a sequence of machine-readable instructions, which can be embodied in a program or software. The instructions may be stored in a memory location, such as the memory 3710. The instructions can be directed to the CPU 3705, which can subsequently program or otherwise configure the CPU 3705 to implement methods of the present disclosure. Examples of operations performed by the CPU 3705 can include fetch, decode, execute, and writeback.

The CPU 3705 can be part of a circuit, such as an integrated circuit. One or more other components of the system 3701 can be included in the circuit. In some cases, the circuit is an application specific integrated circuit (ASIC).

The storage unit 3715 can store files, such as drivers, libraries and saved programs. The storage unit 3715 can store user data, e.g., user preferences and user programs. The computer system 3701 in some cases can include one or more additional data storage units that are external to the computer system 3701, such as located on a remote server that is in communication with the computer system 3701 through an intranet or the Internet.

The computer system 3701 can communicate with one or more remote computer systems through the network 3730. For instance, the computer system 3701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 3701 via the network 3730.

Methods as described herein can be implemented by way of machine (e.g., computer processor) executable code stored on an electronic storage location of the computer system 3701, such as, for example, on the memory 3710 or electronic storage unit 3715. The machine executable or machine readable code can be provided in the form of software. During use, the code can be executed by the processor 3705. In some cases, the code can be retrieved from the storage unit 3715 and stored on the memory 3710 for ready access by the processor 605. In some situations, the electronic storage unit 3715 can be precluded, and machine-executable instructions are stored on memory 3710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 3701, can be embodied in programming. Various aspects of the technology may be thought of as "products" or "articles of manufacture" typically in the form of machine (or processor) executable code or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code or data. Many of these forms of computer readable media may be involved in carrying one or more sequences of one or more instructions to a processor for execution.

The computer system 3701 can include or be in communication with an electronic display 3735 that comprises a user interface (UI) 3740 for providing, for example, a method for a user to select data to share. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 3705. The algorithm can, for example, remove selected sub-sections of a given cross-section of a 3D object.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method of managing health information, said method comprising:
   obtaining health information from a plurality of data contributors; storing the health information in an encrypted format within a memory storage;
   utilizing a blockchain system to aid in managing the health information; and
   permitting a data miner to access and analyze the health information in the encrypted format while maintaining privacy of the at least one data contributor from the data miner;
   creating a federated learning model using model parameters or intermediary analysis statistics with the assistance of a privacy-preserving computing node;
   the described process of permitting a data miner to access and analyze the health information in the encrypted format comprising:
   the data miner makes encrypted requests to the memory storage to request particular types of data analysis;
   the memory storage sequentially sends the encrypted requests to the secure computing nodes, and provides the secure computing nodes with data for secure analysis;
   the secure computing nodes encrypt the analysis results and return them to the memory storage;
   the memory storage returns the encrypted results to the data miners described.

2. The method of claim 1, wherein the data contributors do not share raw data in the federated learning model.

3. The method of claim 2, wherein the federated learning model learns a global statistical model while not sharing the data contributor data.

4. The method of claim 3, wherein the global statistical model is encrypted.

5. The method of claim 1, wherein exchange of the model parameters or the intermediary analysis statistics are protected through privacy-preserving computation over encrypted data.

6. The method of claim 1, wherein the health information is genomic data.

7. The method of claim 6, wherein the genomic data comprises DNA sequence information or RNA sequence information.

8. The method of claim 1, wherein the health information is associated with personal information about the plurality of data contributors.

9. The method of claim 8, wherein the personal information comprises demographic information or socioeconomic information about the plurality of data contributors.

10. The method of claim 1, wherein the health information has been verified by a third party that has provided a signature, which allows the health information to be included in the blockchain system.

11. The method of claim 1, wherein the federated learning model utilizes a central node that aggregates local analysis results from a plurality of local nodes and produces an aggregated output, while preserving data security for the local nodes.

12. The method of claim 1, wherein the federated learning model is created using a federated logistic regression on horizontally or vertically partitioned data.

13. The method of claim 1, wherein the health information comprises DNA sequence information or RNA sequence information.

14. The method of claim 1, wherein the health information is associated with personal information about the plurality of data contributors, wherein the personal information comprises demographic information or socioeconomic information about the plurality of data contributors.

15. A computer-implemented system for managing health information, said system comprising:
- a memory storage configured to store health information from a plurality of data contributors in an encrypted format;
- a blockchain system configured to aid in managing the health information; and
- a data miner configured to access and analyze the health information in the encrypted format while maintaining privacy of the at least one data contributor from the data miner;
- a federated learning model created using model parameters or intermediary analysis statistics with the assistance of a privacy-preserving computing node;
- the data miner configured to access and analyze the health information in the encrypted format comprising:
- the data miner makes encrypted requests to the memory storage to request particular types of data analysis;
- the memory storage sequentially sends the encrypted requests to the secure computing nodes, and provides the secure computing nodes with data for secure analysis;
- the secure computing nodes encrypt the analysis results and return them to the memory storage;
- the memory storage returns the encrypted results to the data miners described.

16. The system of claim 15, wherein the data contributors do not share raw data in the federated learning model.

17. The system of claim 15, wherein exchange of the model parameters or the intermediary analysis statistics are protected through privacy-preserving computation over encrypted data.

18. Non-transitory computer-readable storage media for managing health information, said non-transitory computer readable media comprising:
- computer code for obtaining health information from a plurality of data contributors;
- computer code for storing the health information in an encrypted format within a memory storage;
- computer code for utilizing a blockchain system to aid in managing the health information; and
- computer code for creating a federated learning model using model parameters or intermediary analysis statistics with the assistance of a privacy-preserving computing node;
- computer code for permitting a data miner to access and analyze the health information in the encrypted format while maintaining privacy of the at least one data contributor from the data miner, comprising:
- the data miner makes encrypted requests to the memory storage to request particular types of data analysis;
- the memory storage sequentially sends the encrypted requests to the secure computing nodes, and provides the secure computing nodes with data for secure analysis;
- the secure computing nodes encrypt the analysis results and return them to the memory storage;
- the memory storage returns the encrypted results to the data miners described.

19. The non-transitory computer-readable media of claim 18, wherein the data contributors do not share raw data in the federated learning model, and wherein exchange of the model parameters or the intermediary analysis statistics are protected through privacy-preserving computation over encrypted data.

20. A computer-implemented method of managing analysis applications, said method comprising:
- providing a plurality of data analysis applications that are configured to access and analyze information in associated with at least one data contributor, wherein the information is stored in an encrypted format within a memory storage and a blockchain system aids in managing the information; and
- accepting a selection of at least one data analysis application from the plurality of data analysis applications to access and analyze the information; and
- the data analysis applications permit a data miner to access and analyze the health information in the encrypted format while maintaining privacy of the at least one data contributor from the data miner; wherein:
- the data miner makes encrypted requests to the memory storage to request particular types of data analysis;
- the memory storage sequentially sends the encrypted requests to the secure computing nodes, and provides the secure computing nodes with data for secure analysis;
- the secure computing nodes encrypt the analysis results and return them to the memory storage;
- the memory storage returns the encrypted results to the data miners described.

* * * * *

UNITED STATES PATENT AND TRADEMARK OFFICE
CERTIFICATE OF CORRECTION

| | |
|---|---|
| PATENT NO. | : 11,003,791 B2 |
| APPLICATION NO. | : 16/402162 |
| DATED | : May 11, 2021 |
| INVENTOR(S) | : Shuang Wang et al. |

It is certified that error appears in the above-identified patent and that said Letters Patent is hereby corrected as shown below:

On the Title Page

Item [72], the listed province, delete "Zhenjiang" and insert -- Zhejiang --.

Signed and Sealed this
Fourteenth Day of February, 2023

Katherine Kelly Vidal
*Director of the United States Patent and Trademark Office*